US012714700B2

(12) United States Patent
Lin et al.

(10) Patent No.: US 12,714,700 B2
(45) Date of Patent: Aug. 25, 2026

(54) METHODS OF TREATING RBP4 RELATED DISEASES WITH TRIAZOLOPYRIDINES

(71) Applicants: Belite Bio, Inc, Grand Cayman (KY); The Trustees Of Columbia University In The City Of New York, New York, NY (US)

(72) Inventors: Yu-Hsin Tom Lin, San Diego, CA (US); Cheng-Chi Irene Wang, San Diego, CA (US); Konstantin Petrukhin, New Windsor, NY (US)

(73) Assignees: Belite Bio, Inc, Grand Cayman (KY); The Trustees Of Columbia University In The City Of New York

( * ) Notice: Subject to any disclaimer, the term of this patent is extended or adjusted under 35 U.S.C. 154(b) by 0 days.

(21) Appl. No.: 18/615,735

(22) Filed: Mar. 25, 2024

(65) Prior Publication Data

US 2024/0398780 A1 Dec. 5, 2024

Related U.S. Application Data

(60) Continuation of application No. 17/228,590, filed on Apr. 12, 2021, now Pat. No. 12,016,853, which is a division of application No. 16/272,911, filed on Feb. 11, 2019, now Pat. No. 11,007,186, which is a division of application No. 16/008,838, filed on Jun. 14, 2018, now Pat. No. 10,245,259.

(60) Provisional application No. 62/520,420, filed on Jun. 15, 2017.

(51) Int. Cl.

| | |
|---|---|
| ***A61K 31/4545*** | (2006.01) |
| ***A61K 9/00*** | (2006.01) |
| ***A61K 31/4985*** | (2006.01) |
| ***A61K 31/519*** | (2006.01) |
| ***A61K 31/5365*** | (2006.01) |
| ***A61K 31/5383*** | (2006.01) |
| ***A61P 3/04*** | (2006.01) |
| ***A61P 3/10*** | (2006.01) |

(52) U.S. Cl.
CPC ........ *A61K 31/4545* (2013.01); *A61K 9/0019* (2013.01); *A61K 9/0053* (2013.01); *A61K 31/4985* (2013.01); *A61K 31/519* (2013.01); *A61K 31/5365* (2013.01); *A61K 31/5383* (2013.01); *A61P 3/04* (2018.01); *A61P 3/10* (2018.01)

(58) Field of Classification Search
CPC ................................................ A61K 31/4545
See application file for complete search history.

(56) References Cited

U.S. PATENT DOCUMENTS

| | | | |
|---|---|---|---|
| 7,632,837 | B2 | 12/2009 | Sun et al. |
| 8,648,038 | B2 | 2/2014 | Defossa et al. |
| 8,680,137 | B2 | 3/2014 | Sun et al. |
| 8,980,924 | B2 | 3/2015 | Petrukhin et al. |
| 9,333,202 | B2 | 5/2016 | Petrukhin et al. |
| 9,434,727 | B2 | 9/2016 | Petrukhin et al. |
| 9,487,509 | B2 | 11/2016 | Kasai et al. |
| 9,637,450 | B2 | 5/2017 | Petrukhin et al. |
| 9,777,010 | B2 | 10/2017 | Petrukhin et al. |
| 9,926,271 | B2 | 3/2018 | Petrukhin et al. |
| 9,938,291 | B2 | 4/2018 | Petrukhin et al. |
| 9,944,644 | B2 | 4/2018 | Petrukhin et al. |
| 10,245,259 | B2 | 4/2019 | Lin et al. |
| 11,007,186 | B2 | 5/2021 | Lin et al. |
| 11,362,225 | B2 | 6/2022 | Kojima et al. |
| 11,389,444 | B2 | 7/2022 | Lin et al. |
| 12,016,853 | B2 | 6/2024 | Lin et al. |
| 12,364,693 | B2 | 7/2025 | Lin et al. |
| 2010/0022530 | A1 | 1/2010 | Schiemann et al. |
| 2011/0123521 | A1 | 5/2011 | Monia et al. |
| 2014/0066420 | A1 | 3/2014 | Kasai et al. |
| 2015/0315197 | A1 | 11/2015 | Petrukhin et al. |
| 2016/0004668 | A1 | 1/2016 | Rowles et al. |
| 2016/0046648 | A1 | 2/2016 | Petrukhin et al. |
| 2016/0046649 | A1 | 2/2016 | Petrukhin et al. |
| 2017/0114072 | A1 | 4/2017 | Yang et al. |
| 2021/0228563 | A1 | 7/2021 | Lin et al. |
| 2022/0354844 | A1 | 11/2022 | Lin et al. |
| 2022/0387400 | A1 | 12/2022 | Lin et al. |
| 2023/0241049 | A1 | 8/2023 | Petrukhin et al. |
| 2023/0312585 | A1 | 10/2023 | Petrukhin et al. |
| 2025/0295654 | A1 | 9/2025 | Lin et al. |

FOREIGN PATENT DOCUMENTS

| | | | |
|---|---|---|---|
| AU | 2015336480 | A1 | 5/2017 |
| AU | 2015336480 | A2 | 6/2017 |
| CN | 101294956 | A | 10/2008 |
| EP | 2202223 | A1 | 6/2010 |
| EP | 3210973 | A1 | 8/2017 |
| WO | WO-0174164 | A1 | 10/2001 |
| WO | WO-2009143390 | A2 | 11/2009 |
| WO | WO-2012071369 | A2 | 5/2012 |
| WO | WO-2013166037 | A1 | 11/2013 |
| WO | WO-2014151936 | A1 | 9/2014 |
| WO | WO-2014151959 | A1 | 9/2014 |
| WO | WO-2014152013 | A1 | 9/2014 |
| WO | WO-2014152018 | A1 | 9/2014 |
| WO | WO-2014160409 | A1 | 10/2014 |
| WO | WO-2015168286 | A1 | 11/2015 |
| WO | WO-2016063933 | A1 | 4/2016 |
| WO | WO-2018232150 | A1 | 12/2018 |
| WO | WO-2020028723 | A1 | 2/2020 |

OTHER PUBLICATIONS

Aguilera CM, et al. Alterations in plasma and tissue lipids associated with obesity and metabolic syndrome. Clin Sci (Lond). Feb. 2008;114(3):183-193.

(Continued)

*Primary Examiner* — Yong S. Chong
(74) *Attorney, Agent, or Firm* — Wilson Sonsini Goodrich & Rosati

(57) ABSTRACT

Provided herein are heterocyclic derivative compounds and pharmaceutical compositions comprising said compounds that are useful for the treatment of retinal binding protein (RBP4) related diseases, such as obesity and the like.

20 Claims, 24 Drawing Sheets

(56) References Cited

OTHER PUBLICATIONS

Anon, Diagnosis and Classification of Diabetes Mellitus. 2012 Diabetes care, 35 Suppl 1, pp. S64-S71.
Attie AD, et al. Adipocyte metabolism and obesity. J Lipid Res. Apr. 2009;50 Suppl:S395-S399.
Balagopal, Prabhakaran. et al. Reduction of elevated serum retinol binding protein in obese children by lifestyle intervention: association with subclinical inflammation. The Journal of clinical endocrinology and metabolism 92(5):1971-1974 (2007).
Bhat, Pangala V, et al., Serum Retinol-binding Protein, Obesity, and Insulin Resistance. Vitamin-Binding Proteins, 31-47 (2014).
Bluher et al.: Does Retinol-Binding Protein 4 Cause or Reflect Fatty Liver Disease. Hepatology. 48(1):4-6 (2008).
Cannon, Burger's Medicinal Chemistry and Drug Discovery 1995, Fifth Edition, I: Principles and Practice, Chap. 19, John Wiley & Sons, Inc., 783-802 (1995).
Chalasani et al.: The diagnosis and management of non-alcoholic fatty liver disease: Practice guideline by the American Association for the Study of Liver Diseases, American College of Gastroenterology, and the American Gastroenterological Association. Hepatology. 55:2005-2023 (2012).
Choe SS, et al. Adipose Tissue Remodeling Its Role in Energy Metabolism and Metabolic Disorders. Front Endocrinol (Lausanne). Apr. 13, 2016;7:30.
Cooke DW, et al. Type 1 diabetes mellitus in pediatrics. Pediatr Rev. Nov. 2008;29(11):374-384; quiz 385.
EP18816926.2 Examination Report dated Mar. 4, 2024.
EP18817386.8 European Examination Report dated Mar. 27, 2024.
Esteve, Eduardo. et al. Adipocytokines and insulin resistance: the possible role of lipocalin-2, retinol binding protein-4, and adiponectin. Diabetes care 32(Suppl 2):S362-S367 (2009).
European Patent Application No. EP18817386.8 Extended European Search Report dated Feb. 5, 2021.
European Patent Application No. EP19845117.1-1112 Communication Pursuant to Article 94(3) EPC issued Jun. 21, 2022.
European Patent Application No. EP19845117.1-1112 Communication Pursuant to Article 94(3) EPC issued Oct. 23, 2023.
Fabbrini E, et al. Alterations in adipose tissue and hepatic lipid kinetics in obese men and women with nonalcoholic fatty liver disease. Gastroenterology 2008;134:424-431.
Find ETDs Home Thesis Resources Find ETDs. Available at https://ndltd.org/thesis-resources/find-etds/ (Retrieved on Jan. 31, 2023).
Gavi, Shai. et al. Retinol-binding protein 4 is associated with insulin resistance and body fat distribution in nonobese subjects without type 2 diabetes. The Journal of clinical endocrinology and metabolism 92(5):1886-1890 (2007).
Gong., Research Progress on Role of Serum Retinol-binding Protein 4 in Development of Metabolic Related Diseases. Shandong Yiyao 55(19), 98-100 (2015).
Goto T, et al. Farnesol, an isoprenoid, improves metabolic abnormalities in mice via both PPAR-dependent and -independent pathways. Am J Physiol Endocrinol Metab. Nov. 2011;301(5):E1022-1032.
Graham et al.: Retinol-Binding Protein 4 and Insulin Resistance in Lean, Obese, and Diabetic Subjects. N. Engl J Med. 354:2552-2563 (2006).
International Application No. PCT/US2019/044754 International Search Report and Written Opinion dated Nov. 27, 2019.
Irwin, John et al., Zinc—a Free Database of Commercially Available Compounds for Virtual Screening. Journal of Chemical Information and Modeling. 45(1):177-182 (2005).
Johansson H, et al. Effect of fenretinide and low-dose tamoxifen on insulin sensitivity in premenopausal women at high risk for breast cancer. Cancer Res. Nov. 15, 2008;68(22):9512-9518.
Jung UJ, et al. Obesity and Its Metabolic Complications: The Role of Adipokines and the Relationship between Obesity, Inflammation, Insulin Resistance, Dyslipidemia and Nonalcoholic Fatty Liver Disease. Int J Mol Sci. Apr. 11, 2014;15(4):6184-6223.
Kahn SE, et al. Mechanisms linking obesity to insulin resistance and type 2 diabetes. Nature. Dec. 14, 2006;444(7121):840-846.
Kim, Sunghwan, et al., Pubchem in 2021: New Data Content and Improved Web Interfaces . Nucleic Acids Research 49(D1):D1388-D1395 (2021).
Klöting, Nora. et al. Serum retinol-binding protein is more highly expressed in visceral than in subcutaneous adipose tissue and is a marker of intra-abdominal fat mass. Cell metabolism 6(1):79-87 (2007).
Koh IU, et al. Fenretinide ameliorates insulin resistance and fatty liver in obese mice. Biol Pharm Bull. 2012;35(3):369-375.
Li et al., Serum retinol-binding protein 4 levels in patients with diabetic retinopathy. The Journal of International Medical Research, 38:95-99, 2010.
Moon RC, et al. N-(4-Hydroxyphenyl)retinamide, a new retinoid for prevention of breast cancer in the rat. Cancer Res. Apr. 1979;39(4):1339-1346.
Moraes-Vieira PM, et al. RBP4 Activates Antigen-Presenting Cells, Leading to Adipose Tissue Inflammation and Systemic Insulin Resistance. Cell Metab. Mar. 4, 2014;19(3):512-526.
Nair, Anup Kumar. et al. Case-control analysis of SNPs in GLUT4, RBP4 and STRA6: association of SNPs in STRA6 with type 2 diabetes in a South Indian population. PLOS One 5(7):e11444, 1-8 (2010).
Okada-Iwabu M, et al. Perspective of Small-Molecule AdipoR Agonist for Type 2 Diabetes and Short Life in Obesity. Diabetes Metab J. Oct. 2015;39(5):363-372.
Ost, Anita. et al. Retinol-binding protein-4 attenuates insulin-induced phosphorylation of IRS1 and ERK1/2 in primary human adipocytes. FASEB journal 21(13):3696-3704 (2007).
PCT/US2018/037593 International Search Report and Written Opinion dated Aug. 30, 2018.
PCT/US2018/037597 International Search Report and Written Opinion dated Aug. 28, 2018.
PCT/US2018/037606 International Preliminary Report on Patentability dated Dec. 17, 2019.
PCT/US2018/037606 International Search Report and written Opinion dated Aug. 28, 2018.
Postic C, Girard J. Contribution of de novo fatty acid synthesis to hepatic steatosis and insulin resistance: lessons from genetically engineered mice. J. J Clin Invest 2008;118:829-838.
Preitner F, et al. Long-term Fenretinide treatment prevents high-fat diet-induced obesity, insulin resistance, and hepatic steatosis. Am J Physiol Endocrinol Metab. Dec. 2009;297(6):E1420-E1429.
Samaras, Katherine. et al. Subcutaneous and visceral adipose tissue gene expression of serum adipokines that predict type 2 diabetes. Obesity 18(5):884-889 (2010).
Savage DB, et al. Disordered Lipid Metabolism and the Pathogenesis of Insulin Resistance. Physiol Rev. Apr. 2007;87(2):507-520.
STN Registry/Zregistry (CAS Registrysm) Sep. 2016 (2 pages.).
Taiwan Patent Application No. 107120497 Office Action/Search Report.
Taiwan Patent Application No. 107120499 Office Action.
Taiwan Patent Application No. 107120499 Office Action/Search Report.
Tan et al.: Suppression of retinol-binding protein 4 with RNA oligonucleotide prevents high-fat diet-induced metabolic syndrome and non-alcoholic fatty liver disease in mice. Department of Medical & Molecular BioScience. 1811(12):1045-53 (2011).
Tilg H, et al. Evolution of inflammation in nonalcoholic fatty liver disease: the multiple parallel hits hypothesis. Hepatology. Nov. 2010;52(5):1836-1846.
U.S. Appl. No. 16/008,838 Restriction Requirement dated Sep. 21, 2018.
U.S. Appl. No. 16/272,911 Restriction Requirement dated Mar. 23, 2020.
U.S. Appl. No. 16/622,252 Final Office Action dated Oct. 20, 2021.
U.S. Appl. No. 16/622,252 Office Action dated Jun. 29, 2021.
U.S. Appl. No. 17/228,590 Office Action dated Jun. 7, 2023.
U.S. Appl. No. 17/228,590 Restriction Requirement dated Apr. 7, 2023.
U.S. Appl. No. 17/228,590 Notice of Allowance dated Jan. 3, 2024.

(56) References Cited

OTHER PUBLICATIONS

U.S. Appl. No. 17/228,590 Notice of Allowance dated May 21, 2024.
U.S. Appl. No. 17/739,757 Office Action dated Apr. 29, 2024.
U.S. Appl. No. 17/739,757 Office Action dated Feb. 1, 2024.
U.S. Appl. No. 17/739,757 Office Action dated Oct. 16, 2024.
Venkatesh et al. Role of the Development Scientist in Compound Lead Selection and Optimization. J. Pharm. Sci. 89(2):145-154 (Feb. 2000).
Wang. Correlation of retinol binding protein 4 with metabolic indexes of glucose and lipid, bile cholesterol saturation index. 40(6):657-665 (2015) DOI:10.11817/j.issn.1672-7347.2015.06.014.
West. Solid Solutions. Solid State Chemistry and Its Applications. John Wiley & Sons. Chapter vol. 10: p. 358 (1984).
Wolff. Burger's Medicinal Chemistry and Drug Discovery. 5th Ed. Part 1, pp. 975-977 (1995).
Yang et al.: Berberine ameliorates non-alcoholic steatohepatitis in ApoE-/- mice. Center for Translational Medicine. 14:4134-4140 (2017).
Yang et al.: Serum retinol binding protein 4 contributes to insulin resistance in obesity and type 2 diabetes. Nature 436(7049):356-362 (2005).
Zhang et al.: Anti-diabetic effects of cinnamaldehyde and berberine and their impacts on retinol-binding protein 4 expression in rats with type 2 diabetes mellitus. Chinese Medical Association. 121(21):2124-8 (2022).
Chen, Ching-Chu. et al. Levels of retinol-binding protein 4 and uric acid in patients with type 2 diabetes mellitus. Metabolism 58(12):1812-1816 (2009).
Co-pending U.S. Appl. No. 19/231,020, inventors Lin; Yu-Hsin Tom et al., filed Jun. 6, 2025.
EP19845117.1 Communication dated Oct. 1, 2025.

Cohort 1 OGTT

HFD + vehicle:
Average Fibrosis Score 2.5

HFD + Compound 2:
Average Fibrosis Score 2.2

METHODS OF TREATING RBP4 RELATED DISEASES WITH TRIAZOLOPYRIDINES

CROSS-REFERENCE

This application is a continuation of U.S. application Ser. No. 17/228,590, filed Apr. 12, 2021, now issued as U.S. Pat. No. 12,016,853 on Jun. 25, 2024, which is a divisional of U.S. application Ser. No. 16/272,911, filed Feb. 11, 2019, now issued as U.S. Pat. No. 11,007,186 on May 18, 2021, which is a divisional of U.S. application Ser. No. 16/008,838, filed Jun. 14, 2018, now issued as U.S. Pat. No. 10,245,259 on Apr. 2, 2019, which claims the benefit of U.S. provisional patent application No. 62/520,420, filed on Jun. 15, 2017, which is incorporated herein by reference in its entirety.

STATEMENT AS TO FEDERALLY SPONSORED RESEARCH

This invention was made with government support under NS074476, and EY027027 awarded by the National Institutes of Health. The government has certain rights in the invention.

BACKGROUND

A need exists in the medicinal arts for the effective treatment of metabolic diseases and disorders associated with retinol-binding protein 4 (RBP4).

BRIEF SUMMARY OF THE INVENTION

Provided herein are methods for the treatment of obesity, diabetes, non-alcoholic fatty liver disease, or non-alcoholic steatohepatitis with heterocyclic derivative compounds and pharmaceutical compositions thereof.

Some embodiments provided herein describe methods of treating a metabolic disease or disorder in a subject in need thereof, the method comprising administering to the subject a composition comprising a therapeutically effective amount of a compound of Formula (I), a pharmaceutically acceptable salt, solvate, polymorph, prodrug, metabolite, N-oxide, stereoisomer, or isomer thereof:

Formula (I)

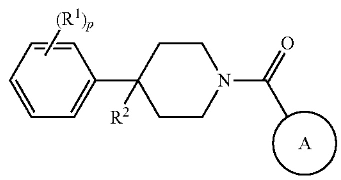

wherein:

each $R^1$ is independently halogen, haloalkyl, or alkyl;

$R^2$ is —H, —OH, or halogen;

p is 0, 1, 2, 3, 4, or 5;

A has the structure:

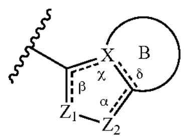

wherein:

α, β, χ, and δ are each independently absent or present, and when present each is a bond;

X is N;

$Z_1$ is S, O, or N;

$Z_2$ is S, O, N, or $NR^3$;

$R^3$ is H, $C_1$-$C_4$ alkyl, or oxetane; and

B is a substituted or unsubstituted fused 5-, 6-, or 7-membered ring structure.

In some embodiments of a compound of Formula (I), when α is present, then $Z_1$ and $Z_2$ are N, X is N, β is present, and χ and δ are absent.

In some embodiments of a method of treating a metabolic disease or disorder comprising a compound of Formula (I), A has the structure

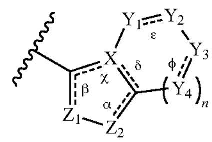

wherein:

n is 0, 1, or 2;

α, β, χ, δ, ε, and ϕ are each independently absent or present, and when present each is a bond;

$Z_1$ is S, O, or N;

$Z_2$ is S, O, N or $NR^3$, wherein $R^3$ is H, $C_1$-$C_4$ alkyl, or oxetane;

X is N;

$Y_1$, $Y_2$, $Y_3$ and each occurrence of $Y_4$ are each independently $CR^4$, $C(R^5)_2$, $NR^6$, O, N, $SO_2$, or —(C═O)—, wherein:

each $R^4$ is independently H, halogen, $C_1$-$C_{10}$alkyl, $C_1$-$C_{10}$ cycloalkyl, —O($C_1$-$C_{10}$ alkyl), —C(O)OH, —C(O)O($C_1$-$C_{10}$alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$;

each $R^5$ is independently H or $C_1$-$C_{10}$alkyl; and each $R^6$ is independently H, $C_1$-$C_{10}$alkyl, $C_3$-$C_6$ cycloalkyl, —($C_1$-$C_{10}$ alkyl)$CF_3$, —($C_1$-$C_{10}$ alkyl)$OCH_3$, —($C_1$-$C_{10}$ alkyl)-halogen, —$SO_2$($C_1$-$C_{10}$ alkyl), —$SO_2$($C_1$-$C_{10}$alkyl)-$CF_3$, —$SO_2$($C_1$-$C_{10}$alkyl)$OCH_3$, —$SO_2$($C_1$-$C_{10}$ alkyl)-halogen, —C(O)$C_1$-$C_{10}$alkyl), —C(O)($C_1$-$C_{10}$ alkyl)$CF_3$, —C(O)($C_1$-$C_{10}$alkyl)$OCH_3$, —C(O)($C_1$-$C_{10}$ alkyl)-halogen, —C(O)NH($C_1$-$C_{10}$ alkyl), —C(O)N($C_1$-$C_{10}$ alkyl)$_2$, —($C_1$-$C_{10}$ alkyl)C(O)OH, —C(O)$NH_2$, or oxetane.

In some embodiments of a compound of Formula (I), when α is present, then $Z_1$ and $Z_2$ are N, X is N, β is present, and χ and δ are absent; when ε and ϕ are each present, then n=1, and each of $Y_1$, $Y_2$, $Y_3$, and $Y_4$, are independently —$CR^4$— or N; or when ε and ϕ are each absent, then n=0, 1 or 2, each of $Y_1$, $Y_2$, $Y_3$, and each occurrence of $Y_4$ are independently $C(R^5)_2$, $NR^6$, O, or $SO_2$.

In some embodiments of a compound of Formula (I), where in α, β, ε, and ϕ are present; χ and δ are absent; $Z_1$ is N; $Z_2$ is N; and X is N.

In some embodiments of a method of treating a metabolic disease or disorder comprising a compound of Formula (I), A has the structure:

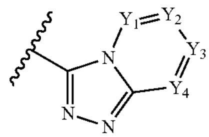

wherein:

$Y_1$, $Y_2$, $Y_3$ and $Y_4$ are each independently $CR_4$ or N; and each $R^4$ is independently H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH—($C_1$-$C_{10}$alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_5$ alkyl)$_2$, —CN, or —$CF_3$.

In some embodiments of a method of treating a metabolic disease or disorder comprising a compound of Formula (I), A has the structure:

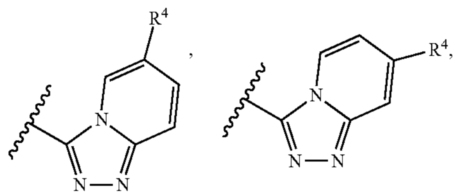

,

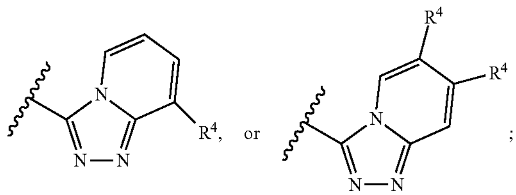

or ;

wherein:

each $R_4$ is independently H, halogen, $C_1$-$C_4$ alkyl, $C_3$-$C_6$ cycloalkyl, —O($C_1$-$C_4$ alkyl), —CN, —$CF_3$, —C(O)OH, —C(O)$NH_2$, —C(O)N($CH_3$)$_2$, —C(O)$NHCH_3$, or —NHC(O)N($CH_3$)$_2$.

In some embodiments of a method of treating a metabolic disease or disorder comprising a compound of Formula (I), each $R^1$ is independently F, Br, Cl, $C_{1-6}$ haloalkyl, or $C_{1-6}$ alkyl.

In some embodiments of a method of treating a metabolic disease or disorder comprising a compound of Formula (I), wherein each $R^1$ is independently F or $CF_3$.

One embodiment provides a method of treating a metabolic disease or disorder in a subject in need thereof, the method comprising administering to the subject a composition comprising a therapeutically effective amount of a compound having the structure:

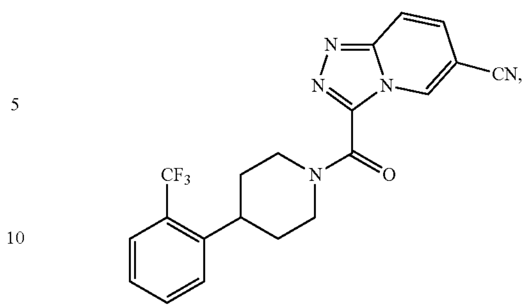

or a pharmaceutically acceptable salt, solvate, polymorph, prodrug, metabolite, N-oxide, stereoisomer, or isomer thereof.

One embodiment provides a method of treating a metabolic disease or disorder in a subject in need thereof, the method comprising administering to the subject a composition comprising a therapeutically effective amount of a compound having the structure:

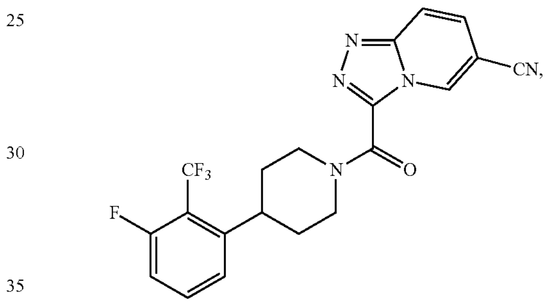

or a pharmaceutically acceptable salt, solvate, polymorph, prodrug, metabolite, N-oxide, stereoisomer, or isomer thereof.

In some embodiments, the metabolic disease or disorder is obesity, type II diabetes, diabetic retinopathy, non-alcoholic fatty liver disease (NAFLD), non-alcoholic steatohepatitis (NASH), liver fibrosis, liver cancer, or liver cirrhosis.

In some embodiments, the therapeutically effective amount of a compound of Formula (I), a pharmaceutically acceptable salt, solvate, polymorph, prodrug, metabolite, N-oxide, stereoisomer, or isomer thereof is about 25 mg per day, about 50 mg per day, about 75 mg per day, about 100 mg per day, about 150 mg per day, about 200 mg per day, or about 400 mg per day.

In some embodiments, the therapeutically effective amount of a compound of Formula (I), a pharmaceutically acceptable salt, solvate, polymorph, prodrug, metabolite, N-oxide, stereoisomer, or isomer thereof is about 50 mg per day, about 100 mg per day, about 150 mg per day, about 200 mg per day, or about 400 mg per day. In some embodiments, the therapeutically effective amount of a compound of Formula (I), a pharmaceutically acceptable salt, solvate, polymorph, prodrug, metabolite, N-oxide, stereoisomer, or isomer thereof is up to 25 mg per day, up to 50 mg per day, up to 75 mg per day, up to 100 mg per day, up to 150 mg per day, up to 200 mg per day, up to 400 mg per day, up to 600 mg per day, up to 800 mg per day, or up to 1000 mg per day. In some embodiments, the therapeutically effective amount of a compound of Formula (I), a pharmaceutically acceptable salt, solvate, polymorph, prodrug, metabolite, N-oxide, stereoisomer, or isomer thereof is up to 400 mg per day.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, the disease or disorder is obesity. In some embodiments, the disease or disorder is type II diabetes. In some embodiments, the disease or disorder is non-proliferative diabetic retinopathy (NPDR) or proliferative diabetic retinopathy (PDR). In some embodiments, the disease or disorder is a liver disease. In some embodiments, the disease or disorder is non-alcoholic fatty liver disease (NAFLD). In some embodiments, the disease or disorder is non-alcoholic steatohepatitis (NASH). In some embodiments, the disease or disorder is liver fibrosis. In some embodiments, the disease or disorder is liver cirrhosis. In some embodiments, the disease or disorder is liver cancer.

In some embodiments of a method of treating a metabolic disorder, the compound is administered to the subject orally or intravenously. In certain embodiments, the compound of Formula (I) is administered orally. In certain embodiments, the compound of Formula (I) is administered intravenously. In some embodiments, the administration is to treat an existing disease or disorder. In some embodiments, the administration is provided as prophylaxis.

INCORPORATION BY REFERENCE

All publications, patents, and patent applications mentioned in this specification are herein incorporated by reference for the specific purposes identified herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figures 1, 2:
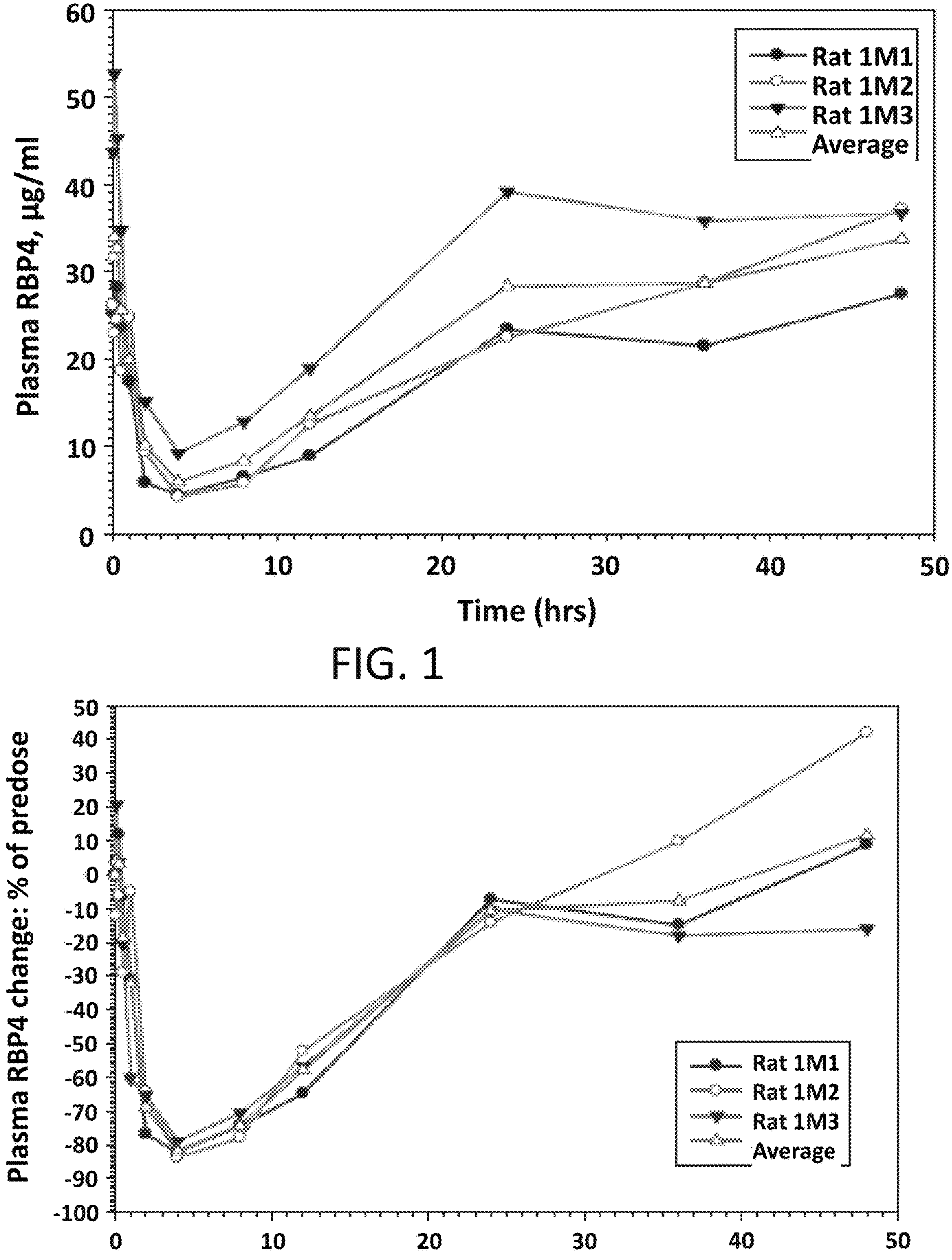
FIG. 1 illustrates absolute values of RBP4 plasma levels in male Sprague Dawley rats following a single intravenous dose of Compound 1 at 2 mg/kg.
FIG. 2 illustrates the percent reduction of RBP4 plasma levels compared to pre-dose levels in male Sprague Dawley rats following a single intravenous dose of Compound 1 at 2 mg/kg.
Figures 3, 4:
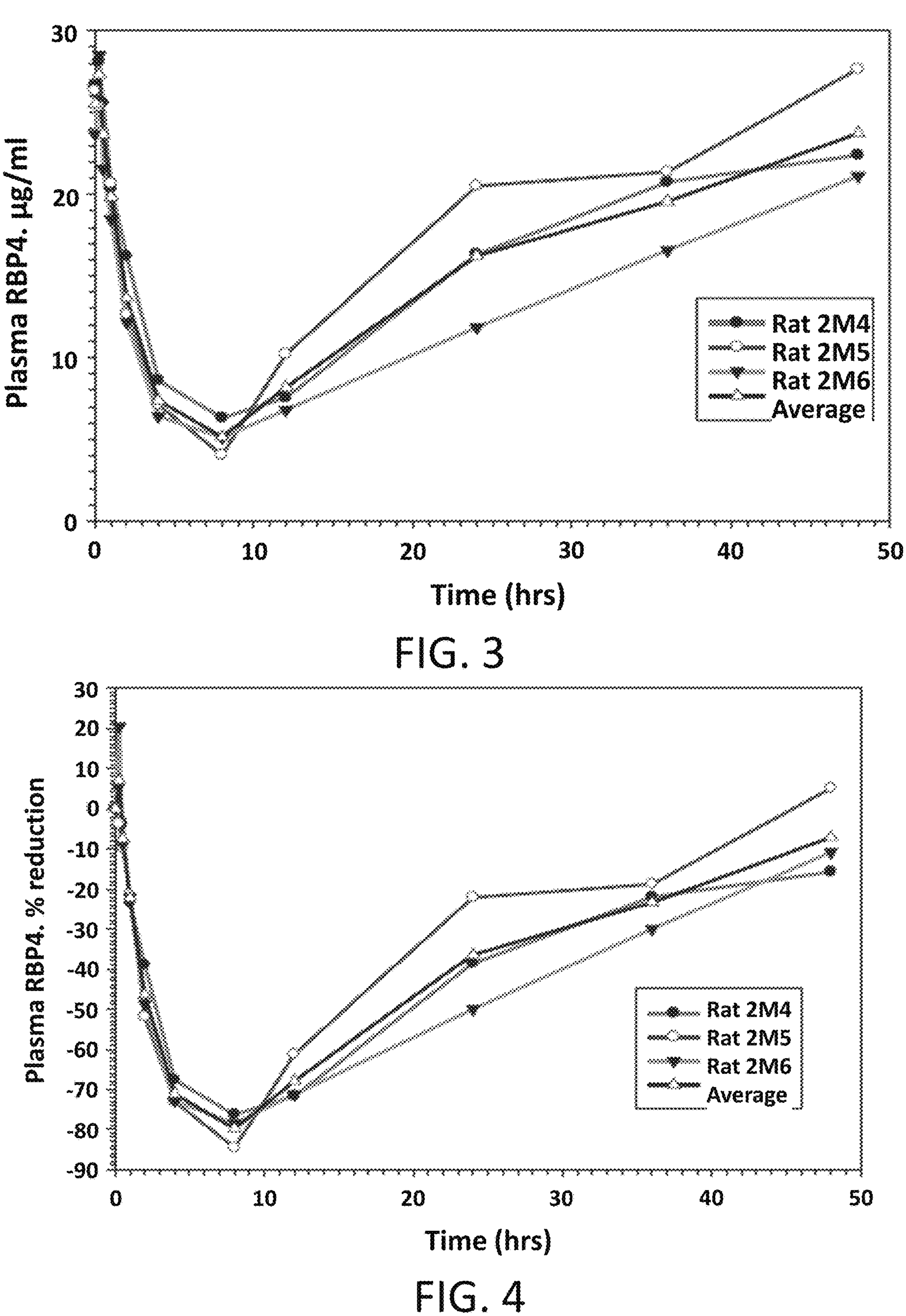
FIG. 3 illustrates absolute values of RBP4 plasma levels in male Sprague Dawley rats following a single oral dose of Compound 1 at 5 mg/kg.
FIG. 4 illustrates the percent reduction of RBP4 plasma levels compared to pre-dose levels in male Sprague Dawley rats following a single oral dose of Compound 1 at 5 mg/kg.
Figures 5, 6:
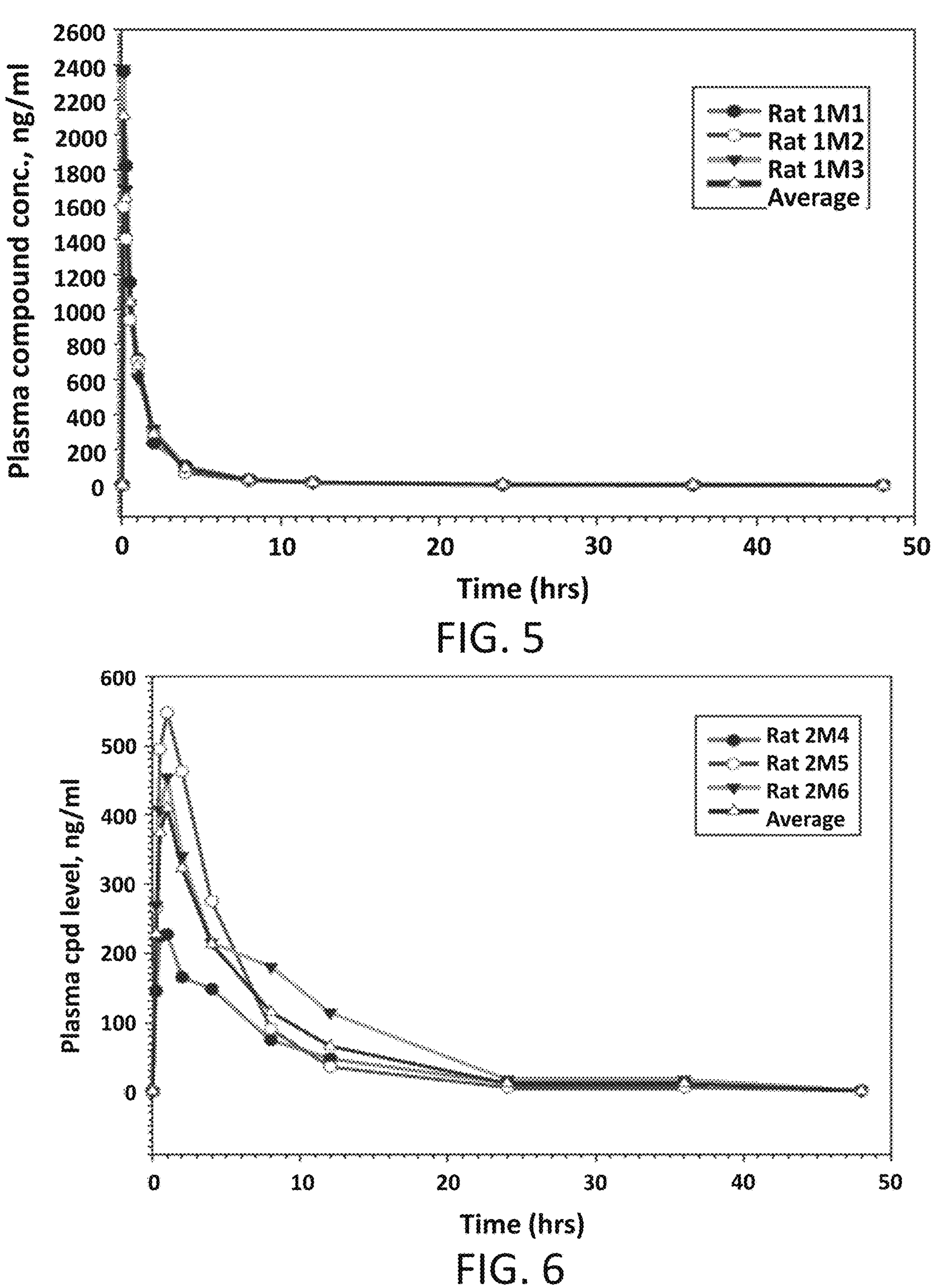
FIG. 5 illustrates Compound 1 plasma levels in male Sprague Dawley rats following a single intravenous dose of 2 mg/kg.
FIG. 6 illustrates Compound 1 plasma levels in male Sprague Dawley rats following a single oral dose of 5 mg/kg.
Figures 7, 8:
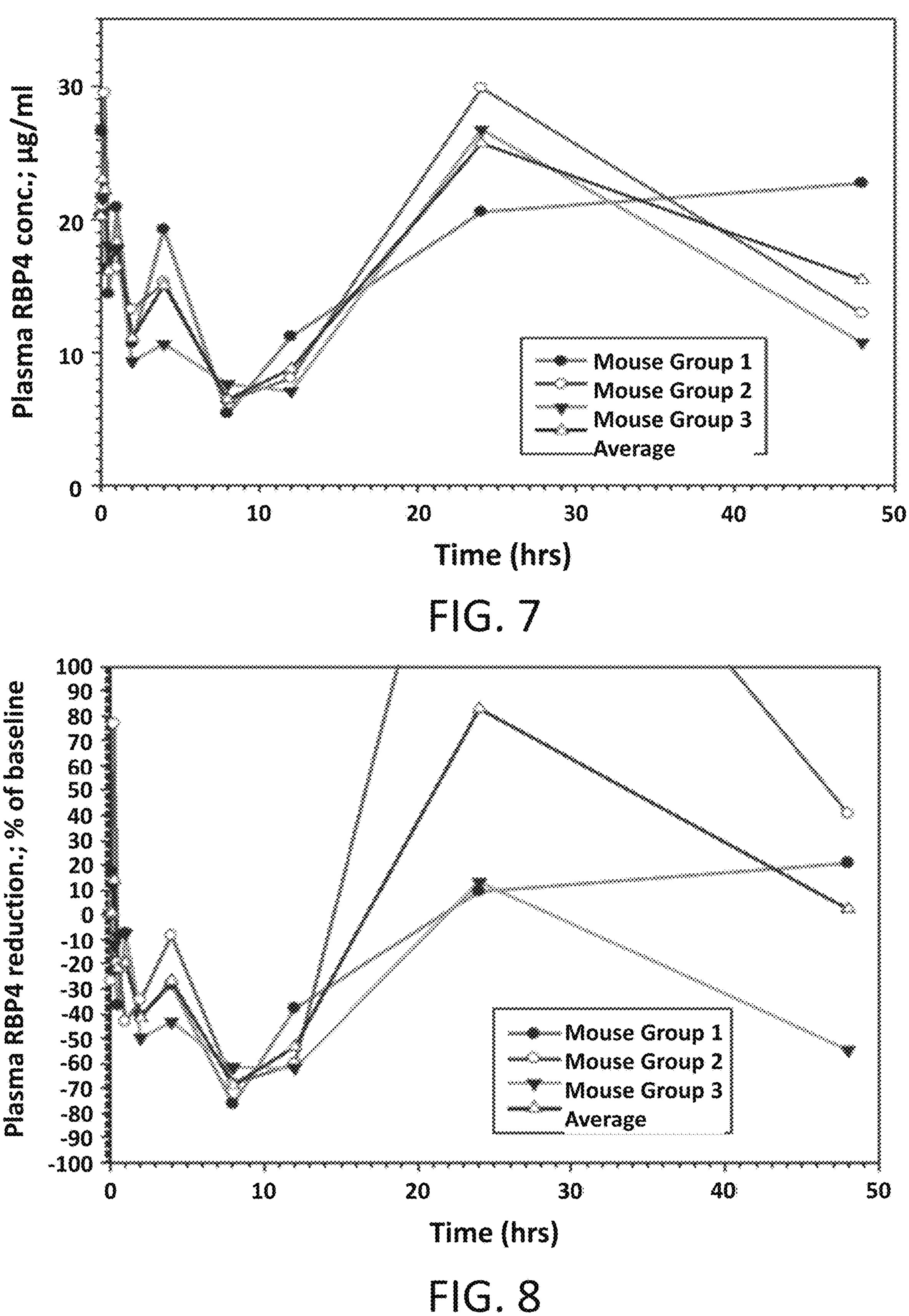
FIG. 7 illustrates absolute values of RBP4 plasma levels in male mice following a single intravenous dose of Compound 1 at 2 mg/kg.
FIG. 8 illustrates the percent reduction of RBP4 plasma levels compared to pre-dose levels in male mice following a single intravenous dose of Compound 1 at 2 mg/kg.
Figures 9, 10:
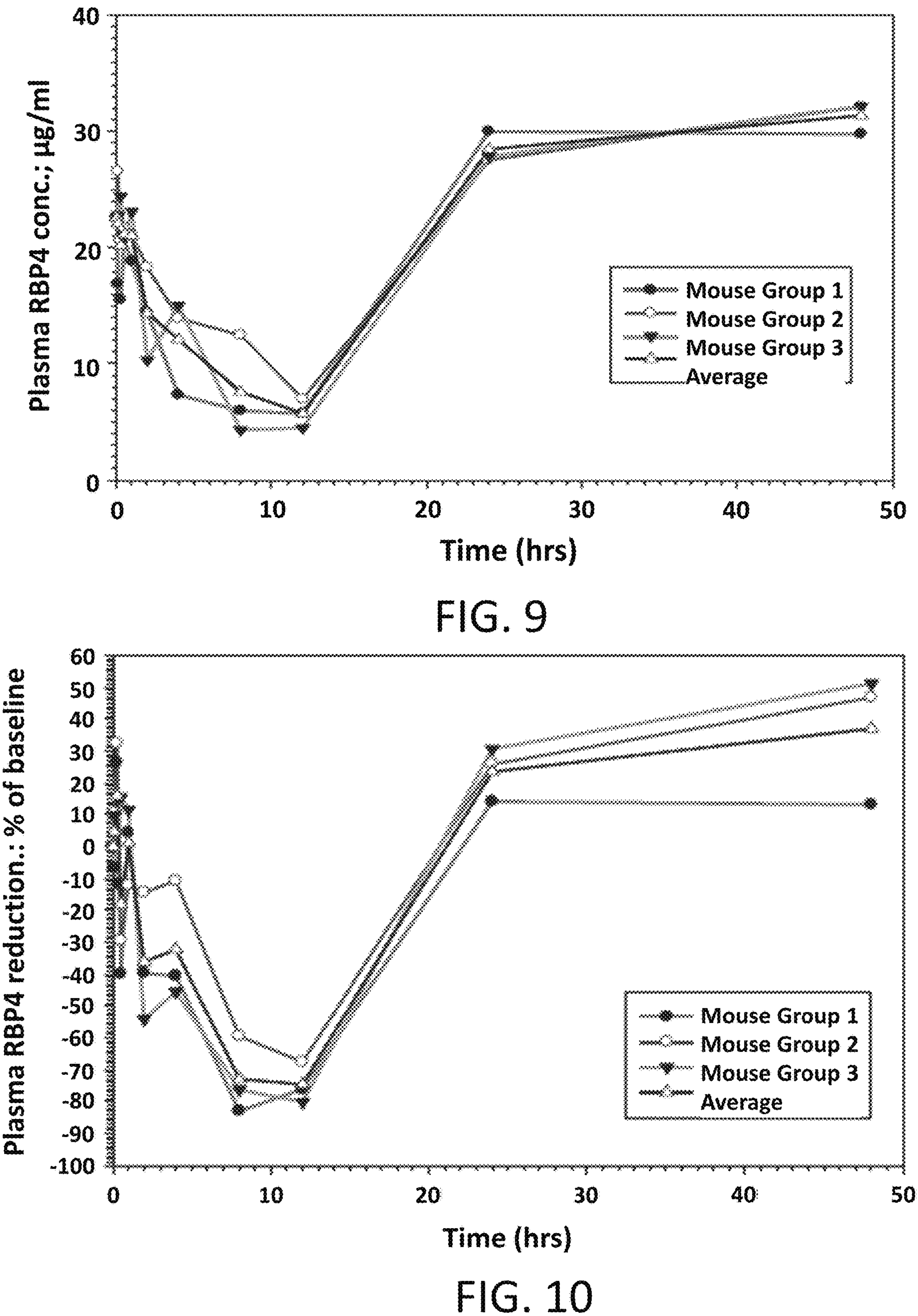
FIG. 9 illustrates absolute values of RBP4 plasma levels in male mice following a single oral dose of Compound 1 at 5 mg/kg.
FIG. 10 illustrates the percent reduction of RBP4 plasma levels compared to pre-dose levels in male mice following a single oral dose of Compound 1 at 5 mg/kg.
Figures 11, 12:
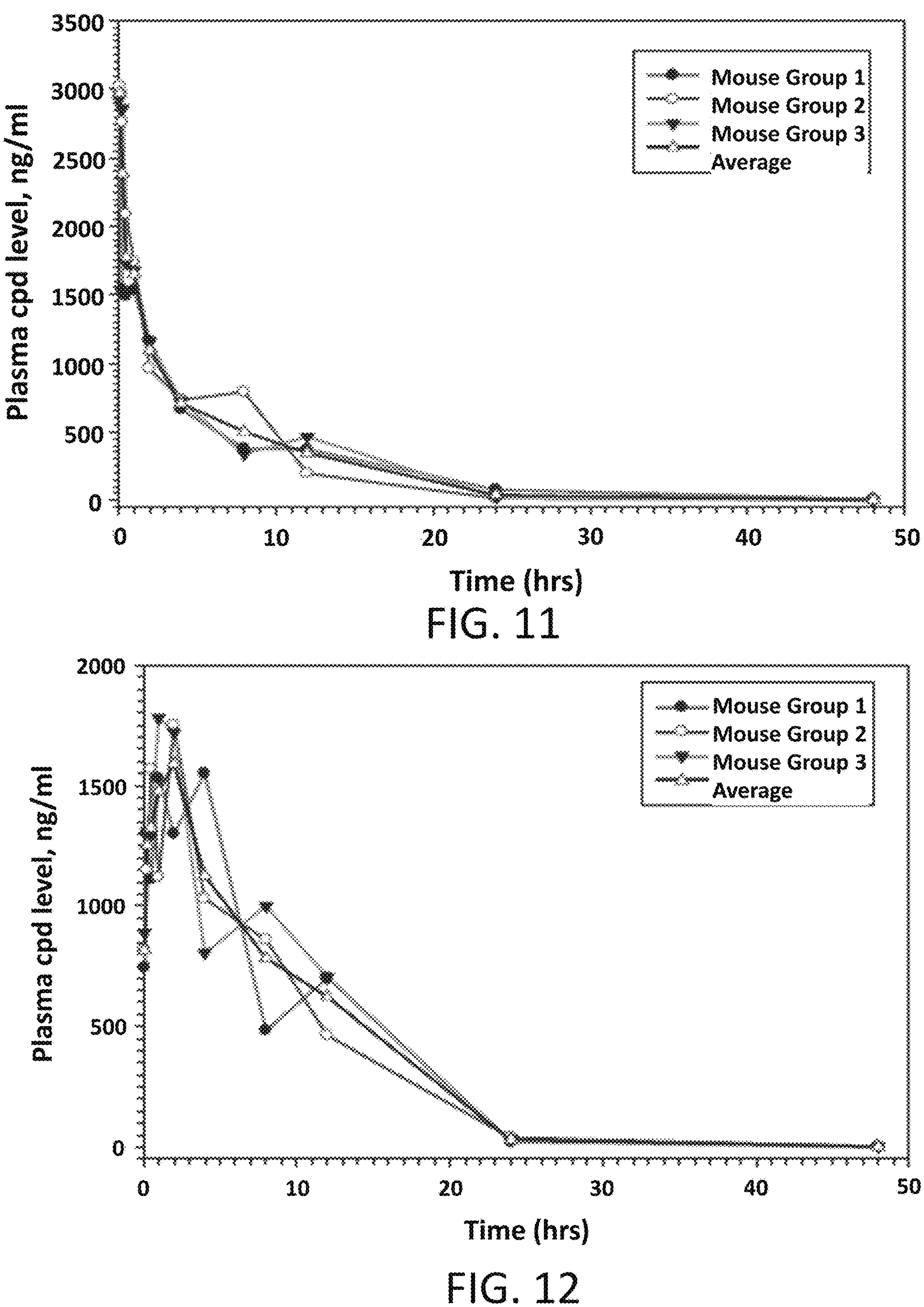
FIG. 11 illustrates Compound 1 plasma levels in male mice following a single intravenous dose of 2 mg/kg.
FIG. 12 illustrates Compound 1 plasma levels in male mice following a single oral dose of 5 mg/kg.
Figure 13:
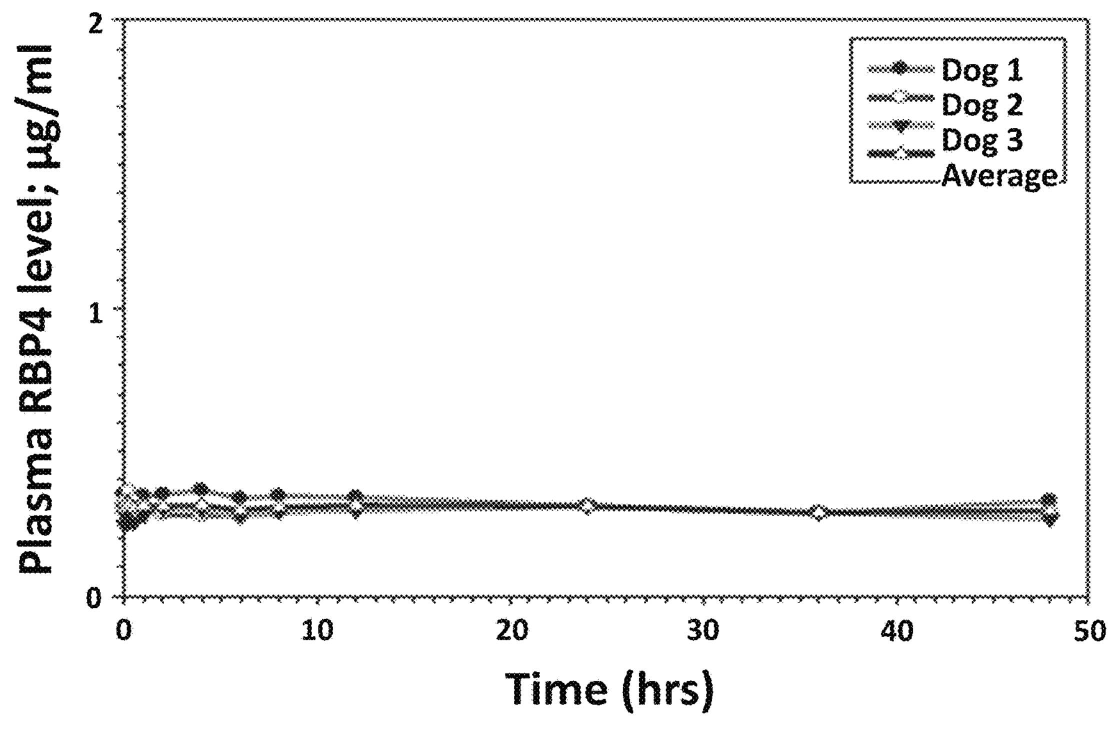
FIG. 13 illustrates absolute values of RBP4 plasma levels in male beagle dogs following a single intravenous dose of Compound 1 at 0.5 mg/kg.
Figure 14:
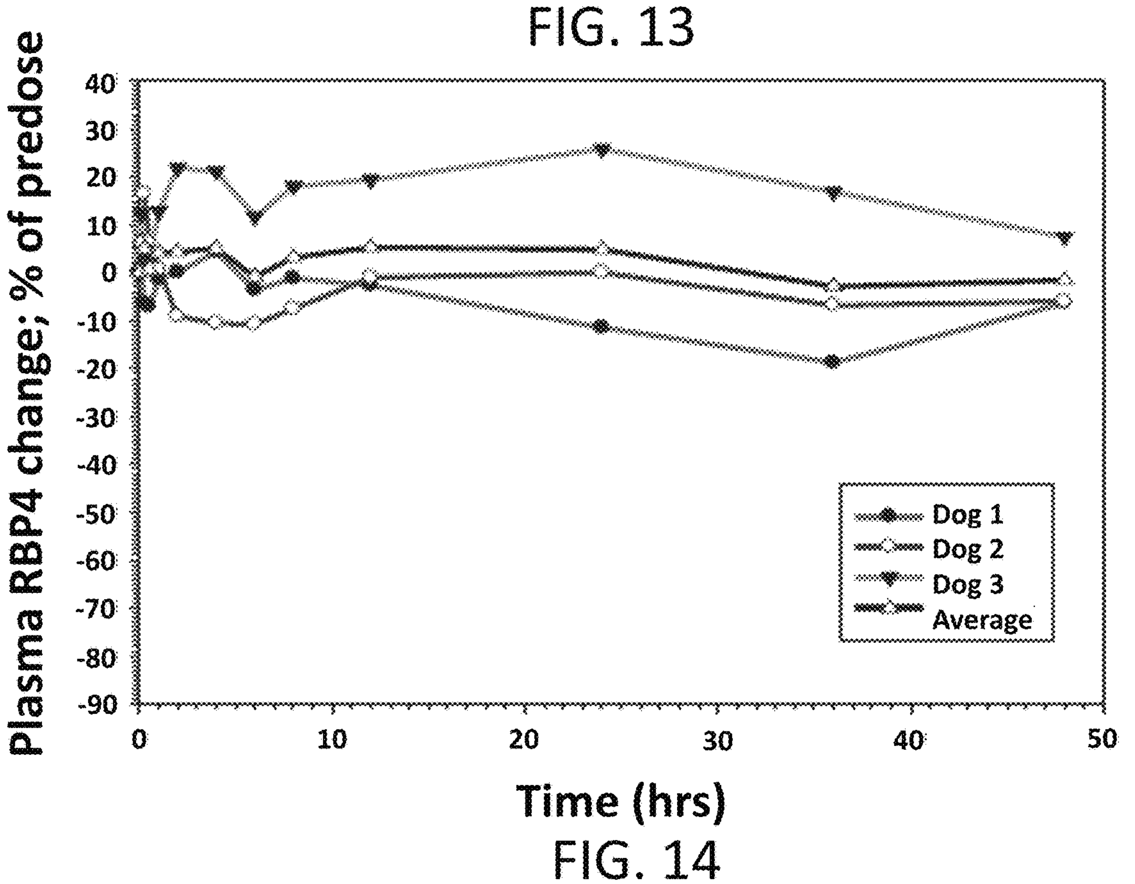
FIG. 14 illustrates the percent reduction of RBP4 plasma levels compared to pre-dose levels in male beagle dogs following a single intravenous dose of Compound 1 at 0.5 mg/kg.
Figure 15:
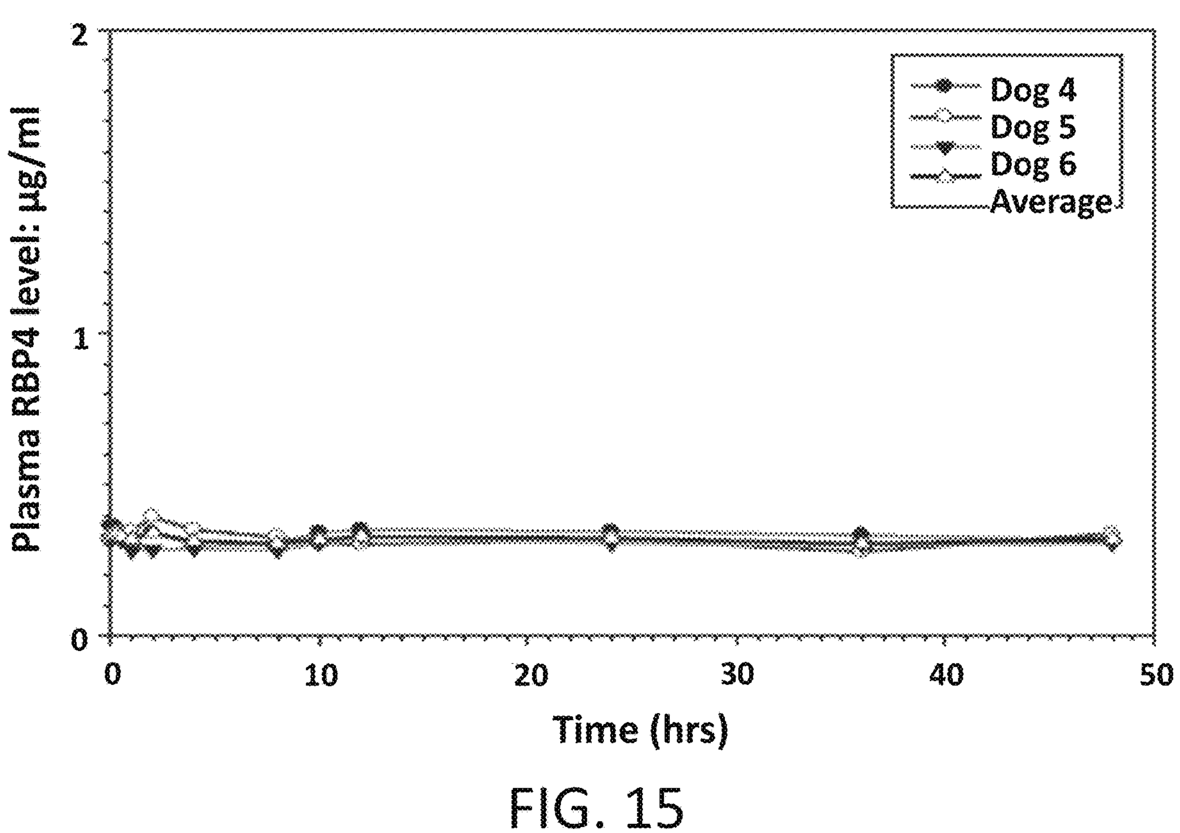
FIG. 15 illustrates absolute values of RBP4 plasma levels in male beagle dogs following a single oral dose of Compound 1 at 2 mg/kg.
Figure 16:
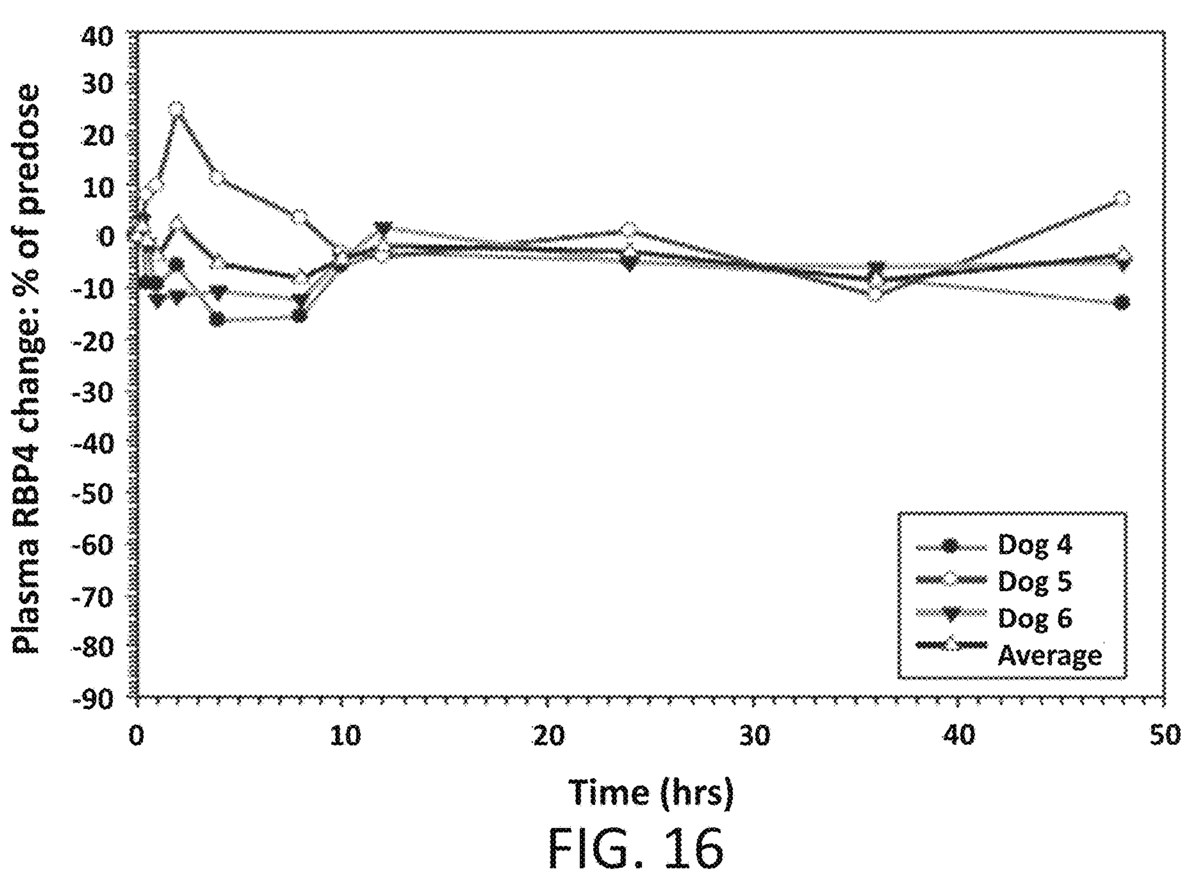
FIG. 16 illustrates the percent reduction of RBP4 plasma levels compared to pre-dose levels in male beagle dogs following a single oral dose of Compound 1 at 2 mg/kg.
Figure 17:
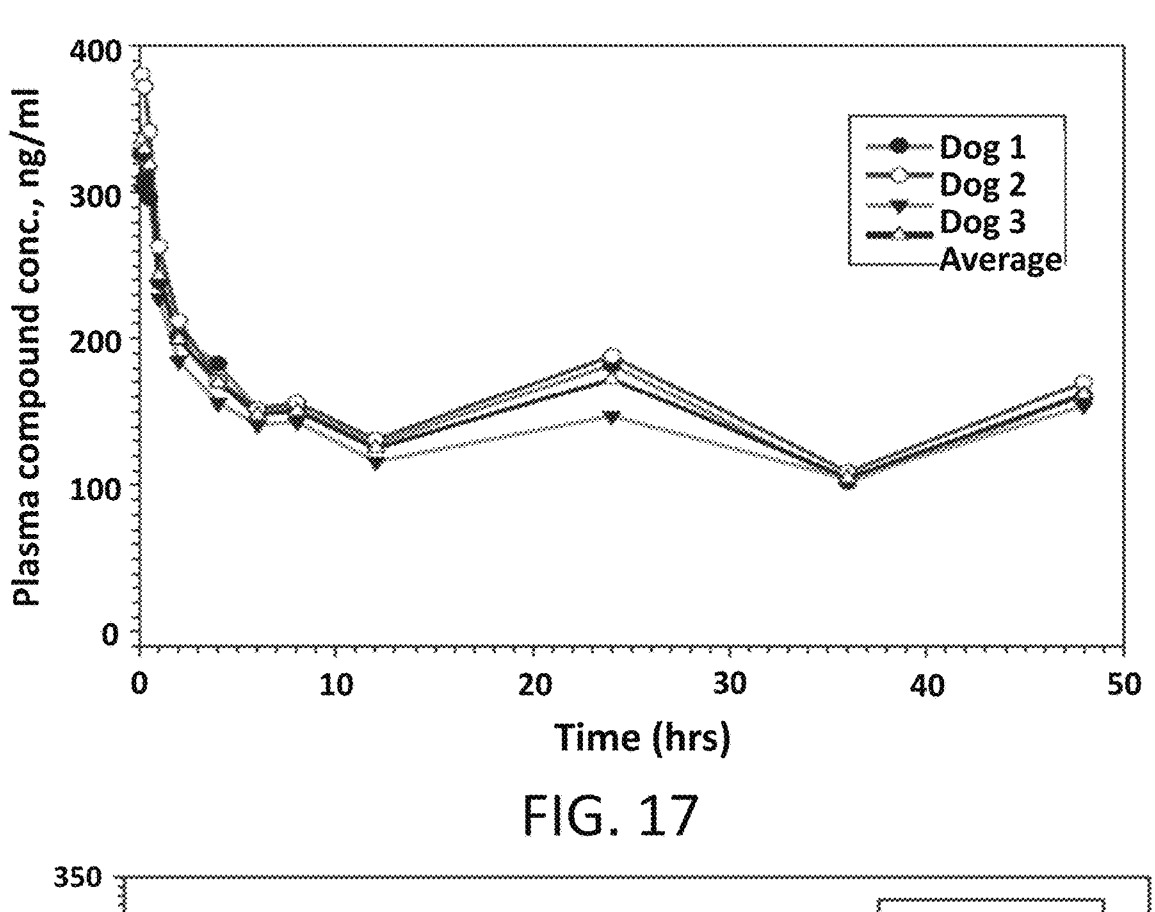
FIG. 17 illustrates Compound 1 plasma levels in male beagle dogs following a single intravenous dose of 0.5 mg/kg.
Figure 18:
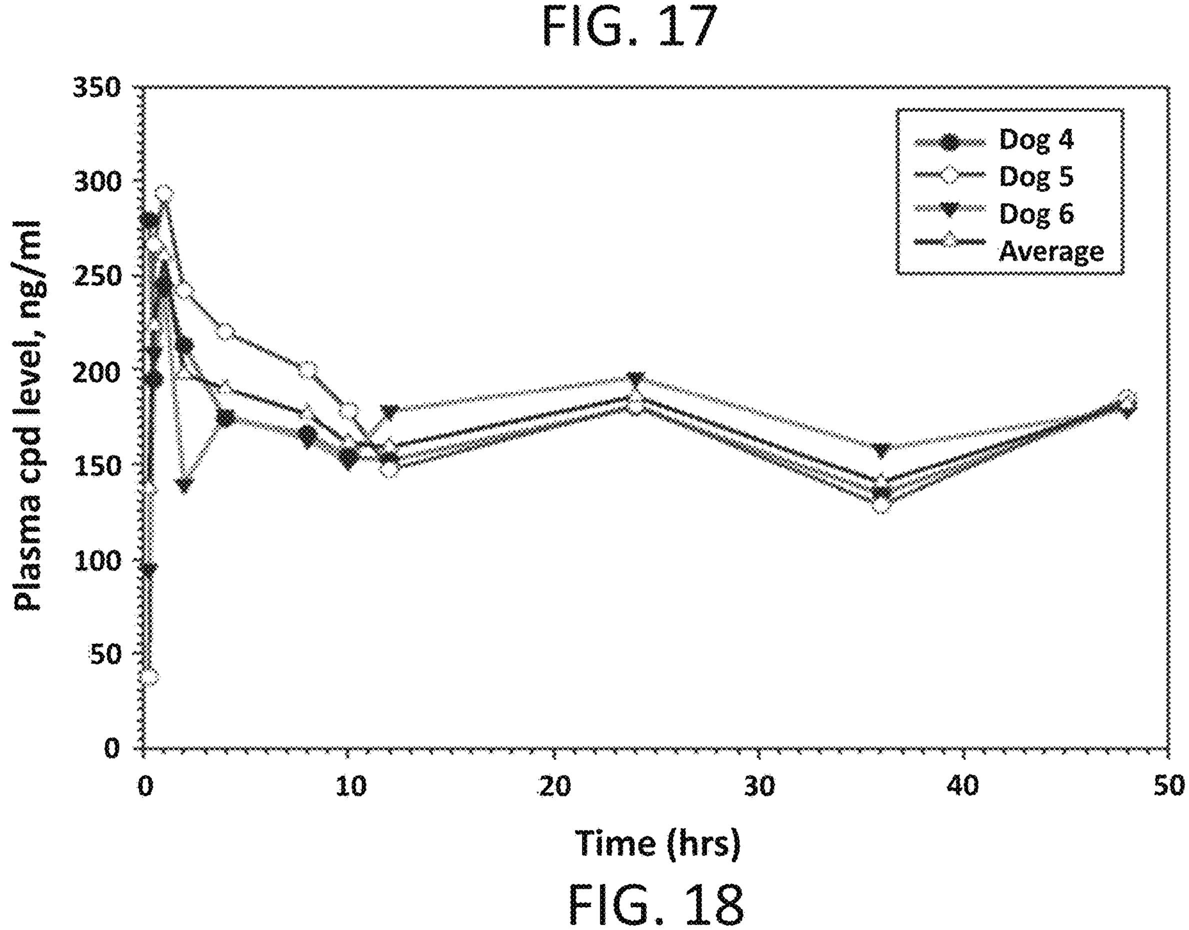
FIG. 18 illustrates Compound 1 plasma levels in male beagle dogs following a single oral dose of 2 mg/kg.
Figures 19, 20:
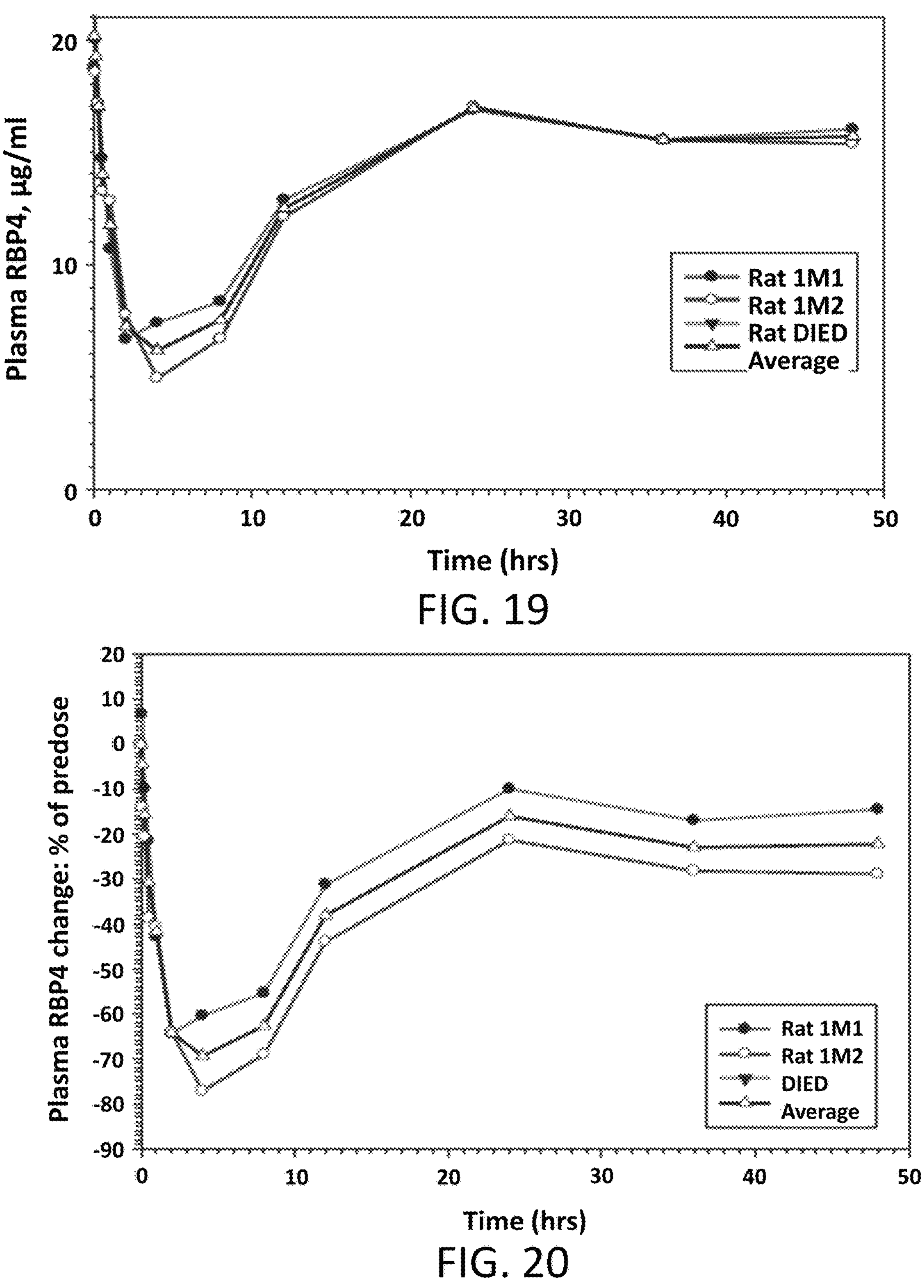
FIG. 19 illustrates absolute values of RBP4 plasma levels in male Sprague Dawley rats following a single intravenous dose of Compound 2 at 1 or 2 mg/kg. Rat 1M3 died at compound injection, and rat 1M1 was dosed at 1 mg/kg.
FIG. 20 illustrates the percent reduction of RBP4 plasma levels compared to pre-dose levels in male Sprague Dawley rats following a single intravenous dose of Compound 2 at 1 or 2 mg/kg.
Figure 21:
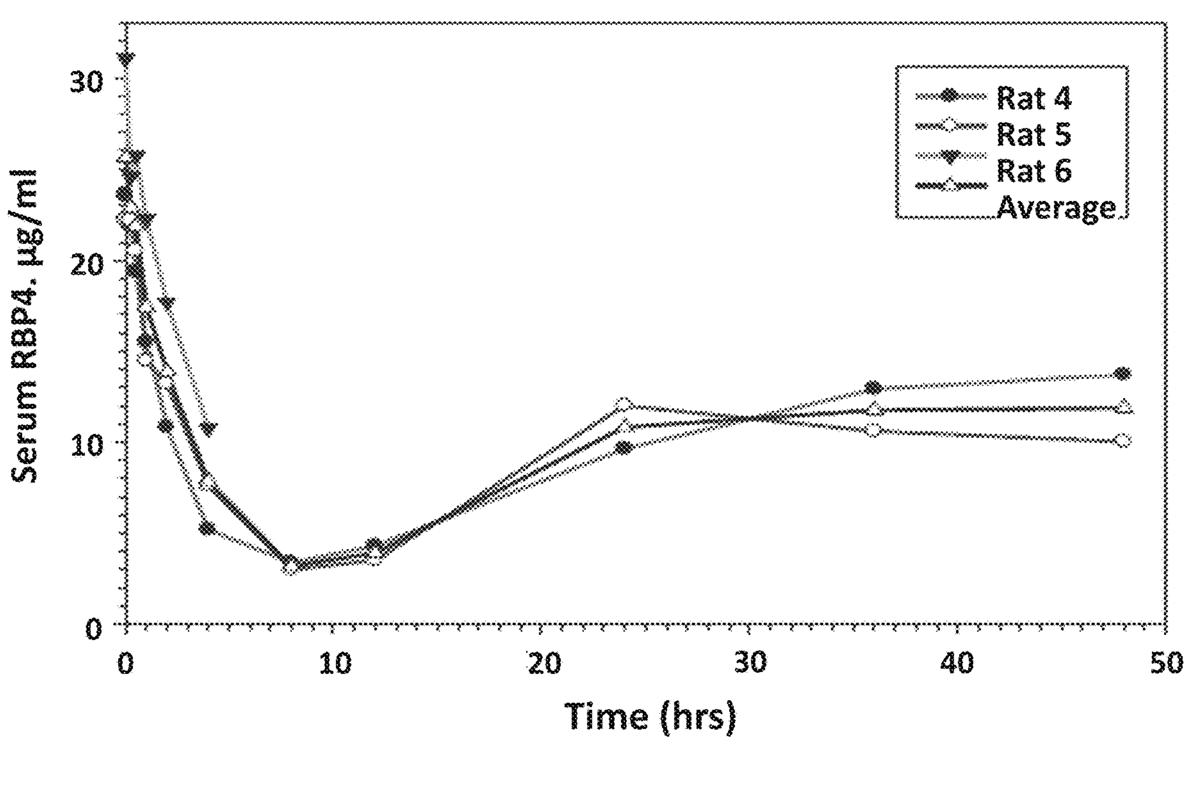
FIG. 21 illustrates absolute values of RBP4 serum levels in male Sprague Dawley rats following a single oral dose of Compound 2 at 5 mg/kg.
Figure 22:
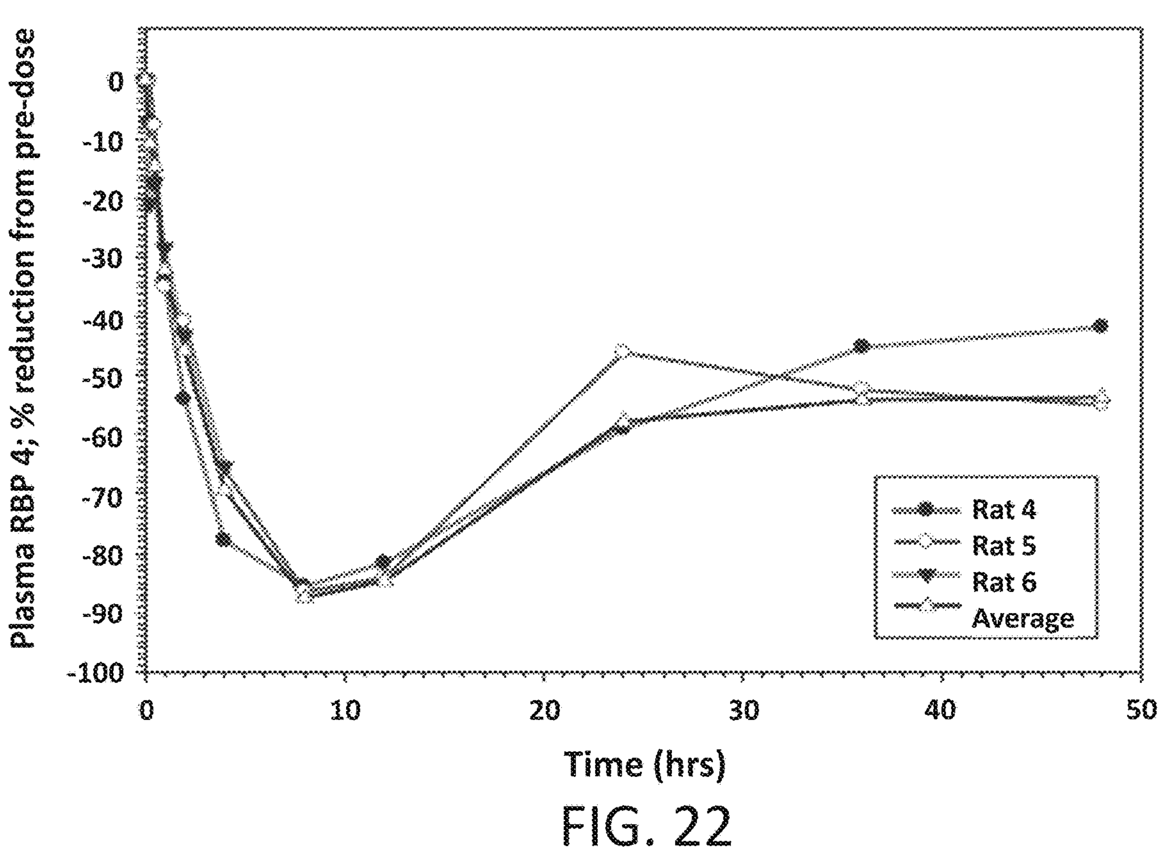
FIG. 22 illustrates the percent reduction of RBP4 plasma levels compared to pre-dose levels in male Sprague Dawley rats following a single oral dose of Compound 2 at 5 mg/kg.
Figure 23:
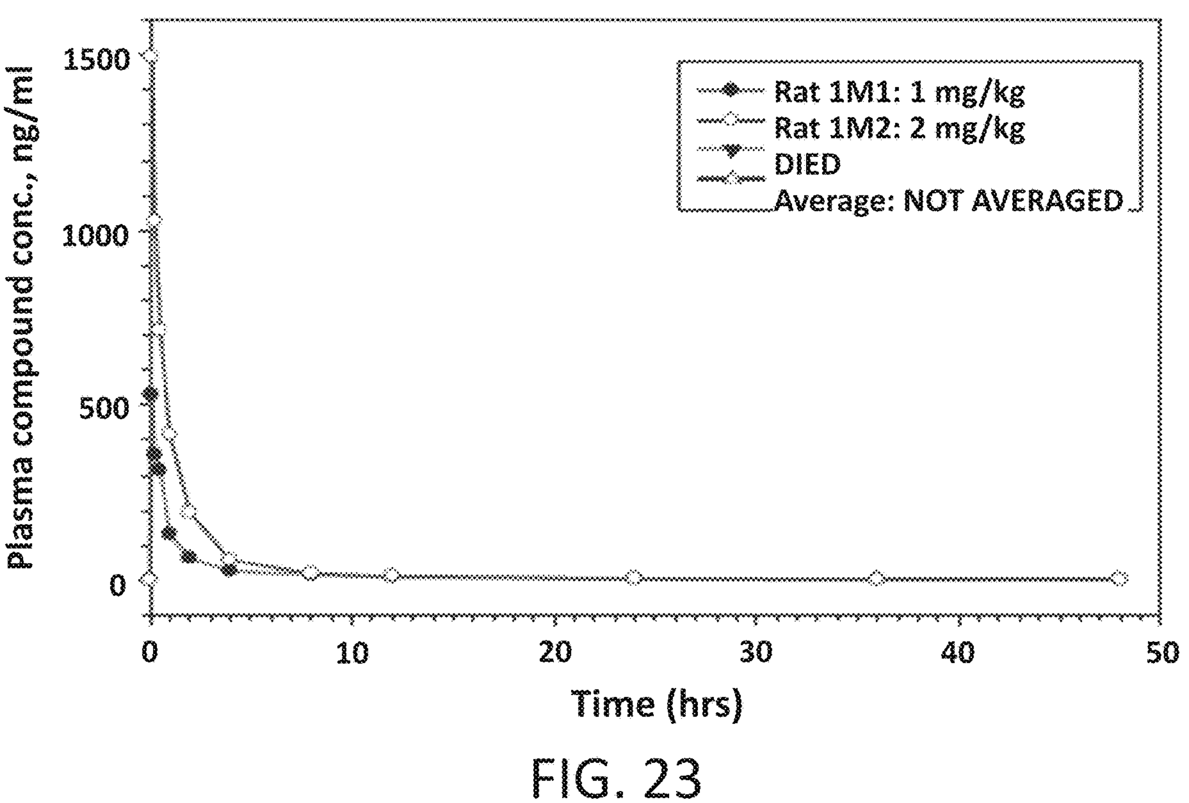
FIG. 23 illustrates Compound 2 plasma levels in male Sprague Dawley rats following a single intravenous dose of 1 or 2 mg/kg.
Figure 24:
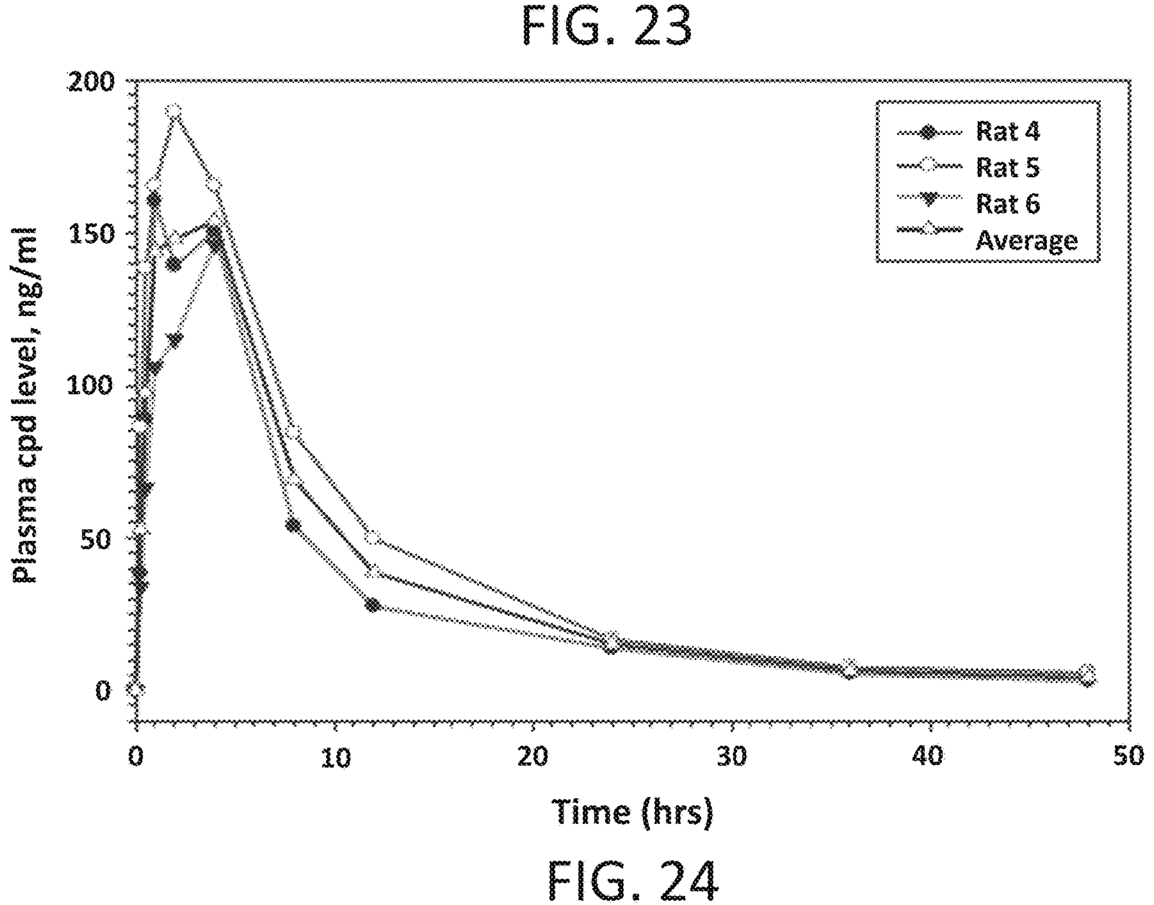
FIG. 24 illustrates Compound 2 plasma levels in male Sprague Dawley rats following a single oral dose of 5 mg/kg.
Figures 25, 26:
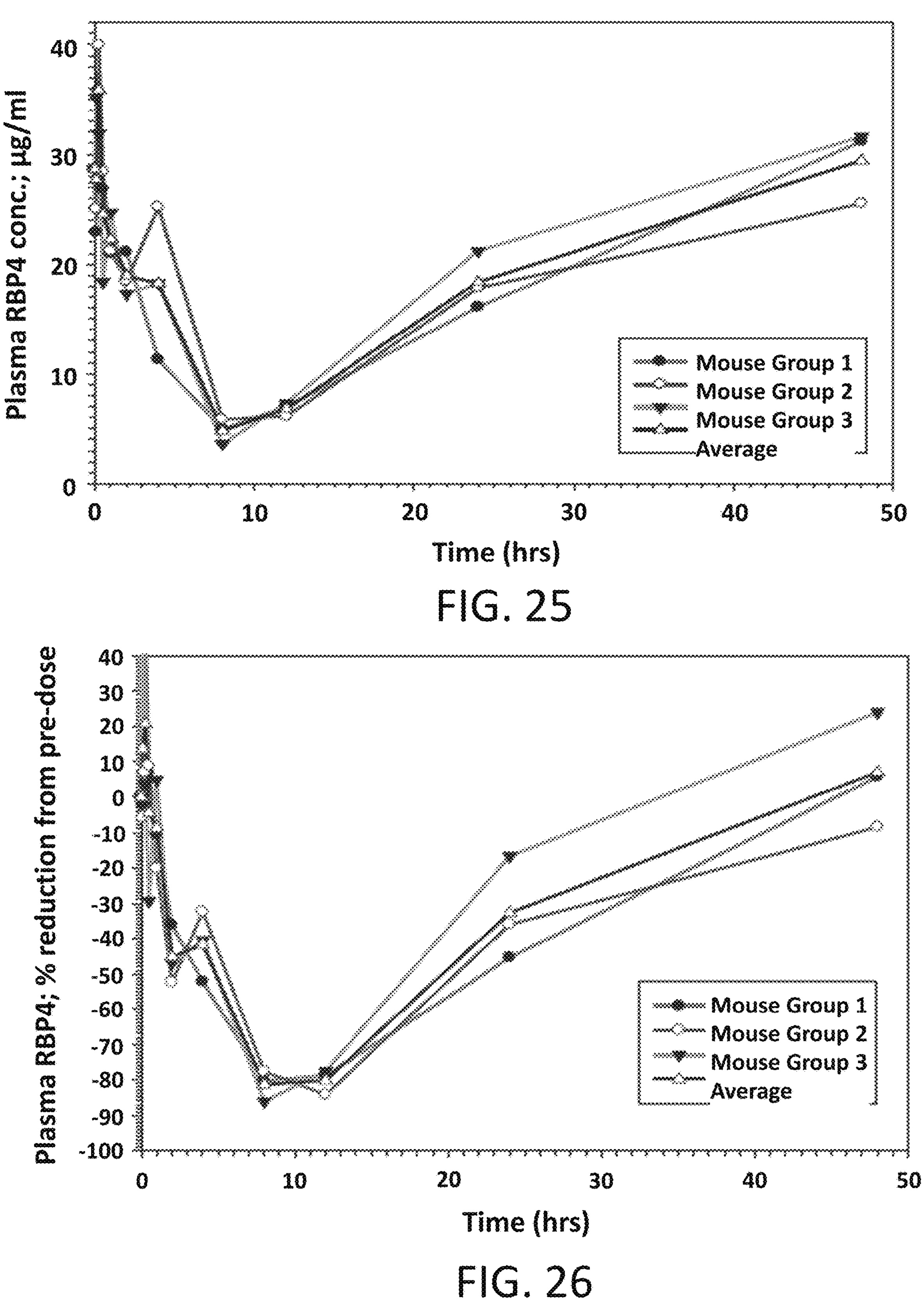
FIG. 25 illustrates absolute values of RBP4 plasma levels in male mice following a single intravenous dose of Compound 2 at 2 mg/kg.
FIG. 26 illustrates the percent reduction of RBP4 plasma levels compared to pre-dose levels in male mice following a single intravenous dose of Compound 2 at 2 mg/kg.
Figures 27, 28:
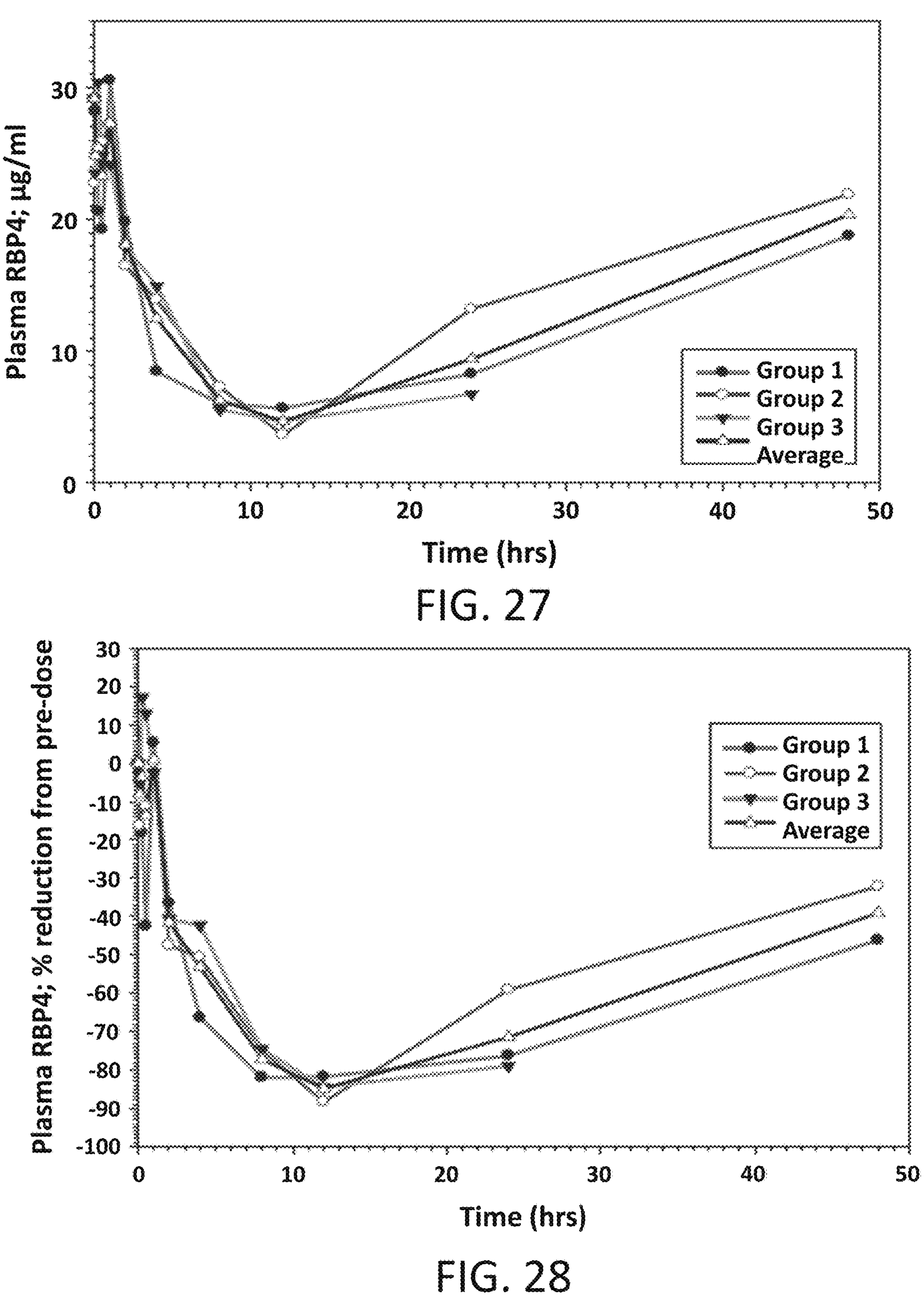
FIG. 27 illustrates absolute values of RBP4 plasma levels in male mice following a single oral dose of Compound 2 at 5 mg/kg.
FIG. 28 illustrates the percent reduction of RBP4 plasma levels compared to pre-dose levels in male mice following a single oral dose of Compound 2 at 5 mg/kg.
Figures 29, 30:
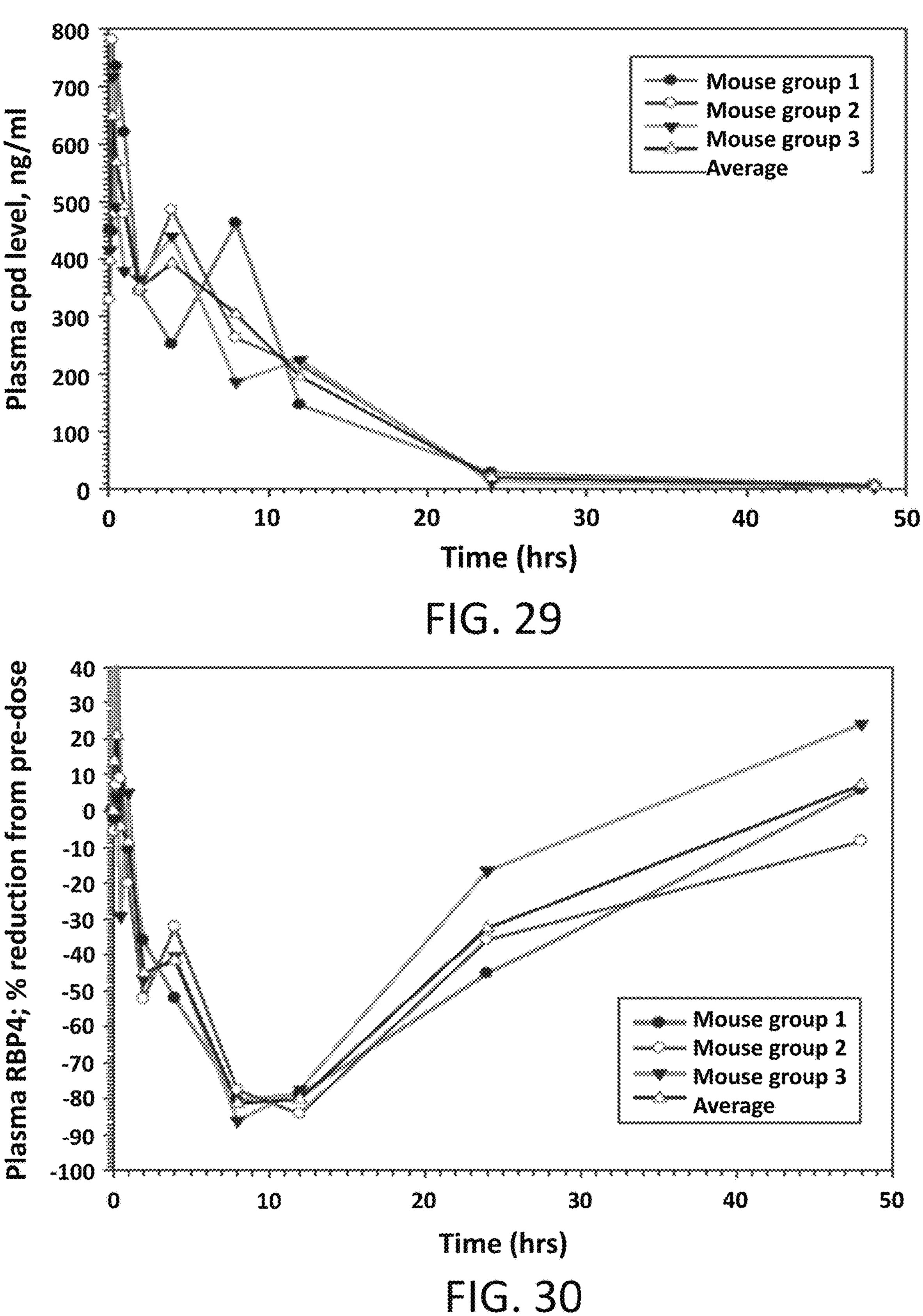
FIG. 29 illustrates Compound 2 plasma levels in male mice following a single intravenous dose of 2 mg/kg.
FIG. 30 illustrates the percent reduction of RBP4 plasma levels compared to pre-dose levels in male mice following a single intravenous dose of Compound 2 at 2 mg/kg.
Figure 31:
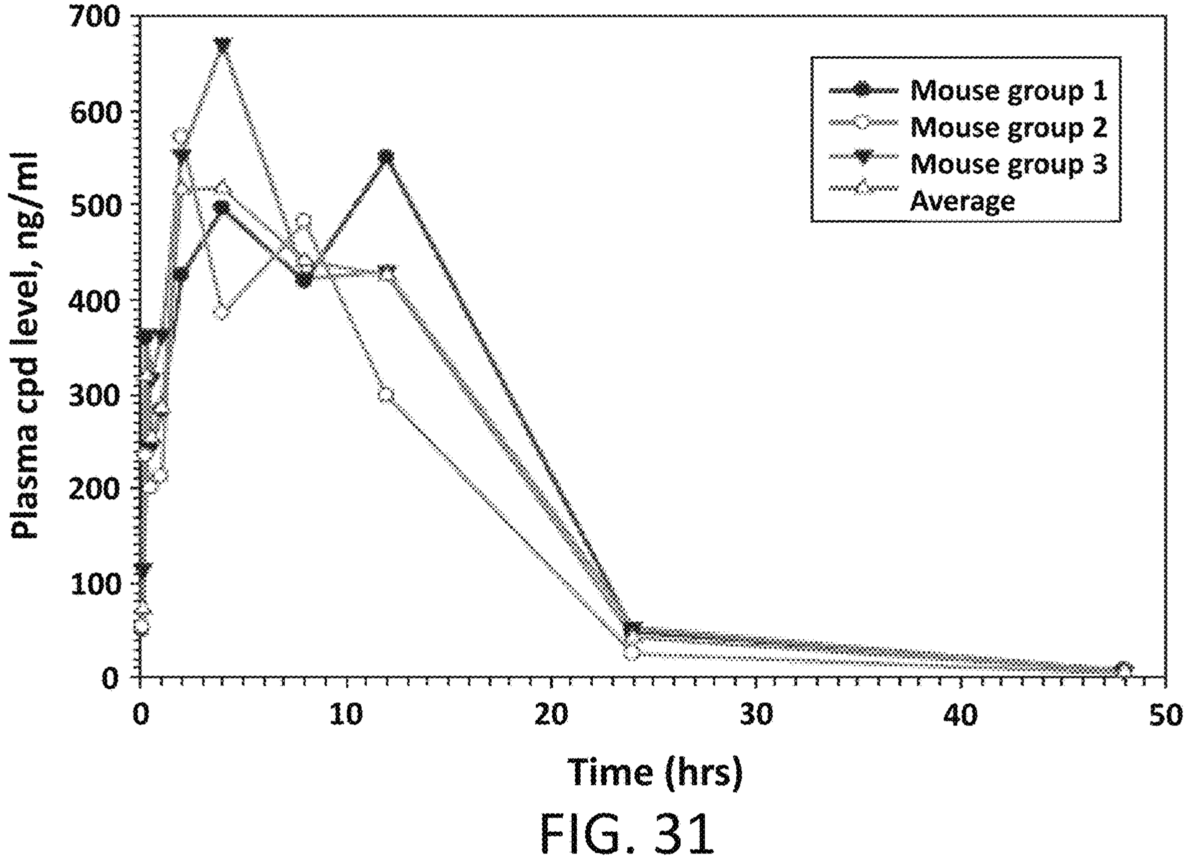
FIG. 31 illustrates Compound 2 plasma levels in male mice following a single oral dose of 5 mg/kg.
Figure 32A:
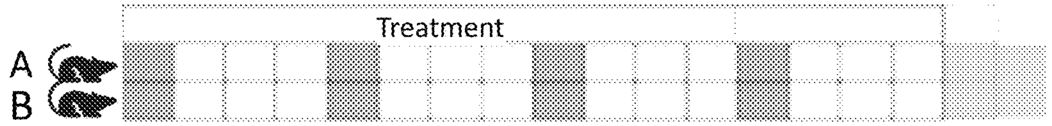
FIG. 32A illustrates a preventative dosing schedule wherein Compound 2 treatment is initiated at the same time as a western high fat diet (HFD).
Figure 32B:
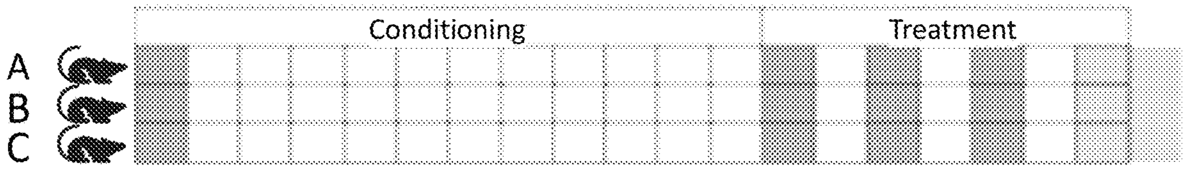
FIG. 32B illustrates a treatment dosing schedule wherein Compound 2 or obeticholic acid (OCA) treatment is initiated after a conditioning period on a western high fat diet (HFD).
Figure 33A:
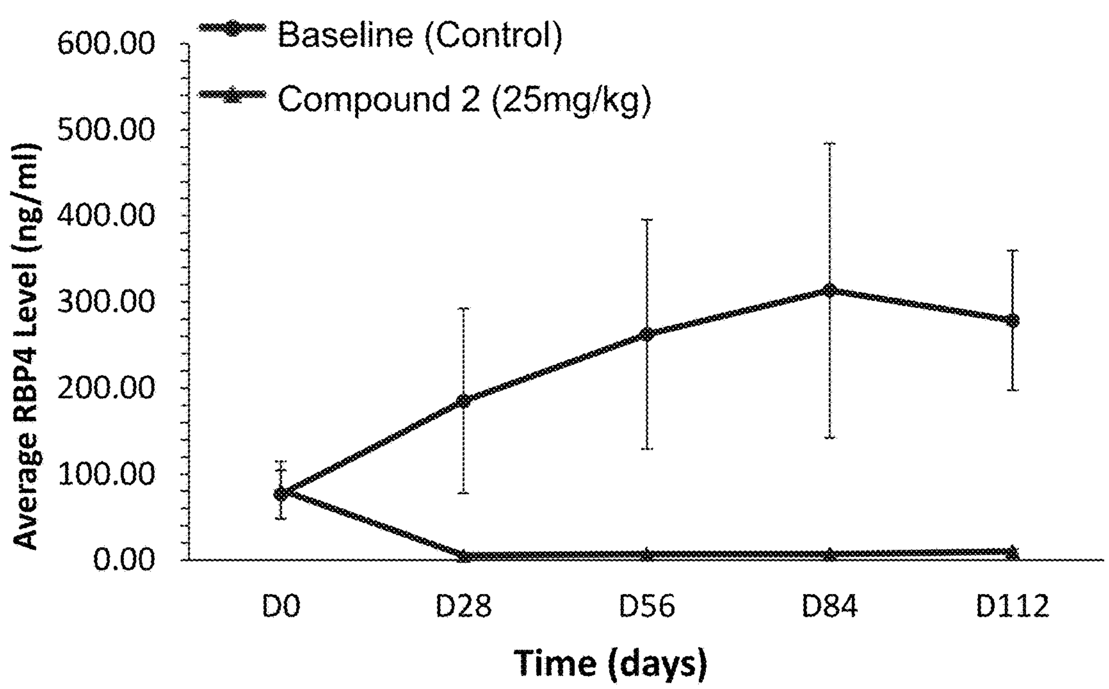
FIG. 33A illustrates RBP4 plasma levels in ob/ob mice following a preventative dosing schedule with Compound 2 at 25 mg/kg.
Figure 33B:
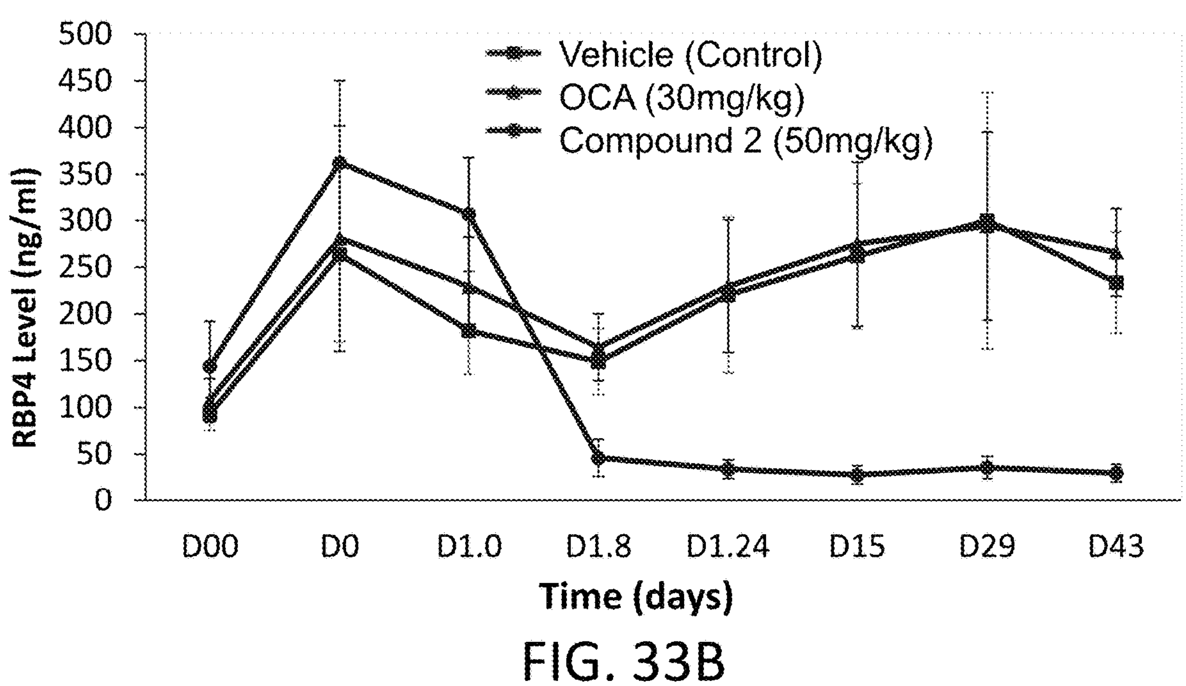
FIG. 33B illustrates RBP4 plasma levels in ob/ob mice following a treatment (after conditioning on a western high fat diet) dosing schedule with Compound 2 (50 mg/kg) or obeticholic acid (OCA, 30 mg/kg).
Figure 34A:
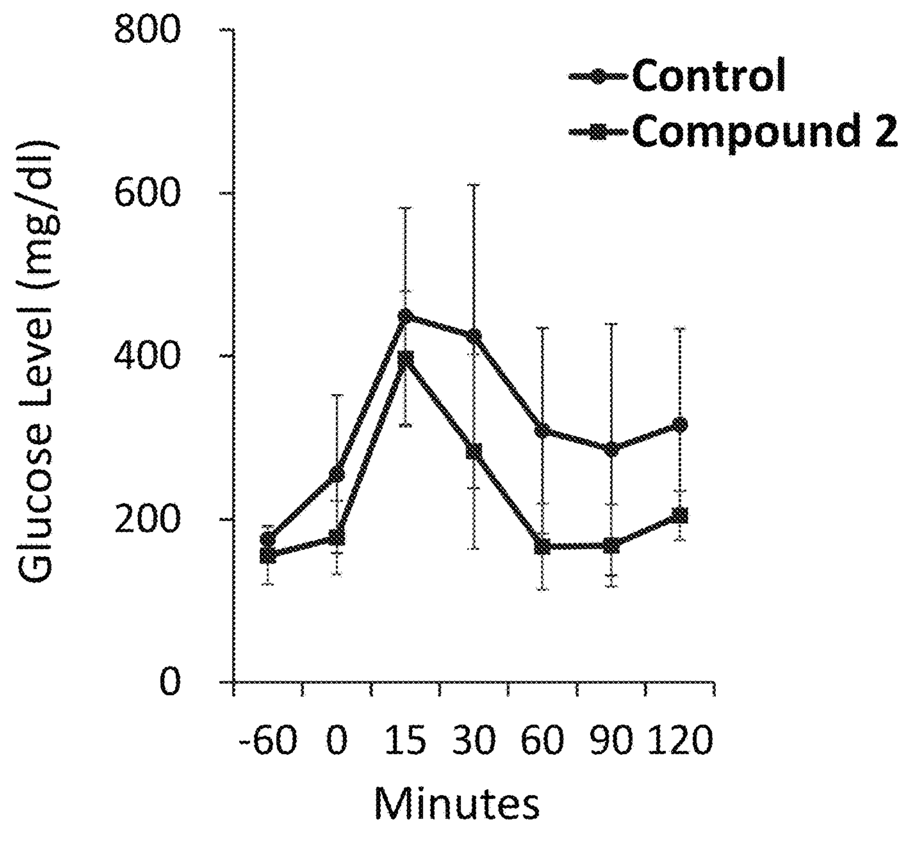
FIG. 34A illustrates glucose levels in ob/ob mice following a preventative dosing schedule with Compound 2.
Figure 34B:
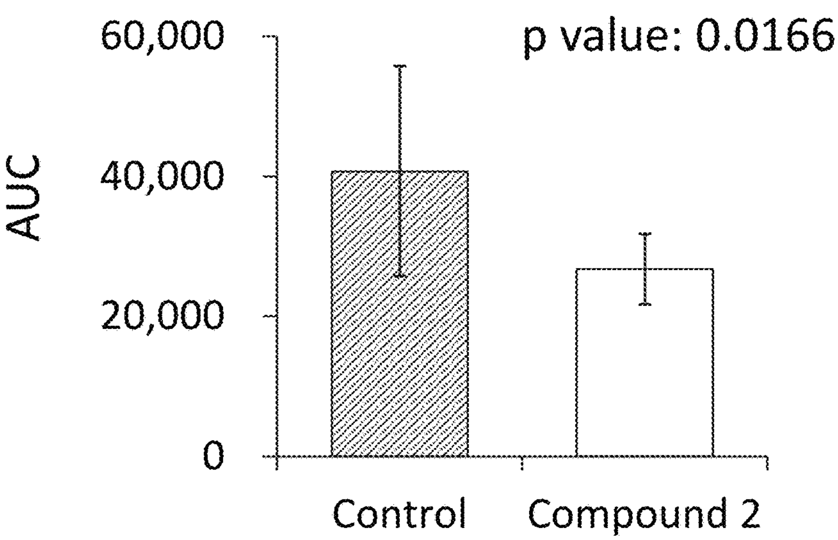
FIG. 34B illustrates area under curve glucose levels in ob/ob mice following a preventative dosing schedule with Compound 2.
Figure 35A:
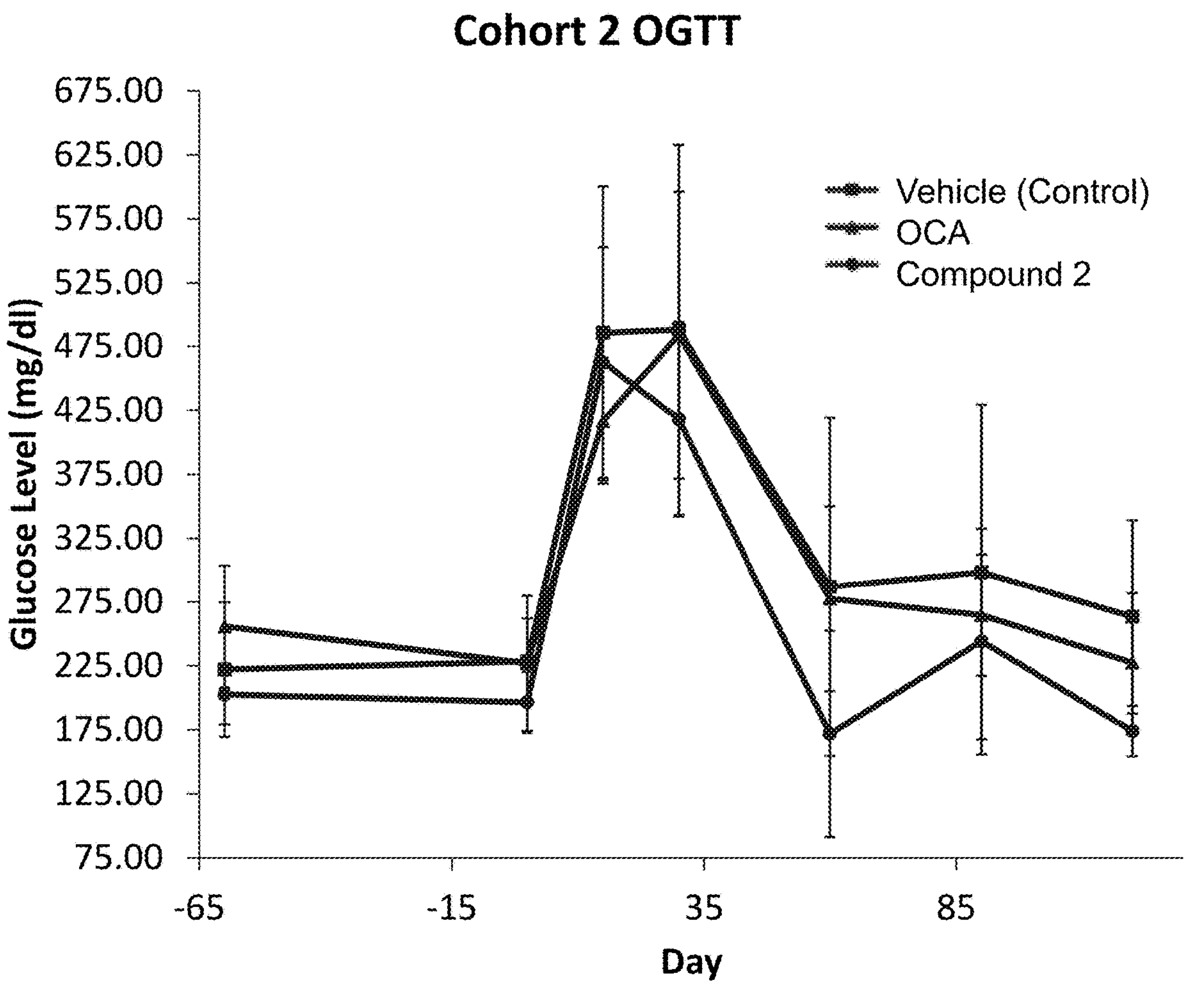
FIG. 35A illustrates glucose levels in ob/ob mice following a treatment (after conditioning on a western high fat diet) dosing schedule with Compound 2 or obeticholic acid (OCA).
Figure 35B:
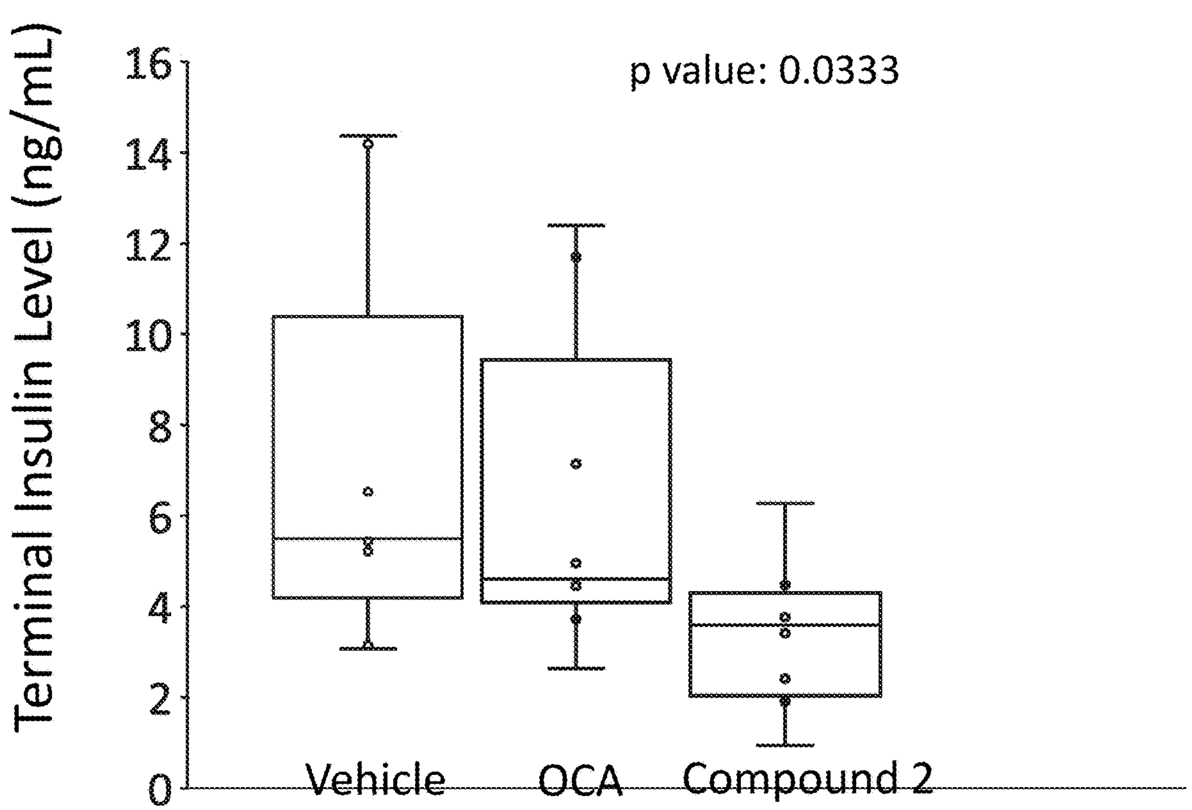
FIG. 35B illustrates terminal insulin levels in ob/ob mice following a treatment (after conditioning on a western high fat diet) dosing schedule with Compound 2 or obeticholic acid (OCA).

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the $—NH_2$ radical.

"Cyano" refers to the —CN radical.

"Nitro" refers to the $—NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Hydrazino" refers to the $=N—NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$SO_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N$(R^a)_2$, —N($R^a$)C(O)O$R^a$, —OC(O)—N$(R^a)_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N$(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises five to eight carbon atoms (e.g., $C_5$-$C_8$alkenylene). In other embodiments, an alkenylene comprises two to five carbon atoms (e.g., $C_2$-$C_5$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N$(R^a)_2$, —N($R^a$)C(O)O$R^a$, —OC(O)—N$(R^a)_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N$(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N$(R^a)_2$, —N($R^a$)C(O)O$R^a$, —OC(O)—N$(R^a)_2$, —N($R^a$)C(O)$R^a$, —N($R^a$)S(O)$_t$$R^a$ (where t is 1 or 2), —SO$_t$O$R^a$ (where t is 1 or 2), —S(O)$_t$$R^a$ (where t is 1 or 2) and —S(O)$_t$N$(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $-R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $-R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula $-O-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula $-R^c$-carbocyclyl where $R^c$ is an alkylene chain as defined above. The alkylene chain and the carbocyclyl radical are optionally substituted as defined above.

"Carbocyclylalkynyl" refers to a radical of the formula —R-carbocyclyl where $R^c$ is an alkynylene chain as defined above. The alkynylene chain and the carbocyclyl radical are optionally substituted as defined above.

"Carbocyclylalkoxy" refers to a radical bonded through an oxygen atom of the formula $-O-R^c$-carbocyclyl where $R^c$ is an alkylene chain as defined above. The alkylene chain and the carbocyclyl radical are optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

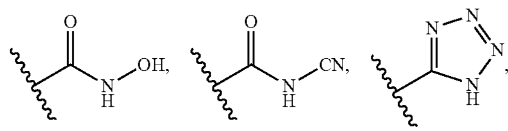

-continued

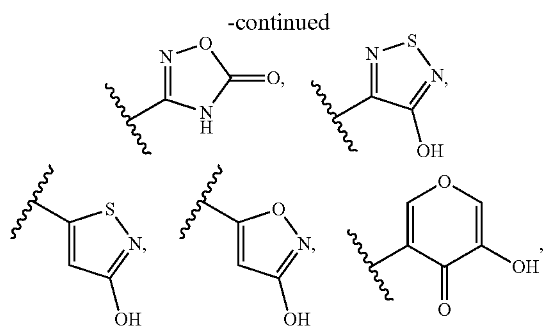

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $—R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $—O—R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s).

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula $—R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula $—O—R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

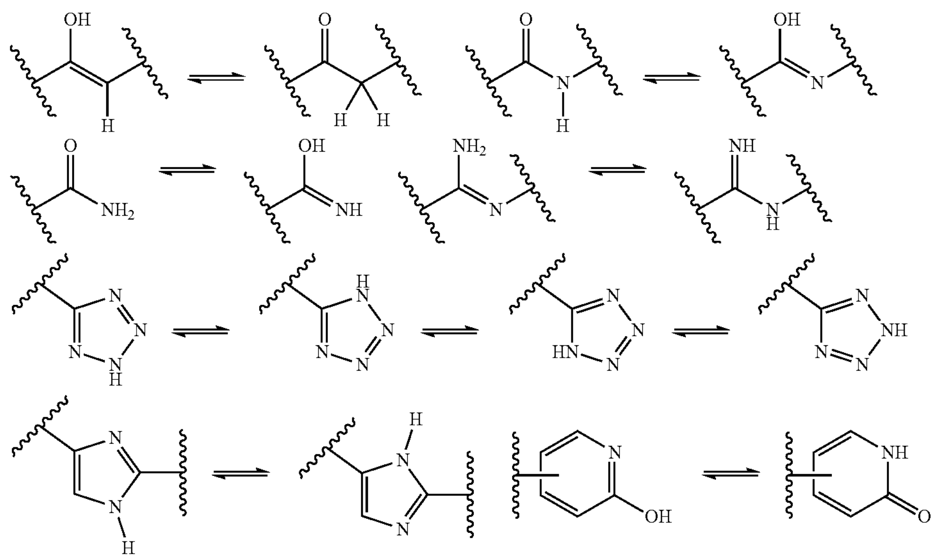

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

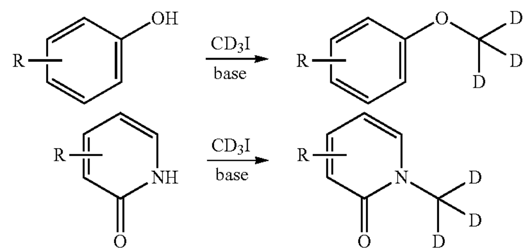

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

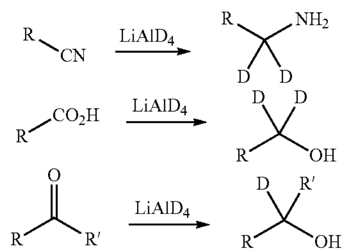

Deuterium gas and palladium catalyst are employed to reduce unsaturated carbon-carbon linkages and to perform a reductive substitution of aryl carbon-halogen bonds as illustrated, by way of example only, in the reaction schemes below.

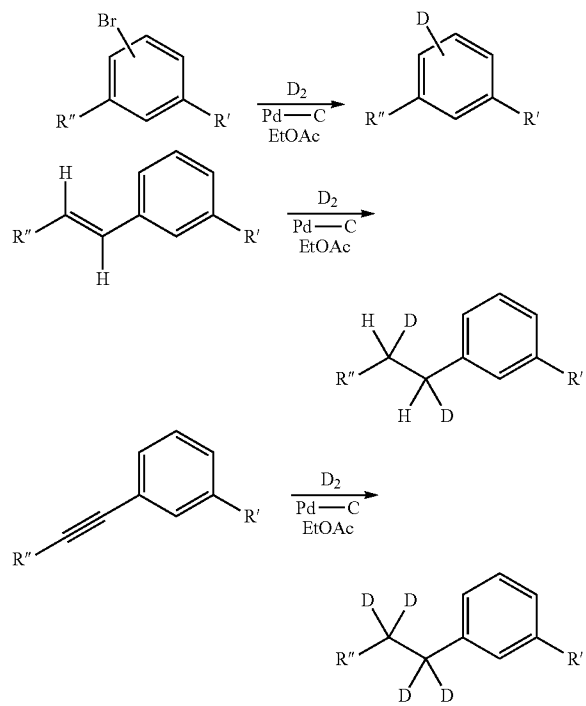

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the heterocyclic RBP4 inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berg S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

RBP4 Inhibitory Compounds

Provided herein in some embodiments are RBP4 inhibitory compounds and pharmaceutical compositions comprising said compounds. The subject compounds and compositions are useful for inhibiting RPB4 and for the treatment of metabolic diseases or disorders, such as NASH, NAFLD, type II diabetes, diabetic retinopathy, obesity, fibrosis, cirrhosis, or hepatocellular carcinoma.

Some embodiments provided herein describe a compound, or a pharmaceutically acceptable salt, solvate, polymorph, prodrug, metabolite, N-oxide, stereoisomer, or isomer thereof, for use in treating a metabolic disease or disorder, having the structure of Formula (I):

Formula (I)

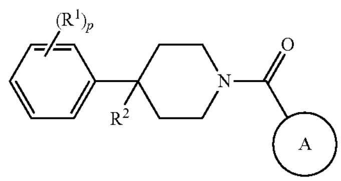

wherein:

each $R^1$ is independently halogen, optionally substituted alkyl, optionally substituted cycloalkyl, optionally substituted heterocyclyl, optionally substituted heterocyclalkyl, —$COR^7$, —$CON(R^7)_2$, optionally substituted ($C_0$-$C_4$ alkylene)-CN, optionally substituted ($C_0$-$C_4$ alkylene)-$OR^7$, optionally substituted ($C_0$-$C_4$ alkylene)-$N(R')_2$, optionally substituted ($C_0$-$C_4$ alkylene)$N(R^8)$—$COR^7$, optionally substituted ($C_0$-$C_4$ alkylene)-$SO_2N(R^7)_2$, optionally substituted ($C_0$-$C_4$ alkylene)-$SO_2R^7$, optionally substituted ($C_0$-$C_4$ alkylene)$N(R^8)$—$SO_2N(R^7)_2$, or optionally substituted ($C_0$-$C_4$ alkylene)$N(R^8)$—$SO_2R^7$;

each $R^7$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^8$ is independently selected from H or optionally substituted alkyl;

$R^2$ is —H, —OH, optionally substituted alkyl, or halogen;

p is 0, 1, 2, 3, 4, or 5,

A has the structure:

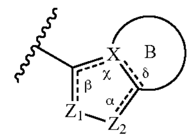

wherein:

α, β, χ, and δ are each independently absent or present, and when present each is a bond;

X is N;

$Z_1$ is S, O, or N;

$Z_2$ is S, O, N, or $NR^3$;

$R^3$ is H, optionally substituted alkyl, or oxetane; and

B is a substituted or unsubstituted fused 5-, 6-, or 7-membered ring structure.

Some embodiments provided herein describe a compound, or a pharmaceutically acceptable salt, solvate, polymorph, prodrug, metabolite, N-oxide, stereoisomer, or isomer thereof, having the structure of Formula (I) wherein:

each $R^1$ is independently halogen, optionally substituted $C_{1-6}$ alkyl, optionally substituted $C_{3-6}$ cycloalkyl, optionally substituted $C_{2-4}$ heterocyclyl, optionally substituted $C_{3-10}$ heterocyclalkyl, —$COR^7$, —$CON(R^7)_2$, optionally substituted ($C_0$-$C_4$ alkylene)-CN, optionally substituted ($C_0$-$C_4$ alkylene)-$OR^7$, optionally substituted ($C_0$-$C_4$ alkylene)-$N(R^7)_2$, optionally substituted ($C_0$-$C_4$ alkylene)$N(R^8)$—$COR^7$, optionally substituted ($C_0$-$C_4$ alkylene)-$SO_2N(R^7)_2$, optionally substituted ($C_0$-$C_4$ alkylene)-$SO_2R^7$, optionally substituted ($C_0$-$C_4$ alkylene)$N(R^8)$—$SO_2N(R^7)_2$, or optionally substituted ($C_0$-$C_4$ alkylene)$N(R^8)$—$SO_2R^7$;

each $R^7$ is independently selected from H, optionally substituted $C_{1-6}$ alkyl, optionally substituted $C_{3-6}$ carbocyclyl, optionally substituted $C_{3-10}$ carbocyclylalkyl, optionally substituted $C_{2-6}$ heterocyclyl, optionally substituted $C_{2-10}$ heterocyclylalkyl; or two $R^{11}$ groups together with the nitrogen to which they are attached join to form an optionally substituted $C_2$. N-heterocyclyl;

each $R^8$ is independently selected from H or optionally substituted $C_{1-6}$ alkyl;

$R^2$ is —H, —OH, optionally substituted $C_{1-6}$ alkyl, or halogen, p is 0, 1, 2, 3, 4, or 5, A has the structure:

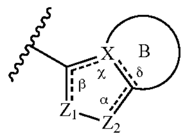

wherein:

- α, β, χ, and δ are each independently absent or present, and when present each is a bond;
- X is N;
- $Z_1$ is S, O, or N;
- $Z_2$ is S, O, N, or $NR^3$;
- $R^3$ is H, optionally substituted $C_{1-6}$ alkyl, or oxetane; and
- B is a substituted or unsubstituted fused 5-, 6-, or 7-membered ring structure.

Certain embodiments provided herein describe a compound, or a pharmaceutically acceptable salt, solvate, polymorph, prodrug, metabolite. N-oxide, stereoisomer, or isomer thereof, having the structure of Formula (I) wherein:

each $R^1$ is independently halogen, $C_{1-6}$ alkyl, $C_{1-6}$ haloalkyl, $C_{3-6}$ cycloalkyl, $C_{2-6}$ heterocyclyl, $C_{3-10}$ heterocyclalkyl, —$COR^7$, —$CON(R^7)_2$, ($C_0$-$C_4$ alkylene)-CN, ($C_0$-$C_4$ alkylene)-$OR^7$, ($C_0$-$C_4$ alkylene)-$N(R^7)_2$, ($C_0$-$C_4$ alkylene)$N(R^8)$—$COR^7$, ($C_0$-$C_4$ alkylene)-$SO_2N(R^7)_2$, ($C_0$-$C_4$ alkylene)-$SO_2R^7$, ($C_0$-$C_4$ alkylene)$N(R^8)$—$SO_2N(R^7)_2$, or ($C_0$-$C_4$ alkylene)$N(R^8)$—$SO_2R^7$;

each $R^7$ is independently selected from H, $C_{1-6}$ alkyl, $C_{3-6}$ carbocyclyl, $C_{3-10}$ carbocyclylalkyl, $C_{2-6}$ heterocyclyl, $C_{2-10}$ heterocyclylalkyl; or two $R^{11}$ groups together with the nitrogen to which they are attached join to form a $C_{2-6}$ N-heterocyclyl;

each $R^8$ is independently selected from H or $C_{1-6}$ alkyl;

$R^2$ is —H, —OH, $C_{1-6}$ alkyl, or halogen;

p is 0, 1, 2, 3, 4, or 5;

A has the structure

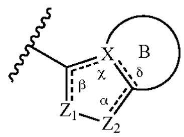

wherein:

- α, β, χ, and δ are each independently absent or present, and when present each is a bond;
- X is N;
- $Z_1$ is S, O, or N;
- $Z_2$ is S, O, N, or $NR^3$;
- $R^3$ is H, $C_{1-6}$ alkyl, or oxetane; and
- B is a substituted or unsubstituted fused 5-, 6-, or 7-membered ring structure.

Some embodiments provided herein describe a compound, or a pharmaceutically acceptable salt, solvate, polymorph, prodrug, metabolite, N-oxide, stereoisomer, or isomer thereof, having the structure of Formula (I) wherein:

each $R^1$ is independently halogen, haloalkyl, or alkyl;

$R^2$ is —H, —OH, or halogen;

p is 0, 1, 2, 3, 4, or 5;

A has the structure:

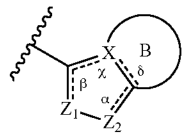

wherein:

- α, β, χ, and δ are each independently absent or present, and when present each is a bond;
- X is N;
- $Z_1$ is S, O, or N;
- $Z_2$ is S, O, N, or $NR^3$;
- $R^3$ is H, $C_1$-$C_4$ alkyl, or oxetane; and
- B is a substituted or unsubstituted fused 5-, 6-, or 7-membered ring structure.

Certain embodiments provided herein describe a compound, or a pharmaceutically acceptable salt, solvate, polymorph, prodrug, metabolite, N-oxide, stereoisomer, or isomer thereof, having the structure of Formula (I) wherein:

each $R^1$ is independently Br, Cl, F, $C_{1-6}$ fluoroalkyl, or $C_{1-6}$ alkyl, $R^2$ is —H, —OH, Br, Cl, or F;

p is 0, 2, 3, 4, or 5;

A has the structure.

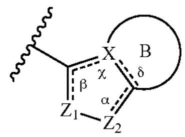

wherein:

- α, β, χ, and δ are each independently absent or present, and when present each is a bond;
- X is N;
- $Z_1$ is S, O, or N;
- $Z_2$ is S, O, N, or $NR^3$;
- $R^3$ is H, $C_1$-$C_4$ alkyl, or oxetane; and
- B is a substituted or unsubstituted fused 5-, 6-, or 7-membered ring structure.

Certain embodiments provided herein describe a compound, or a pharmaceutically acceptable salt, solvate, polymorph, prodrug, metabolite, N-oxide, stereoisomer, or isomer thereof, having the structure of Formula (I) wherein:

each $R^1$ is independently F or $CF_3$;

$R^2$ is —H, p is 1 or 2;

A has the structure:

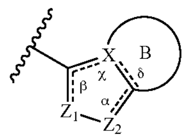

wherein:

- α, β, χ, and δ are each independently absent or present, and when present each is a bond;
- X is N;
- $Z_1$ is S, O, or N;
- $Z_2$ is S, O, N, or $NR^3$;
- $R^3$ is H, $C_1$-$C_4$ alkyl, or oxetane; and B is a substituted or unsubstituted fused 5-, 6-, or 7-membered ring structure.

For any and all of the embodiments of Formula (I), substituents are selected from among a subset of the listed alternatives.

In some embodiments, each $R^1$ is independently halogen, optionally substituted $C_{1-6}$ alkyl, optionally substituted $C_{3-6}$ cycloalkyl, optionally substituted $C_{2-6}$ heterocyclyl, optionally substituted $C_{3-10}$ heterocyclalkyl, —$COR^7$, —$CON(R^7)_2$, optionally substituted ($C_0$-$C_4$ alkylene)-CN, optionally substituted ($C_0$-$C_4$ alkylene)-$OR^7$, optionally substituted ($C_0$-$C_4$ alkylene)-$N(R^7)_2$, optionally substituted ($C_0$-$C_4$ alkylene)$N(R^8)$—$COR^7$, optionally substituted ($C_0$-$C_4$ alkylene)-$SO_2N(R^7)_2$, optionally substituted ($C_0$-$C_4$ alkylene)-$SO_2R^7$, optionally substituted ($C_0$-$C_4$ alkylene)$N(R^8)$—$SO_2N(R^7)_2$, or optionally substituted ($C_0$-$C_4$ alkylene)$N(R^8)$—$SO_2R^7$. In certain embodiments, each $R^1$ is independently halogen, $C_{1-6}$ alkyl, $C_{1-6}$ haloalkyl, $C_{1-6}$ cycloalkyl, $C_{2-6}$ heterocyclyl, $C_{3-10}$ heterocyclalkyl, —$COR^7$, —$CON(R^7)_2$, ($C_0$-$C_4$ alkylene)-CN, ($C_0$-$C_4$ alkylene)-$OR^7$, ($C_0$-$C_4$ alkylene)-$N(R^7)_2$, ($C_0$-$C_4$ alkylene) $N(R^8)$—$COR^7$, ($C_0$-$C_4$ alkylene)-$SO_2N(R^7)$, ($C_0$-$C_4$ alkylene)-$SO_2R^7$, ($C_0$-$C_4$ alkylene)$N(R^8)$—$SO_2N(R^7)_2$, or ($C_0$-$C_4$ alkylene)$N(R^8)$—$SO_2R^7$. In some embodiments, each $R^1$ is independently halogen, $C_{1-6}$ alkyl, $C_{1-6}$ haloalkyl, —$COR^7$, —$CON(R^7)_2$, ($C_0$-$C_4$ alkylene)-CN, ($C_0$-$C_4$ alkylene)-$OR^7$, or ($C_0$-$C_4$ alkylene)-$N(R^7)_2$. In other embodiments, each $R^1$ is independently ($C_0$-$C_4$ alkylene)$N(R^8)$—$COR^7$, ($C_0$-$C_4$ alkylene)-$SO_2N(R^7)$, ($C_0$-$C_4$ alkylene)-$SO_2R^7$, ($C_0$-$C_4$ alkylene)$N(R^8)$—$SO_2N(R^7)_2$, or ($C_0$-$C_4$ alkylene)$N(R^8)$—$SO_2R^7$. In some embodiments, each $R^1$ is independently halogen, $C_{1-6}$ alkyl, $C_{1-6}$ haloalkyl, —$COR^7$, —$CON(R^7)_2$, —CN, ($C_0$-$C_4$ alkylene)-$OR^7$, or ($C_0$-$C_4$ alkylene)-$N(R^7)_2$. In some embodiments, each $R^1$ is independently halogen, $C_{1-6}$ alkyl, $C_{1-6}$ haloalkyl, or —CN. In certain embodiments, each $R^1$ is independently F, Br, Cl, $C_{1-6}$ haloalkyl, or $C_{1-6}$ alkyl. In specific embodiments, each $R^1$ is independently F or $CF_3$.

In some embodiments, each $R^7$ is independently selected from H, optionally substituted $C_{1-6}$ alkyl, optionally substituted $C_{3-6}$ carbocyclyl, optionally substituted $C_{3-10}$ carbocyclylalkyl, optionally substituted $C_{2-6}$ heterocyclyl, optionally substituted $C_{2-10}$ heterocyclylalkyl; or two $R^{11}$ groups together with the nitrogen to which they are attached join to form an optionally substituted $C_{2-6}$ N-heterocyclyl. In some embodiments, each $R^7$ is independently selected from H, $C_{1-6}$ alkyl, $C_{3-6}$ carbocyclyl, $C_{3-10}$ carbocyclylalkyl, $C_{2-6}$ heterocyclyl, $C_{2-10}$ heterocyclylalkyl; or two $R^{11}$ groups together with the nitrogen to which they are attached join to form a $C_{2-6}$ N-heterocyclyl. In some embodiments, each $R^7$ is independently selected from H, $C_{1-6}$ alkyl, or $C_{3-6}$ carbocyclyl. In certain embodiments, two $R^{11}$ groups together with the nitrogen to which they are attached join to form an optionally substituted $C_{2-6}$ N-heterocyclyl. In some embodiments, each $R^7$ is independently selected from H or $C_{1-6}$ alkyl. In some embodiments, each $R^7$ is H or Me.

In some embodiments, each $R^8$ is independently selected from H, $C_{1-6}$ alkyl, or $C_{1-6}$ haloalkyl. In some embodiments, each $R^8$ is independently selected from H or $C_{1-6}$ alkyl. In some embodiments, each $R^8$ is independently selected from H or Me. In some embodiments, each $R^8$ is H.

In some embodiments, p is 0, 1, 2, 3, or 4. In some embodiments, p is 0, 1, 2, or 3. In some embodiments, p is 0, 1 or 2. In some embodiments, p is 0 or 1. In some embodiments, p is 1, 2, or 3. In some embodiments, p is 1 or 2. In some embodiments, p is 1, 2, 3, or 4. In some embodiments, p is 2, 3, or 4. In some embodiments, p is 2 or 3. In some embodiments, p is 0. In some embodiments, p is 1. In some embodiments, p is 2. In some embodiments, p is 3. In some embodiments, p is 4. In some embodiments, p is 5. In some embodiments, p is 1.

In some embodiments, $R^2$ is —I, —OH, optionally substituted alkyl, or halogen. In some embodiments, $R^2$ is —H, —OH, alkyl, haloalkyl, or halogen. In some embodiments, $R^2$ is —H, —OH, $C_{1-6}$ alkyl, $C_{1-6}$ haloalkyl, or halogen. In some embodiments, $R^2$ is —H, —OH, Me, $CF_3$, or halogen. In some embodiments, $R^2$ is —H, —OH, Me, $CF_3$, Cl, or F. In some embodiments, $R^2$ is —H, —OH, Me, $CF_3$, or F. In some embodiments, $R^2$ is —H, —OH, or halogen. In some embodiments, $R^2$ is —H, —OH, or F. In some embodiments, $R^2$ is —H. In some embodiments, $R^2$ is —OH. In some embodiments, $R^2$ is F. In some embodiments, $R^2$ is Cl.

In some embodiments, α is present. In some embodiments, $Z_1$ and $Z_2$ are N. In some embodiments, β is present. In some embodiments, χ and δ are absent. In certain embodiments, α is present; $Z_1$ and $Z_2$ are N; X is N; β is present; and χ and δ are absent.

In some embodiments, A has the structure

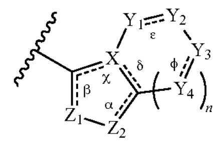

wherein:

n is 0, 1, or 2;

α, β, χ, δ, ε, and ϕ are each independently absent or present, and when present each is a bond;

$Z_1$ is S, O, or N;

$Z_2$ is S, O, N or $NR^3$, wherein $R^3$ is H, $C_1$-$C_4$ alkyl, or oxetane,

X is N;

$Y_1$, $Y_2$, $Y_3$ and each occurrence of $Y_4$ are each independently $CR^4$, $C(R^5)_2$, $NR^6$, O, N, $SO_2$, or —(C═O)—, wherein:

each $R^4$ is independently H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or $C_1$-$C_{10}$ haloalkyl;

each $R^5$ is independently H or $C_1$-$C_{10}$ alkyl; and each $R^6$ is independently H, $C_1$-$C_{10}$ alkyl, $C_3$-$C_6$ cycloalkyl, —($C_1$-$C_{10}$ alkyl)$CF_3$, —($C_1$-$C_{10}$ alkyl)$OCH_3$, —($C_1$-$C_{10}$ alkyl)-halogen, —$SO_2$($C_1$-$C_{10}$ alkyl), —$SO_2$($C_1$-$C_{10}$ alkyl)-$CF_3$, —$SO_2$($C_1$-$C_{10}$ alkyl)$OCH_3$, —$SO_2$($C_1$-$C_{10}$ alkyl)-halogen, —C(O)$C_1$-$C_{10}$ alkyl), —C(O)$C_1$-$C_{10}$ alkyl)$CF_3$, —C(O)($C_1$-$C_{10}$alkyl)$OCH_3$, —C(O)($C_1$-$C_{10}$ alkyl)-halogen, —C(O)NH($C_1$-$C_{10}$ alkyl), —C(O)N($C_1$-$C_{10}$ alkyl)$_2$, —($C_1$-$C_{10}$ alkyl)C(O)OH, —C(O)$NH_2$, or oxetane.

In some embodiments, α is present. In some embodiments, $Z_1$, and $Z_2$ are N. In some embodiments, β is present. In some embodiments, χ and δ are absent. In certain embodiments, α is present; $Z_1$ and $Z_2$ are N; X is N; β is present; and χ and δ are absent.

In some embodiments, ε is present. In some embodiments, ϕ is present. In some embodiments, ε and ϕ are each present. In some embodiments, ε and ϕ are each absent. In some embodiments, n is 0 or 1. In some embodiments, n is 1 or 2. In some embodiments, n is 0. In some embodiments, n is 2. In some embodiments, n is 1. In some embodiments, each of $Y_1$, $Y_2$, $Y_3$, and $Y_4$, are independently —$CR^4$— or N. In some embodiments, each of $Y_1$, $Y_2$, $Y_3$, and each occurrence of $Y_4$ are independently $C(R^5)_2$, $NR^6$, O, or $SO_2$. In some embodiments, ε and ϕ are each present; n=1; and each of $Y_1$, $Y_2$, $Y_3$, and $Y_4$, are independently —$CR^4$— or N. In certain embodiments, ε and ϕ are each absent; n is 0, 1 or 2; and each of $Y_1$, $Y_2$, $Y_3$, and each occurrence of $Y_4$ are independently $C(R^5)_2$, $NR^6$, O, or $SO_2$.

In some embodiments, α, β, ε, and ϕ are present. In some embodiments, χ and δ are absent. In some embodiments, $Z_1$ is N. In some embodiments, $Z_2$ is N. In certain embodiments, α, β, ε, and ϕ are present; χ and δ are absent; $Z_1$ is N; $Z_2$ is N; and X is N.

In some embodiments, A has the structure.

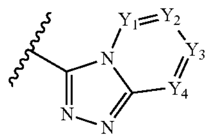

wherein:

$Y_1$, $Y_2$, $Y_3$ and $Y_4$ are each independently $CR^4$ or N; and each $R^4$ is independently H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$alkyl), —$SO_2$N($C_1$-$C_{10}$ alkyl)$_2$, —CN, or $C_1$-$C_{10}$ haloalkyl.

In some embodiments, $Y_1$, $Y_2$, $Y_3$ and $Y_4$ are $CR^4$. In some embodiments, $Y_1$, $Y_2$, $Y_3$ are $CR^4$ and $Y_4$ is N. In some embodiments, $Y_1$, $Y_2$, $Y_4$ are $CR^4$ and $Y_3$ is N. In some embodiments, $Y_1$, $Y_3$, $Y_4$ are $CR^4$ and $Y_2$ is N. In some embodiments, $Y_2$, $Y_3$, $Y_4$ are $CR^4$ and $Y_1$ is N.

In some embodiments, $R^3$ is H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$. In some embodiments, $R^3$ is H, halogen, $C_1$-$C_6$ alkyl, $C_1$-$C_6$ cycloalkyl, —O($C_1$-$C_6$ alkyl), —C(O)OH, —C(O)O($C_1$-$C_6$ alkyl), —C(O)$NH_2$, —C(O)NH($C_1$-$C_4$ alkyl), —C(O)N($C_1$-$C_4$ alkyl)$_2$, —NHC(O)NH($C_1$-$C_6$ alkyl), —NHC(O)N($C_1$-$C_4$ alkyl)$_2$, —$SO_2$NH($C_1$-$C_6$ alkyl), —$SO_2$N($C_1$-$C_6$ alkyl)$_2$, —CN, or —$CF_3$.

In some embodiments, each $R^4$ is independently H, halogen, $C_1$-$C_6$ alkyl, $C_1$-$C_6$haloalkyl, $C_1$-$C_6$ cycloalkyl, —O($C_1$-$C_6$ alkyl), —C(O)OH, —C(O)O($C_1$-$C_6$ alkyl), —C(O)$NH_2$, —C(O)NH($C_1$-$C_4$ alkyl), —C(O)N($C_1$-$C_4$ alkyl)$_2$, —NHC(O)NH($C_1$-$C_6$ alkyl), —NHC(O)N($C_1$-$C_4$ alkyl)$_2$, —$SO_2$NH($C_1$-$C_6$ alkyl), —$SO_2$N($C_1$-$C_6$ alkyl)$_2$, or —CN. In some embodiments, each $R^4$ is independently H, halogen, $C_1$-$C_6$ alkyl, $C_1$-$C_6$ haloalkyl, $C_1$-$C_6$ cycloalkyl, —O($C_1$-$C_6$ alkyl), —C(O)NH($C_1$-$C_4$ alkyl), —C(O)N($C_1$-$C_4$ alkyl)$_2$, —$SO_2$NH($C_1$-$C_6$ alkyl), —$SO_2$N($C_1$-$C_6$ alkyl)$_2$, or —CN. In some embodiments, each $R^4$ is independently H, halogen, $C_1$-$C_6$ alkyl, $C_1$-$C_6$ haloalkyl, or —CN. In some embodiments, each $R^4$ is independently H, halogen, $C_1$-$C_4$ alkyl, $C_3$-$C_6$ cycloalkyl, —O($C_1$-$C_4$ alkyl), —CN, —$CF_3$, —C(O)OH, —C(O)$NH_2$, —C(O)N($CH_3$)$_2$, —C(O)NH$CH_3$, or —NHC(O)N($CH_3$)$_2$. In some embodiments, each $R_4$ is independently H, halogen, $C_1$-$C_4$ alkyl, $C_3$-$C_6$ cycloalkyl, —O($C_1$-$C_4$ alkyl), —CN, —$CF_3$, —C(O)OH, —C(O)$NH_2$, —C(O)N($CH_3$)$_2$, —C(O)NH$CH_3$, or —NHC(O)N($CH_3$)$_2$. In some embodiments, each $R^4$ is independently H, halogen, methyl, methoxy, —CN, —$CF_3$, —C(O)N($CH_3$)$_2$, —C(O)NH$CH_3$, or —C(O)Me. In some embodiments, each $R^4$ is independently H, F, methyl, methoxy, —CN, —$CF_3$, —C(O)N($CH_3$)$_2$, —C(O)NH$CH_3$, or —C(O)Me. In some embodiments, each $R^4$ is independently H, F, methyl, methoxy, —CN, or —$CF_3$. In some embodiments, each $R^4$ is independently H or —CN.

In some embodiments, each $R^6$ is independently H or $C_1$-$C_6$ alkyl. In some embodiments, $R^5$ is H.

In some embodiments, each $R^6$ is independently H, $C_1$-$C_6$ alkyl, $C_3$-$C_6$ cycloalkyl, —($C_1$-$C_6$ alkylene)$CF_3$, —($C_1$-$C_6$ alkylene)$OCH_3$, —($C_1$-$C_6$ alkylene)-halogen, —$SO_2$-$C_1$-$C_6$ alkyl, —$SO_2$($C_1$-$C_6$ alkylene)-$CF_3$, —$SO_2$($C_1$-$C_6$ alkylene)$OCH_3$, —$SO_2$($C_1$-$C_6$ alkylene)-halogen, —C(O)($C_1$-$C_6$ alkyl), —C(O)$C_1$-$C_6$ alkylene)$CF_3$, —C(O)($C_1$-$C_6$ alkylene)$OCH_3$, —C(O)($C_1$-$C_6$ alkylene)-halogen, —C(O)NH($C_1$-$C_6$ alkyl), —C(O)N($C_1$-$C_6$ alkyl)$_2$, —($C_1$-$C_6$ alkylene)C(O)OH, —C(O)$NH_2$, or oxetane. In some embodiments, each $R^6$ is independently $C_1$-$C_6$ alkyl, $C_3$-$C_6$ cycloalkyl, —($C_1$-$C_6$ alkylene)$CF_3$, —($C_1$-$C_6$ alkylene)$OCH_3$, —($C_1$-$C_6$ alkylene)-halogen, —$SO_2$-$C_1$-$C_6$ alkyl, —$SO_2$($C_1$-$C_6$ alkylene)-$CF_3$, —$SO_2$($C_1$-$C_6$ alkylene)$OCH_3$, —$SO_2$($C_1$-$C_6$ alkylene)-halogen, —C(O)($C_1$-$C_6$ alkyl), —C(O)($C_1$-$C_6$ alkylene)$CF_3$, —C(O)$C_1$-$C_6$ alkylene)$OCH_3$, —C(O)($C_1$-$C_6$ alkylene)-halogen, —C(O)NH($C_1$-$C_6$ alkyl), —C(O)N($C_1$-$C_6$ alkyl)$_2$, —($C_1$-$C_6$ alkylene)C(O)OH, —C(O)$NH_2$, or oxetane. In some embodiments, each $R^6$ is independently —C(O)($C_1$-$C_6$ alkyl). In some embodiments, each $R^6$ is independently H, $C_1$-$C_4$ alkyl, —$CH_2CH_2CH_3$, —CH($CH_3$)$_2$, —$CH_2$CH($CH_3$)$_2$, t-Bu, —$CH_2OCH_3$, —$CH_2CF_3$, —$CH_2C_1$, —$CH_2F$, —$CH_2CH_2OCH_3$, —$CH_2CH_2CF_3$, —$CH_2CH_2C_1$, —$CH_2CH_2F$,

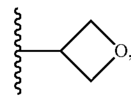

$SO_2CH_3$, —$SO_2CH_2CH_3$, —$SO_2CH_2CH_2CH_3$, —$SO_2$CH($CH_3$)$_2$, —$SO_2CH_2$CH($CH_3$)$_2$, —$SO_2$(t-Bu), —$SO_2CH_2OCH_3$, —$SO_2CH_2CF_3$, —$SO_2CH_2Cl$, —$SO_2CH_2F$, —$SO_2CH_2CH_2OCH_3$, —$SO_2CH_2CH_2CF_3$, —$SO_2CH_2CH_2Cl$, —$SO_2CH_2CH_2F$,

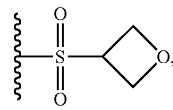

C(O)$CH_3$, C(O)$CH_2C_3$, —C(O)$CH_2CH_2CH_3$, —C(O)CH($CH_3$)$_2$, —C(O)$CH_2$CH($CH_3$)$_2$, —C(O)t-Bu, —C(O)$CH_2OCH_3$, —C(O)$CH_2CF_3$, —C(O)$CH_2Cl$, —C(O)$CH_2F$, —C(O)$CH_2CH_2OCH_3$, —C(O)$CH_2CH_2CF_3$, —C(O)$CH_2CH_2Cl$, —C(O)$CH_2CH_2F$,

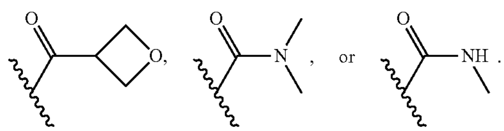

In some embodiments, each $R^6$ is independently —C(O)($C_1$-$C_6$ alkyl) In some embodiments, each $R^6$ is independently H, $C_1$-$C_4$alkyl, —$CH_2CH_2CH_3$, —$CH(CH_3)_2$, —$CH_2CH(CH_3)_2$, t-Bu, —$CH_2OCH_3$, —$CH_2CF_3$, —$CH_2Cl$, —$CH_2F$, —$CH_2CH_2OCH_3$, —$CH_2CH_2CF_3$, —$CH_2CH_2Cl$, —$CH_2CH_2F$, or

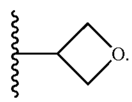 [SMILES: *C1COC1]

In other embodiments, each $R^6$ is independently —$SO_2CH_3$, —$SO_2CH_2CH_3$, —$SO_2CH_2CH_2CH_3$, —$SO_2CH(CH_3)_2$, —$SO_2CH_2CH(CH_3)_2$, —$SO_2$(t-Bu), —$SO_2CH_2CH_3$, —$SO_2CH_2CF_3$, —$SO_2CH_2C_1$, —$SO_2CH_2F$, —$SO_2CH_2CH_2OCH_3$, —$SO_2CH_2CH_2CF_3$, —$SO_2CH_2CH_2Cl$, —$SO_2CH_2CH_2F$, or

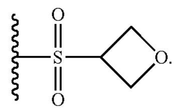 [SMILES: *S(=O)(=O)C1COC1]

In certain embodiments, each $R^6$ is independently $C(O)CH_3$, $C(O)CH_2CH_3$, —$C(O)CH_2CH_2CH_3$, —$C(O)CH(CH_3)_2$, —$C(O)CH_2CH(CH_3)_2$, —C(O)t-Bu, —$C(O)CH_2OCH_3$, —$C(O)CH_2CF_3$, —$C(O)CH_2C_1$, —$C(O)CH_2F$, —C(O)$CH_2CH_2OCH_3$, —$C(O)CH_2CH_2CF_3$, —$C(O)CH_2CH_2Cl$, —$C(O)CH_2CH_2F$,

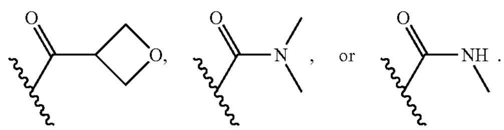

In some embodiments, A has the structure:

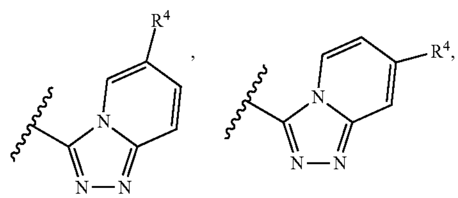

-continued

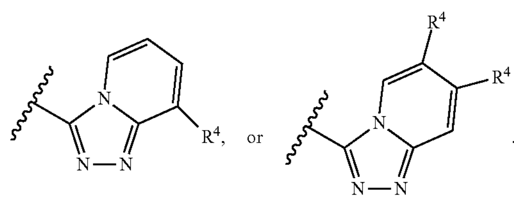

In some embodiments, A has the structure:

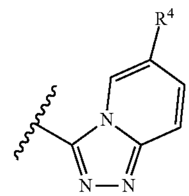

In some embodiments, A has the structure:

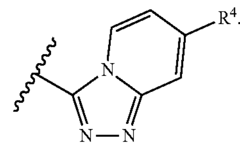

In some embodiments, A has the structure:

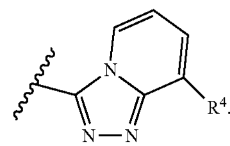

In some embodiments, A has the structure:

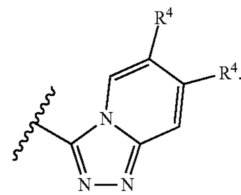

In some embodiments, the heterocyclic compounds of Formula (I) are provided in Table 1.

TABLE 1

| Compound No. | Name | Structure |
|---|---|---|
| 1 | 3-(4-(2-(trifluoromethyl)phenyl)piperidine-1-carbonyl)-[1,2,4]triazolo[4,3-a]pyridine-6-carbonitrile | 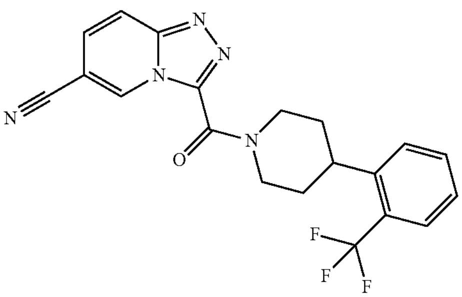 [SMILES: N#Cc1ccc2nnc(C(=O)N3CCC(c4ccccc4C(F)(F)F)CC3)n2c1] |
| 2 | 3-(4-(3-fluoro-2-(trifluoromethyl)phenyl)piperidine-1-carbonyl)-[1,2,4]triazolo[4,3-a]pyridine-6-carbonitrile | 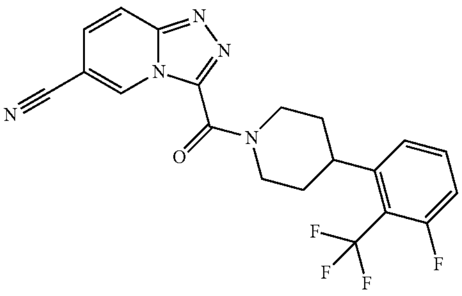 [SMILES: N#Cc1ccc2nnc(C(=O)N3CCC(c4cccc(F)c4C(F)(F)F)CC3)n2c1] |
| 3 | 1,1-dimethyl-3-(3-(4-(2-(trifluoromethyl)phenyl)piperidine-1-carbonyl)-[1,2,4]triazolo[4,3-a]pyridin-6-yl)urea | 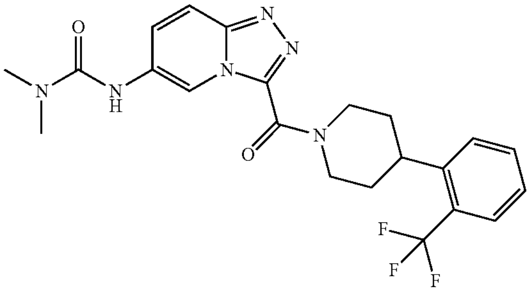 [SMILES: CN(C)C(=O)Nc1ccc2nnc(C(=O)N3CCC(c4ccccc4C(F)(F)F)CC3)n2c1] |
| 4 | 3-(4-(2-(trifluoromethyl)phenyl)piperidine-1-carbonyl)-[1,2,4]triazolo[4,3-a]pyridine-7-carboxylic acid | 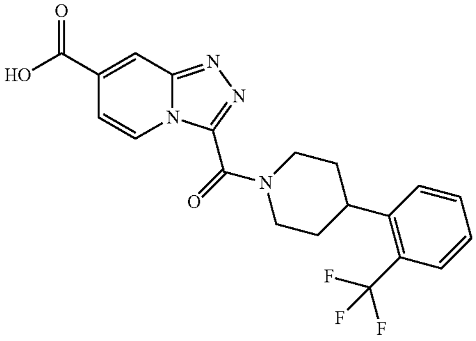 [SMILES: O=C(O)c1ccn2c(C(=O)N3CCC(c4ccccc4C(F)(F)F)CC3)nnc2c1] |
| 5 | N,N-dimethyl-3-(4-(2-(trifluoromethyl)phenyl)piperidine-1-carbonyl)-[1,2,4]triazolo[4,3-a]pyridine-7-carboxamide | 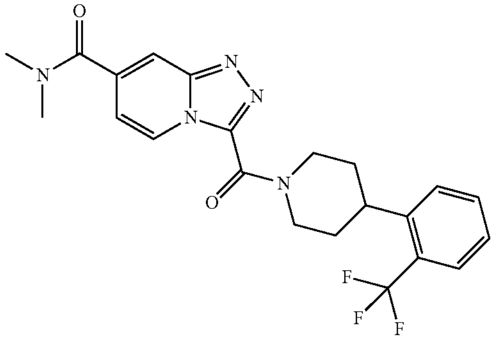 [SMILES: CN(C)C(=O)c1ccn2c(C(=O)N3CCC(c4ccccc4C(F)(F)F)CC3)nnc2c1] |

TABLE 1-continued

| Compound No. | Name | Structure |
|---|---|---|
| 6 | (6-fluoro-[1,2,4]triazolo[4,3-a]pyridin-3-yl)(4-(2-(trifluoromethyl)phenyl)piperidin-1-yl)methanone | 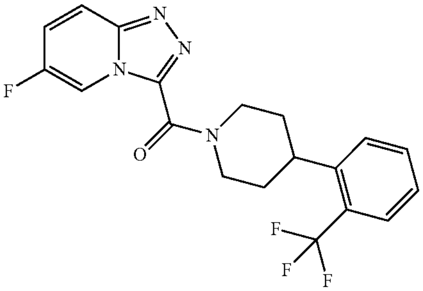 [SMILES: O=C(c1nnc2ccc(F)cn12)N1CCC(c2ccccc2C(F)(F)F)CC1] |
| 7 | N-methyl-3-(4-(2-(trifluoromethyl)phenyl)piperidine-1-carbonyl)-[1,2,4]triazolo[4,3-a]pyridine-7-carboxamide | 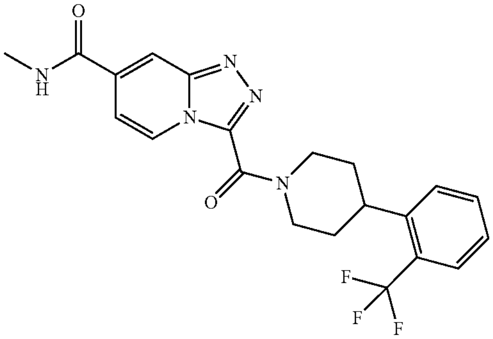 [SMILES: CNC(=O)c1ccn2c(C(=O)N3CCC(c4ccccc4C(F)(F)F)CC3)nnc2c1] |
| 8 | 3-(4-(2-(trifluoromethyl)phenyl)piperidine-1-carbonyl)-[1,2,4]triazolo[4,3-a]pyridine-7-carboxamide | 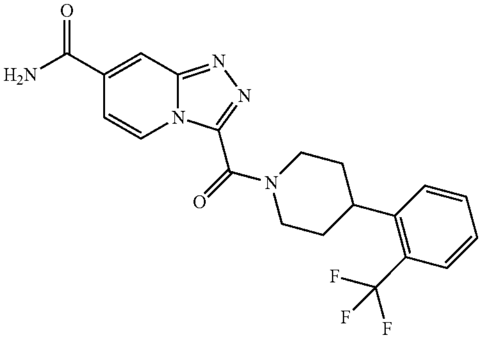 [SMILES: NC(=O)c1ccn2c(C(=O)N3CCC(c4ccccc4C(F)(F)F)CC3)nnc2c1] |
| 9 | (6-bromo-[1,2,4]triazolo[4,3-a]pyridin-3-yl)(4-(2-(trifluoromethyl)phenyl)piperidin-1-yl)methanone | 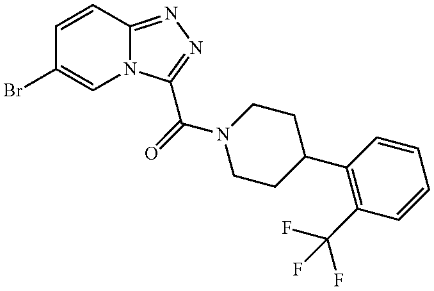 [SMILES: O=C(c1nnc2ccc(Br)cn12)N1CCC(c2ccccc2C(F)(F)F)CC1] |

TABLE 1-continued

| Compound No. | Name | Structure |
| --- | --- | --- |
| 10 | (7-methyl-[1,2,4]triazolo[4,3-a]pyridin-3-yl)(4-(2-(trifluoromethyl)phenyl)piperidin-1-yl)methanone | 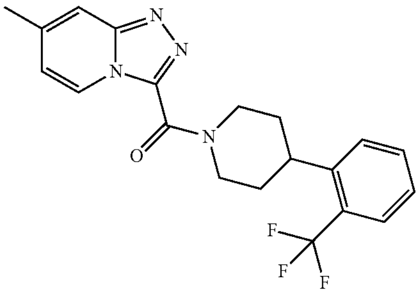 [SMILES: Cc1ccn2c(C(=O)N3CCC(c4ccccc4C(F)(F)F)CC3)nnc2c1] |
| 11 | (7-(trifluoromethyl)-[1,2,4]triazolo[4,3-a]pyridin-3-yl)(4-(2-(trifluoromethyl)phenyl)piperidin-1-yl)methanone | 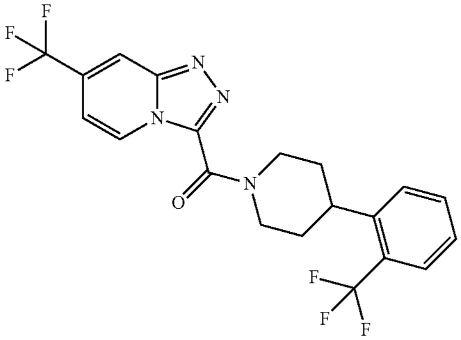 [SMILES: O=C(c1nnc2cc(C(F)(F)F)ccn12)N1CCC(c2ccccc2C(F)(F)F)CC1] |
| 12 | (6-ethoxy-[1,2,4]triazolo[4,3-a]pyridin-3-yl)(4-(2-(trifluoromethyl)phenyl)piperidin-1-yl)methanone | 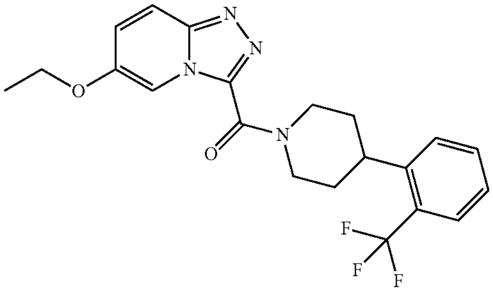 [SMILES: CCOc1ccc2nnc(C(=O)N3CCC(c4ccccc4C(F)(F)F)CC3)n2c1] |
| 13 | (6-(trifluoromethyl)-[1,2,4]triazolo[4,3-a]pyridin-3-yl)(4-(2-(trifluoromethyl)phenyl)piperidin-1-yl)methanone | 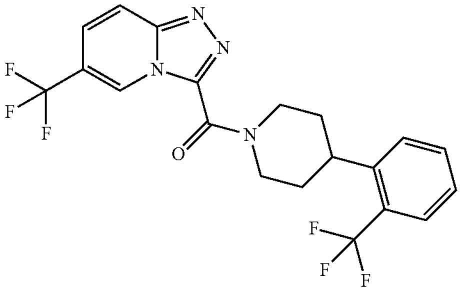 [SMILES: O=C(c1nnc2ccc(C(F)(F)F)cn12)N1CCC(c2ccccc2C(F)(F)F)CC1] |
| 14 | (6-chloro-[1,2,4]triazolo[4,3-a]pyridin-3-yl)(4-(2-(trifluoromethyl)phenyl)piperidin-1-yl)methanone | 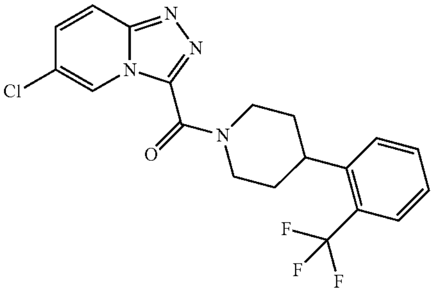 [SMILES: O=C(c1nnc2ccc(Cl)cn12)N1CCC(c2ccccc2C(F)(F)F)CC1] |

TABLE 1-continued

| Compound No. | Name | Structure |
|---|---|---|
| 15 | (6-methyl-[1,2,4]triazolo[4,3-a]pyridin-3-yl)(4-(2-(trifluoromethyl)phenyl)piperidin-1-yl)methanone | 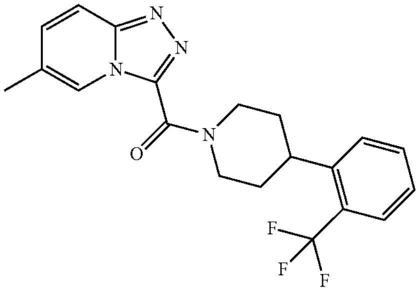 [SMILES: Cc1ccc2nnc(C(=O)N3CCC(c4ccccc4C(F)(F)F)CC3)n2c1] |
| 16 | 3-(4-(2-(trifluoromethyl)phenyl)piperidine-1-carbonyl)-[1,2,4]triazolo[4,3-a]pyridine-6-carboxylic acid | 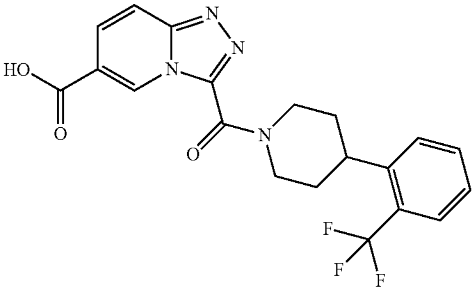 [SMILES: O=C(O)c1ccc2nnc(C(=O)N3CCC(c4ccccc4C(F)(F)F)CC3)n2c1] |
| 17 | N,N-dimethyl-3-(4-(2-(trifluoromethyl)phenyl)piperidine-1-carbonyl)-[1,2,4]triazolo[4,3-a]pyridine-6-carboxamide | 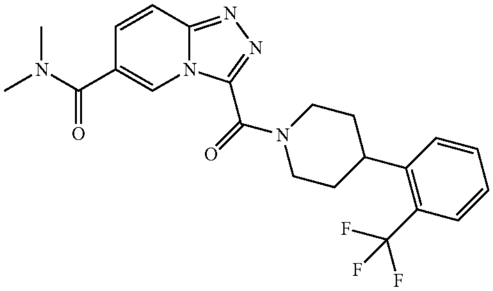 [SMILES: CN(C)C(=O)c1ccc2nnc(C(=O)N3CCC(c4ccccc4C(F)(F)F)CC3)n2c1] |
| 18 | N-methyl-3-(4-(2-(trifluoromethyl)phenyl)piperidine-1-carbonyl)-[1,2,4]triazolo[4,3-a]pyridine-6-carboxamide | 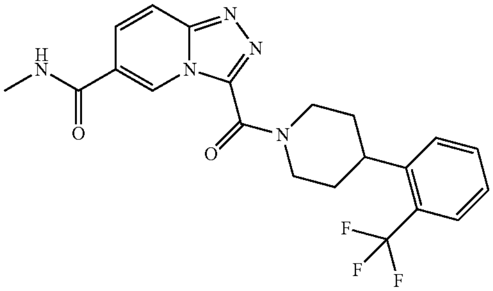 [SMILES: CNC(=O)c1ccc2nnc(C(=O)N3CCC(c4ccccc4C(F)(F)F)CC3)n2c1] |
| 19 | 3-(4-(2-(trifluoromethyl)phenyl)piperidine-1-carbonyl)-[1,2,4]triazolo[4,3-a]pyridine-6-carboxamide | 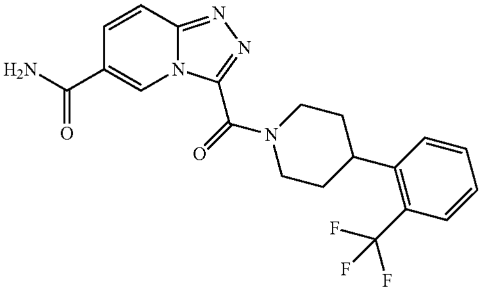 [SMILES: NC(=O)c1ccc2nnc(C(=O)N3CCC(c4ccccc4C(F)(F)F)CC3)n2c1] |

TABLE 1-continued

| Compound No. | Name | Structure |
|---|---|---|
| 20 | (6-methoxy-[1,2,4]triazolo[4,3-a]pyridin-3-yl)(4-(2-(trifluoromethyl)phenyl)piperidin-1-yl)methanone | 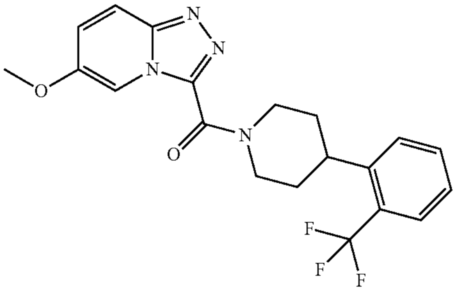 [SMILES: COc1ccc2nnc(C(=O)N3CCC(c4ccccc4C(F)(F)F)CC3)n2c1] |
| 21 | 1-(3-(4-(2-(trifluoromethyl)phenyl)piperidine-1-carbonyl)-5,6-dihydro-[1,2,4]triazolo[4,3-a]pyrazin-7(8H)-yl)ethan-1-one | 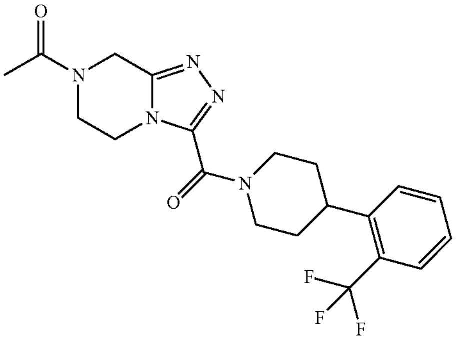 [SMILES: CC(=O)N1CCn2c(nnc2C(=O)N2CCC(c3ccccc3C(F)(F)F)CC2)C1] |
| 22 | (7-(methylsulfonyl)-5,6,7,8-tetrahydro-[1,2,4]triazolo[4,3-a]pyrazin-3-yl)(4-(2-(trifluoromethyl)phenyl)piperidin-1-yl)methanone | 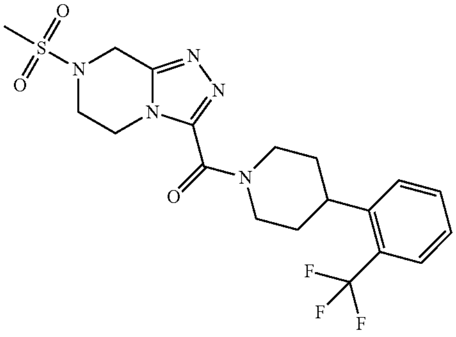 [SMILES: CS(=O)(=O)N1CCn2c(nnc2C(=O)N2CCC(c3ccccc3C(F)(F)F)CC2)C1] |
| 23 | (6-(methylsulfonyl)-5,6,7,8-tetrahydro-[1,2,4]triazolo[4,3-c]pyrimidin-3-yl)(4-(2-(trifluoromethyl)phenyl)piperidin-1-yl)methanone | 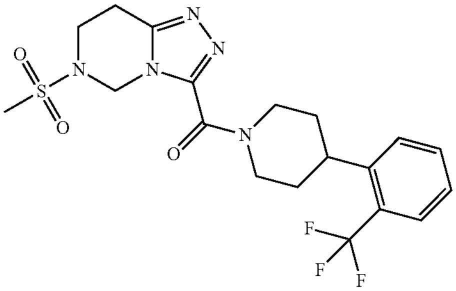 [SMILES: CS(=O)(=O)N1CCc2nnc(C(=O)N3CCC(c4ccccc4C(F)(F)F)CC3)n2C1] |
| 24 | 1-(3-(4-(2-(trifluoromethyl)phenyl)piperidine-1-carbonyl)-7,8-dihydro-[1,2,4]triazolo[4,3-c]pyrimidin-6(5H)-yl)ethan-1-one | 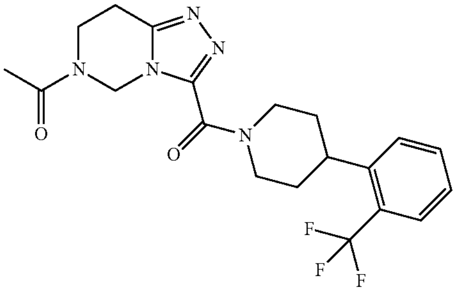 [SMILES: CC(=O)N1CCc2nnc(C(=O)N3CCC(c4ccccc4C(F)(F)F)CC3)n2C1] |

TABLE 1-continued

| Compound No. | Name | Structure |
|---|---|---|
| 25 | (5,6,7,8-tetrahydro-[1,2,4]triazolo[4,3-a]pyrazin-3-yl)(4-(2-(trifluoromethyl)phenyl)piperidin-1-yl)methanone | 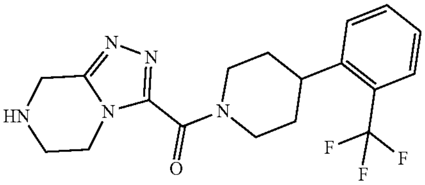 [SMILES: O=C(c1nnc2n1CCNC2)N1CCC(c2ccccc2C(F)(F)F)CC1] |
| 26 | (5,6,7,8-tetrahydro-[1,2,4]triazolo[4,3-c]pyrimidin-3-yl)(4-(2-(trifluoromethyl)phenyl)piperidin-1-yl)methanone | 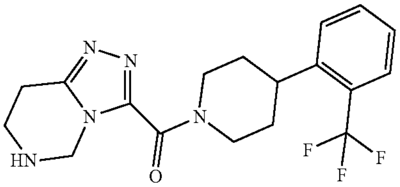 [SMILES: O=C(c1nnc2n1CNCC2)N1CCC(c2ccccc2C(F)(F)F)CC1] |
| 27 | (5,6-dihydro-8H-[1,2,4]triazolo[3,4-c][1,4]oxazin-3-yl)(4-(2-(trifluoromethyl)phenyl)piperidin-1-yl)methanone | 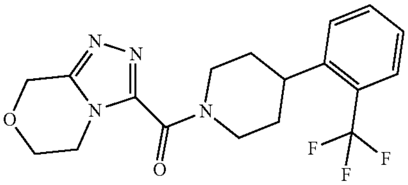 [SMILES: O=C(c1nnc2n1CCOC2)N1CCC(c2ccccc2C(F)(F)F)CC1] |
| 28 | (7,8-dihydro-5H-[1,2,4]triazolo[4,3-c][1,3]oxazin-3-yl)(4-(2-(trifluoromethyl)phenyl)piperidin-1-yl)methanone | 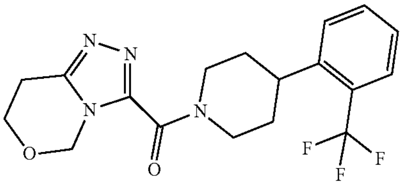 [SMILES: O=C(c1nnc2n1COCC2)N1CCC(c2ccccc2C(F)(F)F)CC1] |
| 29 | (7-methyl-5,6,7,8-tetrahydro-[1,2,4]triazolo[4,3-a]pyrazin-3-yl)(4-(2-(trifluoromethyl)phenyl)piperidin-1-yl)methanone | 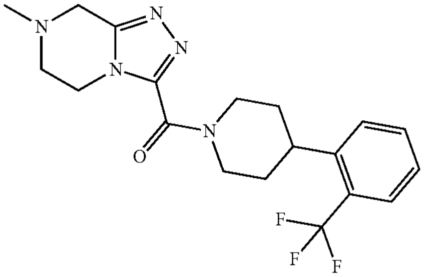 [SMILES: CN1CCn2c(nnc2C(=O)N2CCC(c3ccccc3C(F)(F)F)CC2)C1] |
| 30 | (6-methyl-5,6,7,8-tetrahydro-[1,2,4]triazolo[4,3-c]pyrimidin-3-yl)(4-(2-(trifluoromethyl)phenyl)piperidin-1-yl)methanone | 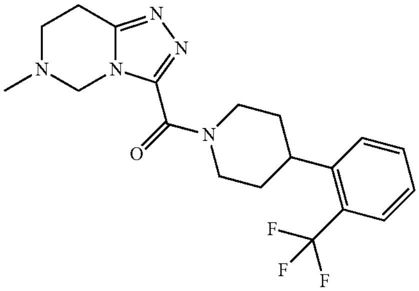 [SMILES: CN1CCc2nnc(C(=O)N3CCC(c4ccccc4C(F)(F)F)CC3)n2C1] |

TABLE 1-continued

| Compound No. | Name | Structure |
|---|---|---|
| 31 | (6-bromo-[1,2,4]triazolo[4,3-a]pyridin-3-yl)(4-(3-chloro-2-(trifluoromethyl)phenyl)piperidin-1-yl)methanone | 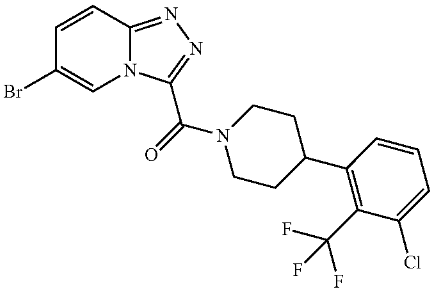 |
| 32 | (6-bromo-[1,2,4]triazolo[4,3-a]pyridin-3-yl)(4-(4-fluoro-2-(trifluoromethyl)phenyl)piperidin-1-yl)methanone | 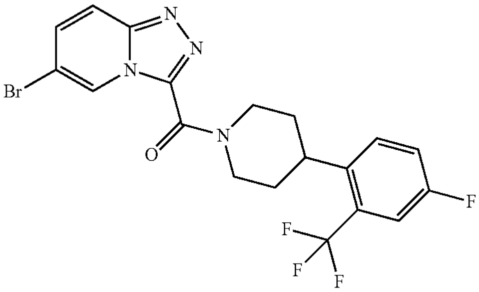 [SMILES: O=C(c1nnc2ccc(Br)cn12)N1CCC(c2ccc(F)cc2C(F)(F)F)CC1] |
| 33 | (6-bromo-[1,2,4]triazolo[4,3-a]pyridin-3-yl)(4-(5-fluoro-2-(trifluoromethyl)phenyl)piperidin-1-yl)methanone | 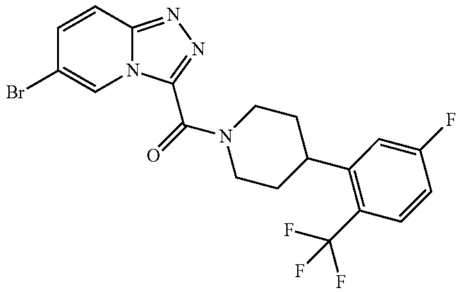 [SMILES: O=C(c1nnc2ccc(Br)cn12)N1CCC(c2cc(F)ccc2C(F)(F)F)CC1] |
| 34 | (6-bromo-[1,2,4]triazolo[4,3-a]pyridin-3-yl)(4-(3,5-difluoro-2-(trifluoromethyl)phenyl)piperidin-1-yl)methanone | 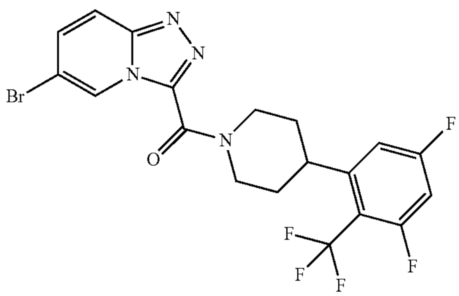 [SMILES: O=C(c1nnc2ccc(Br)cn12)N1CCC(c2cc(F)cc(F)c2C(F)(F)F)CC1] |
| 35 | (4-(3,5-bis(trifluoromethyl)phenyl)piperidin-1-yl)(6-methoxy-[1,2,4]triazolo[4,3-a]pyridin-3-yl)methanone | 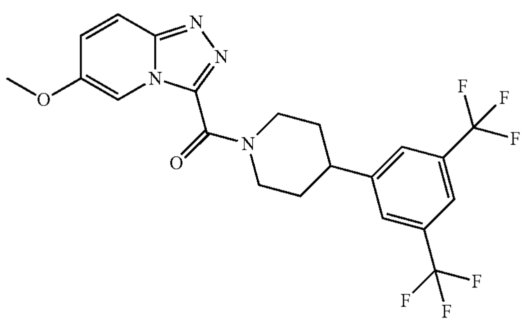 [SMILES: COc1ccc2nnc(C(=O)N3CCC(c4cc(C(F)(F)F)cc(C(F)(F)F)c4)CC3)n2c1] |

TABLE 1-continued

| Compound No. | Name | Structure |
|---|---|---|
| 36 | 3-(4-(2-chloro-5-fluorophenyl)piperidine-1-carbonyl)-[1,2,4]triazolo[4,3-a]pyridine-6-carbonitrile | 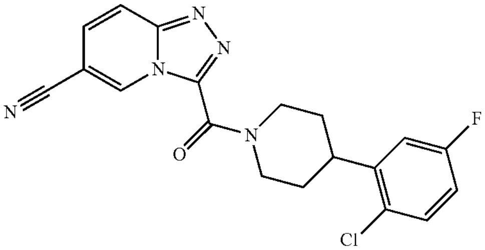 [SMILES: N#Cc1ccc2nnc(C(=O)N3CCC(c4cc(F)ccc4Cl)CC3)n2c1] |
| 37 | 3-(4-(2-fluoro-6-(trifluoromethyl)phenyl)piperidine-1-carbonyl)-[1,2,4]triazolo[4,3-a]pyridine-6-carbonitrile | 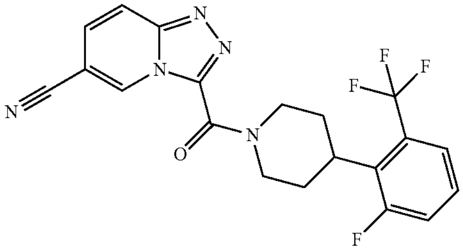 [SMILES: N#Cc1ccc2nnc(C(=O)N3CCC(c4c(F)cccc4C(F)(F)F)CC3)n2c1] |
| 38 | 3-(4-(2-chloro-3-fluorophenyl)piperidine-1-carbonyl)-[1,2,4]triazolo[4,3-a]pyridine-6-carbonitrile | 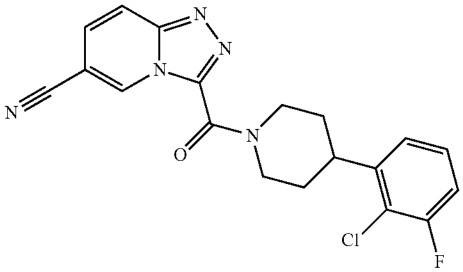 [SMILES: N#Cc1ccc2nnc(C(=O)N3CCC(c4cccc(F)c4Cl)CC3)n2c1] |
| 39 | (6-bromo-[1,2,4]triazolo[4,3-a]pyridin-3-yl)(4-(2-fluoro-6-(trifluoromethyl)phenyl)piperidin-1-yl)methanone | 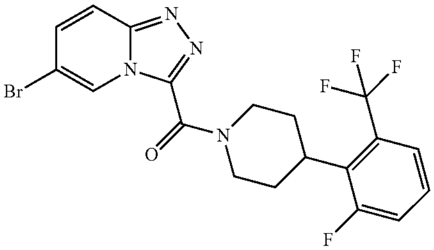 [SMILES: O=C(c1nnc2ccc(Br)cn12)N1CCC(c2c(F)cccc2C(F)(F)F)CC1] |
| 40 | (6-bromo-[1,2,4]triazolo[4,3-a]pyridin-3-yl)(4-(2-chloro-3-fluorophenyl)piperidin-1-yl)methanone | 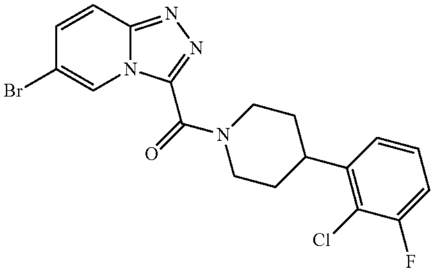 [SMILES: O=C(c1nnc2ccc(Br)cn12)N1CCC(c2cccc(F)c2Cl)CC1] |

TABLE 1-continued

| Compound No. | Name | Structure |
|---|---|---|
| 41 | 3-(4-(3-chloro-2-(trifluoromethyl)phenyl)piperidine-1-carbonyl)-[1,2,4]triazolo[4,3-a]pyridine-6-carbonitrile | 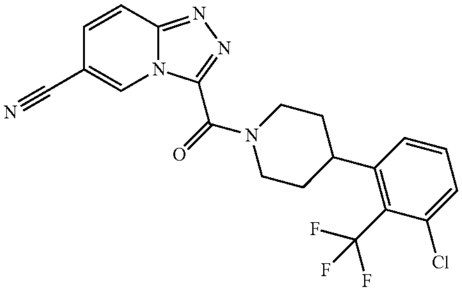 [SMILES: N#Cc1ccc2nnc(C(=O)N3CCC(c4cccc(Cl)c4C(F)(F)F)CC3)n2c1] |
| 42 | 3-(4-(5-chloro-2-(trifluoromethyl)phenyl)piperidine-1-carbonyl)-[1,2,4]triazolo[4,3-a]pyridine-6-carbonitrile | 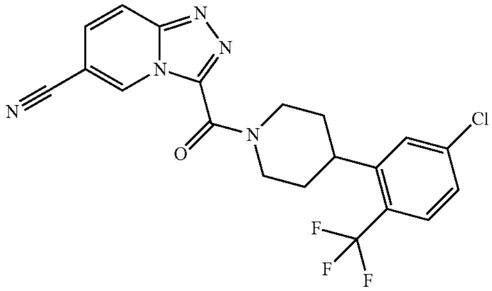 [SMILES: N#Cc1ccc2nnc(C(=O)N3CCC(c4cc(Cl)ccc4C(F)(F)F)CC3)n2c1] |
| 43 | 3-(4-(4-fluoro-2-(trifluoromethyl)phenyl)piperidine-1-carbonyl)-[1,2,4]triazolo[4,3-a]pyridine-6-carbonitrile | 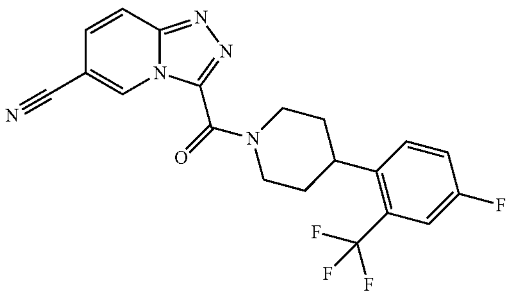 [SMILES: N#Cc1ccc2nnc(C(=O)N3CCC(c4ccc(F)cc4C(F)(F)F)CC3)n2c1] |
| 44 | 3-(4-(3,5-difluoro-2-(trifluoromethyl)phenyl)piperidine-1-carbonyl)-[1,2,4]triazolo[4,3-a]pyridine-6-carbonitrile | 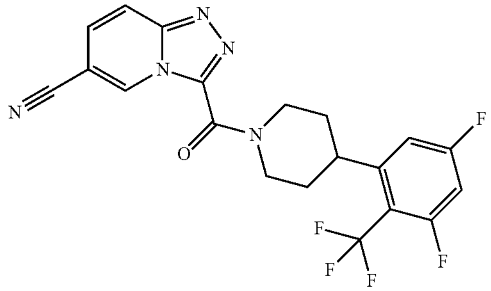 [SMILES: N#Cc1ccc2nnc(C(=O)N3CCC(c4cc(F)cc(F)c4C(F)(F)F)CC3)n2c1] |
| 45 | 3-(4-(5-fluoro-2-(trifluoromethyl)phenyl)piperidine-1-carbonyl)-[1,2,4]triazolo[4,3-a]pyridine-6-carbonitrile | 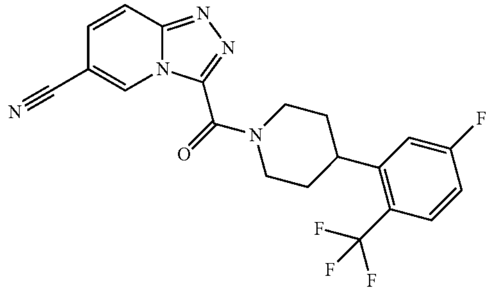 [SMILES: N#Cc1ccc2nnc(C(=O)N3CCC(c4cc(F)ccc4C(F)(F)F)CC3)n2c1] |

TABLE 1-continued

| Compound No. | Name | Structure |
|---|---|---|
| 46 | (6-bromo-[1,2,4]triazolo[4,3-a]pyridin-3-yl)(4-(3-fluoro-2-(trifluoromethyl)phenyl)piperidin-1-yl)methanone | 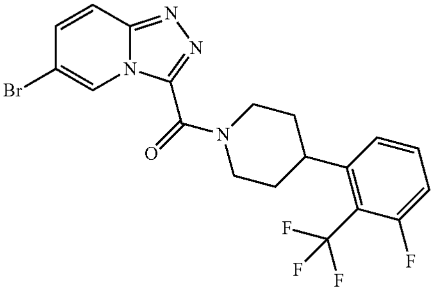 [SMILES: O=C(c1nnc2ccc(Br)cn12)N1CCC(c2cccc(F)c2C(F)(F)F)CC1] |
| 47 | (6-bromo-[1,2,4]triazolo[4,3-a]pyridin-3-yl)(4-(5-chloro-2-(trifluoromethyl)phenyl)piperidin-1-yl)methanone | 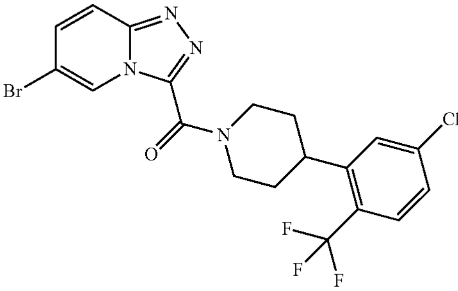 [SMILES: O=C(c1nnc2ccc(Br)cn12)N1CCC(c2cc(Cl)ccc2C(F)(F)F)CC1] |
| 48 | (6-bromo-[1,2,4]triazolo[4,3-a]pyridin-3-yl)(4-(2-chloro-5-fluorophenyl)piperidin-1-yl)methanone | 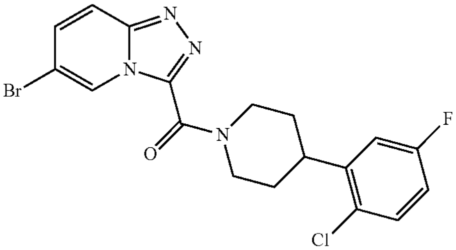 [SMILES: O=C(c1nnc2ccc(Br)cn12)N1CCC(c2cc(F)ccc2Cl)CC1] |

Preparation of Compounds

The compounds used in the chemical reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Alternatively, specific and analogous reactants can be identified through the indices of known chemicals and reactions prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the heterocyclic RBP4 inhibitory compound described herein is P. H. Stahl & C. G. Wermuth "Handbook of Pharmaceutical Salts", Verlag Helvetica Chimica Acta, Zurich, 2002.

Retinol Binding Protein 4 (RBP4)

Retinol-binding protein 4 (RBP4), the sole retinol transporter in blood, is secreted from adipocytes and liver. Serum RBP4 levels correlate highly with insulin resistance, other metabolic syndrome factors, and cardiovascular disease. In some instances, elevated serum RBP4 causes insulin resistance and impaired glucose tolerance. In some instances, lowering of serum RBP4 improves insulin action and glucose tolerance. In some embodiments, the compounds described herein lower serum or plasma RBP4 and thus improve insulin action and glucose tolerance.

In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 24 hours after administration of a compound of Formula (I), a pharmaceutically acceptable salt, solvate, poly morph, prodrug, metabolite, N-oxide, stereoisomer, or isomer thereof, the serum or plasma levels of RBP4 are reduced by at least 80% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 20% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 25% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

Methods of Treatment

In some embodiments, a compound disclosed herein is used to treat or ameliorate a disease associated with altered RBP4 pathways when administered to a subject in need thereof. In some cases, a compound disclosed herein is used to treat or ameliorate the effects of a disease associated with altered RBP4 pathway when administered to a subject in need thereof. Exemplary diseases associated with altered RBP4 include metabolic diseases. In some instances, a compound disclosed herein is used to treat or ameliorate a metabolic disease when administered to a subject in need thereof. Exemplary metabolic diseases include NASH, NAFLD, type II diabetes, diabetic retinopathy, obesity, fibrosis, cirrhosis, or liver cancer. In one embodiment, the fatty liver disease is selected from the group consisting of non-alcoholic fatty acid liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases, Weber-Christian disease, Wolmans disease, acute fatty liver of pregnancy, and lipodystrophy. Heterocyclic RBP4 inhibitory compounds disclosed herein are in some embodiments used to modulate various protein levels which result in improved disease outcomes. For example, proteins variously include cytokines or other protein. In some embodiments, a compound described herein provides for a decrease in an inflammatory cytokine. In some embodiments, a heterocyclic RBP4 inhibitory compound described herein provides for a decrease in IL6, MCP, TNF-α, or any combination thereof. In some embodiments, the heterocyclic RBP4 inhibitory compounds described herein provide a decrease in IL6. In some embodiments, the heterocyclic RBP4 inhibitory compounds described herein provide a decrease in MCP. In some embodiments, the heterocyclic RBP4 inhibitory compounds described herein provide a decrease in TNF-α.

Non-Alcoholic Steatohepatitis (NASH)

Non-alcoholic steatohepatitis or NASH is a common liver disease, which resembles alcoholic liver disease, but occurs in people who drink little or no alcohol. The major feature in NASH is fat in the liver, along with inflammation and damage. In some instances, NASH progresses into advanced NASH, which is characterized, inter cilia, by hepatic fibrosis. In certain instances, NASH progresses to cirrhosis, in which the liver is damaged, scarred, and is no longer able to work properly. In some instances, a person with cirrhosis experiences fluid retention, muscle wasting, bleeding from the intestines, and/or liver failure. In some instances. NASH is associated with an increased risk of cardiovascular mortality and type II diabetes mellitus. Cirrhosis due to NASH increases the risk of hepatocellular carcinoma.

NASH is usually first suspected in a person who is found to have elevations in liver tests that are included in routine blood test panels, such as alanine aminotransferase (ALT) or aspartate aminotransferase (AST). When further evaluation shows no apparent reason for liver disease (such as medications, viral hepatitis, or excessive use of alcohol) and when X-rays or imaging studies of the liver show fat, NASH is suspected. NASH is diagnosed and separated from NAFLD by a liver biopsy. For a liver biopsy, a needle is inserted through the skin to remove a small piece of the liver. NASH is diagnosed when examination of the tissue with a microscope shows fat along with inflammation and damage to liver cells. A biopsy can provide information about scar tissue has development in the liver.

Some embodiments provided herein describe the use of the heterocyclic RBP4 inhibitory compounds described herein for treating NASH in a subject in need thereof. In some embodiments, the heterocyclic RBP4 inhibitory compounds inhibit NASH. In specific embodiments, the heterocyclic RBP4 inhibitory compounds arrest the development of NASH or its clinical symptoms. In other embodiments, the heterocyclic RBP4 inhibitory compounds reduce the development of NASH or its clinical symptoms. In certain embodiments, the heterocyclic RBP4 inhibitory compounds relieve the subject of NASH. In specific embodiments, the heterocyclic RBP4 inhibitory compounds cause regression, reversal or amelioration of NASH. In certain specific embodiments, the heterocyclic RBP4 inhibitory compounds reduce the number, frequency, duration, or severity of NASH clinical symptoms. In some embodiments, an RBP4 inhibitory compound described herein provide a reduction in NASH fibrosis scores. In some embodiments, an RBP4 inhibitory compound described herein provide a decrease in the number of bridging fibrosis. In some embodiments, the heterocyclic RBP4 inhibitory compounds are used prophylactically. In specific embodiments, the heterocyclic RBP4 inhibitory compounds are used to prevent or reduce the risk of developing NASH. In certain specific embodiments, the heterocyclic RBP4 inhibitory compounds cause the clinical symptoms of NASH not to develop in a subject who may be predisposed to NASH but who does not yet experience or display symptoms of NASH.

Non-Alcoholic Fatty Liver Disease (NAFLD)

Non-alcoholic fatty liver disease (NAFLD) is a disorder affecting as many as 1 in 3-5 adults and 1 in 10 children in the United States, and refers to conditions where there is an accumulation of excess fat in the liver of people who drink little or no alcohol. The most common form of NAFLD is a non-serious condition called hepatic steatosis (fatty liver), in which fat accumulates in the liver cells. NAFLD most often presents itself in individuals with a constellation of risk factors called the metabolic syndrome, which is characterized by elevated fasting plasma glucose (FPG) with or without intolerance to post-prandial glucose, being overweight or obese, high blood lipids such as cholesterol and triglycerides (TGs) and low high-density lipoprotein cholesterol (HDL-C) levels, and high blood pressure; but not all patients have all the manifestations of the metabolic syndrome. Obesity is thought to be the most common cause of NAFLD; and some experts estimate that about two-thirds of obese adults and one-half of obese children may have fatty liver. The majority of individuals with NAFLD have no symptoms and a normal physical examination (although the liver may be slightly enlarged); children may exhibit symptoms such as abdominal pain and fatigue, and may show patchy dark skin discoloration (acanthosis nigricans). The diagnosis of NAFLD is usually first suspected in an overweight or obese person who is found to have mild elevations in their liver blood tests during routine testing, though NAFLD can be present with normal liver blood tests, or incidentally detected on imaging investigations such as abdominal ultrasound or CT scan. It is confirmed by imaging studies, most commonly a liver ultrasound or magnetic resonance imaging (MRI), and exclusion of other causes.

Some embodiments provided herein describe the use of the heterocyclic RBP4 inhibitory compounds described herein for treating NAFLD in a subject in need thereof. In some embodiments, the heterocyclic RBP4 inhibitory compounds inhibit NAFLD. In specific embodiments, the heterocyclic RBP4 inhibitory compounds arrest the development of NAFLD or its clinical symptoms. In other embodiments, the heterocyclic RBP4 inhibitory compounds reduce the development of NAFLD or its clinical symptoms. In certain embodiments, the heterocyclic RBP4 inhibitory compounds relieve the subject of NAFLD. In specific embodiments, the heterocyclic RBP4 inhibitory compounds cause regression, reversal or amelioration of NAFLD. In certain specific embodiments, the heterocyclic RBP4 inhibitory compounds reduce the number, frequency, duration, or severity of NAFLD clinical symptoms.

In some embodiments, the heterocyclic RBP4 inhibitory compounds are used prophylactically. In specific embodiments, the heterocyclic RBP4 inhibitory compounds are used to prevent or reduce the risk of developing NAFLD. In certain specific embodiments, the heterocyclic RBP4 inhibitory compounds cause the clinical symptoms of NAFLD not to develop in a subject who may be predisposed to NAFLD but who does not yet experience or display symptoms of NAFLD.

Type II Diabetes

Type II diabetes is a metabolic disorder characterized by hyperglycemia and abnormities in the glucose-protein- and lipid-metabolism. Type II diabetes is caused by insulin resistance which is not adequately compensated due to an insufficient β-cell secretory capacity. In recent years, type II diabetes and its chronic complications have become a major threat to human health. Long-term hyperglycemia associated with type II diabetes results in the damage of many tissues and organs, which in turn leads to a variety of diabetic chronic complications, such as coronary heart disease, atherosclerosis, cerebrovascular disease and other diabetic macrovascular diseases, diabetic nephropathy, diabetic retinopathy and other diabetic microangiopathy, diabetic neuropathy, diabetic foot, diabetic maculopathy, diabetic cataract, diabetic glaucoma, refractive changes, iris and ciliary body diseases.

Some embodiments provided herein describe the use of the heterocyclic RBP4 inhibitory compounds described herein for treating type II diabetes, including its chronic complications, in a subject in need thereof. In some embodiments, the heterocyclic RBP4 inhibitory compounds inhibit type II diabetes, including its chronic complications. In specific embodiments, the heterocyclic RBP4 inhibitory compounds arrest the development of type II diabetes, its chronic complications, or its clinical symptoms. In other embodiments, the heterocyclic RBP4 inhibitory compounds reduce the development of type II diabetes, its chronic complications, or its clinical symptoms. In certain embodiments, the heterocyclic RBP4 inhibitory compounds relieve the subject of type II diabetes, its chronic complications, or its clinical symptoms. In specific embodiments, the heterocyclic RBP4 inhibitory compounds cause regression, reversal, or amelioration of type II diabetes, its chronic complications, or its clinical symptoms. In certain specific embodiments, the heterocyclic RBP4 inhibitory compounds reduce the number, frequency, duration, or severity of type II diabetes, its chronic complications, or its clinical symptoms.

In some embodiments, the heterocyclic RBP4 inhibitory compounds are used prophylactically. In specific embodiments, the heterocyclic RBP4 inhibitory compounds are used to prevent or reduce the risk of type II diabetes, its chronic complications, or its clinical symptoms. In certain specific embodiments, the heterocyclic RBP4 inhibitory compounds cause the clinical symptoms of type II diabetes not to develop in a subject who may be predisposed to type II diabetes but who does not yet experience or display symptoms of type II diabetes. In some embodiments, the subject is genetically, environmentally, dietarily or socially predisposed to type II diabetes.

Obesity

Obesity and disorders associated with obesity such as diabetes are a major global health concern. Obesity, which is generally associated with an abnormal accumulation of fat cells, develops when energy intake exceeds energy expenditure.

Obesity is associated with an increased risk of diabetes. Most obese people are insulin resistant and have to adapt by increasing insulin secretion. In some instances, type II diabetes mellitus manifests in individuals who lose the ability to produce sufficient quantities of insulin to maintain normoglycemia in the face of insulin resistance.

Obesity is a state of chronic, low-grade inflammation, and macrophages are thought to play an important role in maintaining this state in adipose tissue. Many molecules secreted by adipose tissue promote adipose tissue inflammation. Emerging evidence suggests a possible role for proinflammatory pathways in RBP4-induced insulin resistance. RBP4 expression in adipose tissue and serum RBP4 levels strongly correlate with subclinical inflammation, including serum levels and adipose tissue expression of proinflammatory cytokines.

Some embodiments provided herein describe the use of the heterocyclic RBP4 inhibitory compounds described herein for treating obesity in a subject in need thereof. In specific embodiments, the heterocyclic RBP4 inhibitory compounds arrest the development of obesity or its clinical symptoms. In other embodiments, the heterocyclic RBP4 inhibitory compounds reduce the development of obesity or its clinical symptoms. In certain embodiments, the heterocyclic RBP4 inhibitory compounds relieve the subject of obesity. In specific embodiments, the heterocyclic RBP4 inhibitory compounds cause regression, reversal or amelioration of obesity. In certain specific embodiments, the heterocyclic RBP4 inhibitory compounds reduce the number, frequency, duration, or severity of obesity clinical symptoms.

In some embodiments, the heterocyclic RBP4 inhibitory compounds are used prophylactically. In specific embodiments, the heterocyclic RBP4 inhibitory compounds are used to prevent or reduce the risk of developing obesity. In certain specific embodiments, the heterocyclic RBP4 inhibitory compounds cause the clinical symptoms of obesity not to develop in a subject who may be predisposed to obesity but who does not yet experience or display symptoms of obesity. In some embodiments, a heterocyclic RBP4 inhibitory compound improves plasma insulin levels. In some embodiments, a heterocyclic RBP4 inhibitory compound improves glucose tolerance levels.

Pharmaceutical Compositions

In certain embodiments, the heterocyclic RBP4 inhibitory compound as described herein is administered as a pure chemical. In other embodiments, the heterocyclic RBP4 inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

Provided herein is a pharmaceutical composition comprising at least one heterocyclic RBP4 inhibitory compound, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising a compound of Formula (I), or a pharmaceutically acceptable salt thereof, and a pharmaceutically acceptable excipient. In one embodiment, the pharmaceutical compositions are provided in a dosage form for oral administration, which comprise a compound provided herein, and one or more pharmaceutically acceptable excipients or carriers.

In certain embodiments, the heterocyclic RBP4 inhibitory compound as described by Formula (I) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, $21^{st}$ Ed. Mack Pub. Co., Easton, PA (2005)).

In some embodiments, the pharmaceutical compositions provided herein are formulated for oral administration in tablet, capsule, powder, or liquid form. In some embodiments, a tablet comprises a solid carrier or an adjuvant. Liquid pharmaceutical compositions generally comprise a liquid carrier such as water, petroleum, animal or vegetable oils, mineral oil, or synthetic oil. In some embodiments, physiological saline solution, dextrose or other saccharide solution, or glycols are optionally included. In some embodiments, a capsule comprises a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions are formulated for intravenous, cutaneous or subcutaneous injection, the active ingredient is in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, buffers, antioxidants, and/or other additives are included.

In yet another embodiment, the pharmaceutical compositions are provided in a dosage form for topical administration, which comprise a compound provided herein, and one or more pharmaceutically acceptable excipients or carriers.

Methods of Dosing and Treatment Regimens

The dose of the composition comprising at least one heterocyclic RBP4 inhibitory compound as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, in which the mammal previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Oral doses typically range from about 1.0 mg to about 1000 mg, one to four times, or more, per day. In general, however, doses employed for adult human treatment are typically in the range of 0.01 mg to 5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 225 mg, about 240 mg, about 250 mg, about 275 mg, about 300 mg, about 325 mg, about 350 mg, about 375 mg, about 400 mg, about 425 mg, about 450 mg, about 475 mg, or about 500 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to about 15 mg, up to about 20 mg, up to about 25 mg, up to about 30 mg, up to about 35 mg, up to about 40 mg, up to about 45 mg, up to about 50 mg, up to about 55 mg, up to about 60 mg, up to about 65 mg, up to about 70 mg, up to about 75 mg, up to about 80 mg, up to about 85 mg, up to about 90 mg, up to about 95 mg, up to about 100 mg, up to about 105 mg, up to about 110 mg, up to about 115 mg, up to about 120 mg, up to about 125 mg, up to about 130 mg, up to about 135 mg, up to about 140 mg, up to about 145 mg, up to about 150 mg, up to about 155 mg, up to about 160 mg, up to about 165 mg, up to about 170 mg, up to about 175 mg, up to about 180 mg, up to about 185 mg, up to about 190 mg, up to about 195 mg, up to about 200 mg, up to about 225 mg, up to about 240 mg, up to about 250 mg, up to about 275 mg, up to about 300 mg, up to about 325 mg, up to about 350 mg, up to about 375 mg, up to about 400 mg, up to about 425 mg, up to about 450 mg, up to about 475 mg, or up to about 500 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, at least 240 mg, at least 250 mg, at least 275 mg, at least 300 mg, at least 325 mg, at least 350 mg, at least 375 mg, at least 400 mg, at least 425 mg, at least 450 mg, at least 475 mg, or at least 500 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 25 mg, about 50 mg, about 75 mg, about 100 mg, about 150 mg about 200 mg, or about 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 50 mg, about 100 mg, about 150 mg, about 200 mg, or about 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg, up to 50 mg, up to 75 mg, up to 100 mg, up to 150 mg, up to 200 mg, or up to 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least 25 mg, at least 50 mg, at least 75 mg, at least 100 mg, at least 150 mg, at least 200 mg, or at least 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg, up to 50 mg, up to 75 mg, up to 100 mg, up to 150 mg, up to 200 mg, up to 400 mg, up to 600 mg, up to 800 mg, or up to 1000 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 25 mg per day, about 50 mg per day, about 75 mg per day, about 100 mg per day, about 150 mg per day, about 200 mg per day, or about 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 50 mg per day, about 100 mg per day, about 150 mg per day, about 200 mg per day, or about 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg per day, up to 50 mg per day, up to 75 mg per day, up to 100 mg per day, up to 150 mg per day, up to 200 mg per day, or up to 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least 25 mg per day, at least 50 mg per day, at least 75 mg per day, at least 100 mg per day, at least 150 mg per day, at least 200 mg per day, or at least 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg per day, up to 50 mg per day, up to 75 mg per day, up to 100 mg per day, up to 150 mg per day, up to 200 mg per day, up to 400 mg per day, up to 600 mg per day, up to 800 mg per day, or up to 1000 mg per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of up to 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 200 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 150 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 100 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 75 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 50 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of up to 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 200 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 150 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 100 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 75 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 50 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 200 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 150 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 100 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 75 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 50 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 25 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 200 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 150 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 100 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 75 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 50 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 25 mg per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 200 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 150 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 100 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 75 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 50 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 25 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 200 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 150 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 100 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 75 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 50 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 25 mg per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal. In some embodiments, a compound of Formula (I), a pharmaceutically acceptable salt, solvate, polymorph, prodrug, metabolite, N-oxide, stereoisomer, or isomer thereof is administered orally or parenterally to the subject in need thereof. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration. In some embodiments, a compound of Formula (I), a pharmaceutically acceptable salt, solvate, polymorph, prodrug, metabolite, N-oxide, stereoisomer, or isomer thereof is administered orally or intravenously to a subject in need thereof. In some embodiments, a compound of Formula (I), a pharmaceutically acceptable salt, solvate, polymorph, prodrug, metabolite, N-oxide, stereoisomer, or isomer thereof is administered orally to a subject in need thereof. In some embodiments, a compound of Formula (I), a pharmaceutically acceptable salt, solvate, polymorph, prodrug, metabolite, N-oxide, stereoisomer, or isomer thereof is administered intravenously to a subject in need thereof.

In any of the aforementioned aspects are further embodiments comprising single administrations of the effective amount of the compound, including further embodiments in which (i) the compound is administered once a day; or (ii) the compound is administered to the mammal multiple times over the span of one day, e.g., two, three, four or more times daily. In some embodiments, the heterocyclic RBP4 inhibitory compounds described herein are administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some embodiments, the heterocyclic RBP4 inhibitory compounds described herein, or a pharmaceutically acceptable salt, solvate, polymorph, prodrug, metabolite, N-oxide, stereoisomer, or isomer thereof, are administered daily.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours.

In certain embodiments wherein a patient's status does improve, the dose of drug being administered is temporarily reduced or temporarily suspended for a certain length of time (e.g., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 7 days. In one embodiment, the length of the drug holiday is 7 days. In one embodiment, the length of the drug holiday is 14 days. In one embodiment, the length of the drug holiday is 28 days.

Provided herein are methods for the treatment of obesity, diabetes, non-alcoholic fatty liver disease, or non-alcoholic steatohepatitis with heterocyclic derivative compounds and pharmaceutical compositions thereof.

Some embodiments provided herein describe methods of treating a metabolic disease or disorder in a subject in need thereof, the method comprising administering to the subject a composition comprising a therapeutically effective amount of a compound of Formula (I), a pharmaceutically acceptable salt, solvate, polymorph, prodrug, metabolite, N-oxide, stereoisomer, or isomer thereof:

Formula (I)

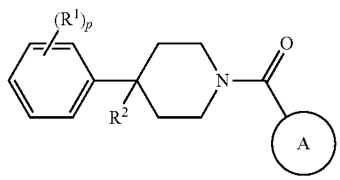

wherein:

each $R^1$ is independently halogen, haloalkyl, or alkyl;

$R^2$ is —H, —OH, or halogen;

p is 0, 1, 2, 3, 4, or 5,

A has the structure:

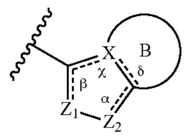

wherein:

α, β, χ, and δ are each independently absent or present, and when present each is a bond;

X is N;

$Z_1$ is S, O, or N;

$Z_2$ is S, O, N, or $NR^3$;

$R^3$ is H, $C_1$-$C_4$ alkyl, or oxetane; and

B is a substituted or unsubstituted fused 5-, 6-, or 7-membered ring structure.

In some embodiments of a compound of Formula (I), when α is present, then $Z_1$ and $Z_2$ are N, X is N, β is present, and χ and δ are absent.

In some embodiments of a method of treating a metabolic disease or disorder comprising a compound of Formula (I), A has the structure

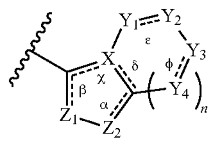

wherein:

n is 0, 1, or 2;

α, β, χ, δ, ε, and ϕ are each independently absent or present, and when present each is a bond;

$Z_1$ is S, O, or N;

$Z_2$ is S, O, N or $NR^3$, wherein $R^3$ is 1, $C_1$-$C_4$ alkyl, or oxetane;

X is N;

$Y_1$, $Y_2$, $Y_3$ and each occurrence of $Y_4$ are each independently $CR^4$, $C(R^5)_2$, $NR^6$, O, N, $SO_2$, or —(C═O)—, wherein:

each $R^4$ is independently H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$alkyl)$_2$, —$SO_2$NH($C_1$-$C_{10}$ alkyl), —$SO_2$N($C_1$-$C_{10}$ alkyl)$_2$, —CN, or —$CF_3$;

each $R^5$ is independently H or $C_1$-$C_{10}$ alkyl; and each $R^6$ is independently H, $C_1$-$C_{10}$ alkyl, $C_3$-$C_6$ cycloalkyl, —($C_1$-$C_{10}$ alkyl)$CF_3$, —($C_1$-$C_{10}$ alkyl)$OCH_3$, —($C_1$-$C_{10}$ alkyl)-halogen, —$SO_2$($C_1$-$C_{10}$ alkyl), —$SO_2$($C_1$-$C_{10}$ alkyl)-$CF_3$, —$SO_2$($C_1$-$C_{10}$ alkyl)$OCH_3$, —$SO_2$($C_1$-$C_{10}$ alkyl)-halogen, —C(O)($C_1$-$C_{10}$ alkyl), —C(O)($C_1$-$C_{10}$ alkyl)$CF_3$, —C(O)($C_1$-$C_{10}$ alkyl)$OCH_3$, —C(O)($C_1$-$C_{10}$ alkyl)-halogen, —C(O)NH($C_1$-$C_{10}$ alkyl), —C(O)N($C_1$-$C_{10}$ alkyl)$_2$, —($C_1$-$C_{10}$ alkyl)C(O)OH, —C(O)$NH_2$, or oxetane.

In some embodiments of a compound of Formula (I), when α is present, then $Z_1$ and $Z_2$ are N, X is N, β is present, and λ and δ are absent; when ε and ϕ are each present, then n=1, and each of $Y_1$, $Y_2$, $Y_3$, and $Y_4$, are independently —$CR^4$— or N; or when ε and ϕ are each absent, then n=0, 1 or 2, each of $Y_1$, $Y_2$, $Y_3$, and each occurrence of $Y_4$ are independently $C(R^5)_2$, $NR^6$, O, or $SO_2$.

In some embodiments of a compound of Formula (I), where in a, p, ε, and ϕ are present; χ and δ are absent; $Z_1$ is N; $Z_2$ is N; and X is N.

In some embodiments of a method of treating a metabolic disease or disorder comprising a compound of Formula (I). A has the structure:

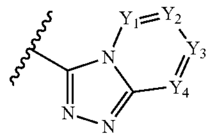

wherein:

$Y_1$, $Y_2$, $Y_3$ and $Y_4$ are each independently $CR_4$ or N; and each $R^4$ is independently H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$.

In some embodiments of a method of treating a metabolic disease or disorder comprising a compound of Formula (I), A has the structure.

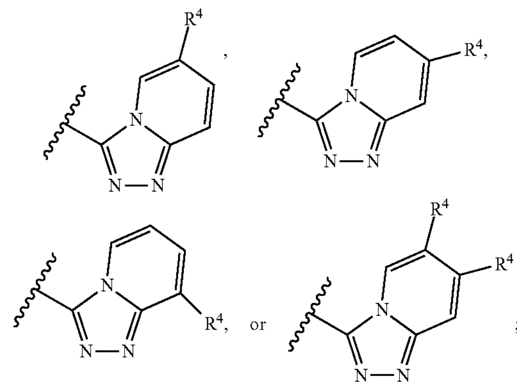

, , , or ;

wherein:

each $R_4$ is independently H, halogen, $C_1$-$C_4$ alkyl, $C_3$-$C_6$ cycloalkyl, —O($C_1$-$C_4$ alkyl), —CN, —$CF_3$, —C(O)OH, —C(O)$NH_2$, —C(O)N$(CH_3)_2$, —C(O)$NHCH_3$, or —NHC(O)N$(CH_3)_2$.

In some embodiments of a method of treating a metabolic disease or disorder comprising a compound of Formula (I), each $R^1$ is independently F, Br, Cl, $C_{1-6}$ haloalkyl, or $C_{1-6}$ alkyl.

In some embodiments of a method of treating a metabolic disease or disorder comprising a compound of Formula (I), wherein each $R^1$ is independently F or $CF_3$.

One embodiment provides a method of treating a metabolic disease or disorder in a subject in need thereof, the method comprising administering to the subject a composition comprising a therapeutically effective amount of a compound having the structure:

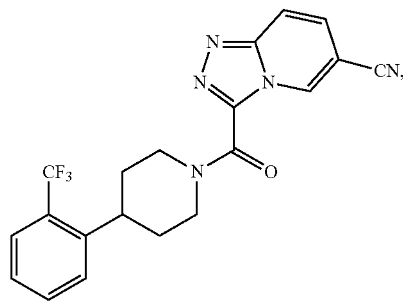 [SMILES: N#Cc1ccc2nnc(C(=O)N3CCC(c4ccccc4C(F)(F)F)CC3)n2c1]

or a pharmaceutically acceptable salt, solvate, polymorph, prodrug, metabolite, N-oxide, stereoisomer, or isomer thereof.

One embodiment provides a method of treating a metabolic disease or disorder in a subject in need thereof, the method comprising administering to the subject a composition comprising a therapeutically effective amount of a compound having the structure:

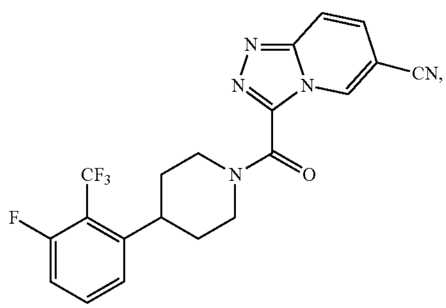 [SMILES: N#Cc1ccc2nnc(C(=O)N3CCC(c4cccc(F)c4C(F)(F)F)CC3)n2c1]

or a pharmaceutically acceptable salt, solvate, polymorph, prodrug, metabolite, N-oxide, stereoisomer, or isomer thereof.

In some embodiments, the metabolic disease or disorder is obesity, type 11 diabetes, diabetic retinopathy, non-alcoholic fatty liver disease (NAFLD), non-alcoholic steatohepatitis (NASH), liver fibrosis, liver cancer, or liver cirrhosis.

In some embodiments, the therapeutically effective amount of a compound of Formula (I), a pharmaceutically acceptable salt, solvate, polymorph, prodrug, metabolite, N-oxide, stereoisomer, or isomer thereof is about 25 mg per day, about 50 mg per day, about 75 mg per day, about 100 mg per day, about 150 mg per day, about 200 mg per day, or about 400 mg per day.

In some embodiments, the therapeutically effective amount of a compound of Formula (I), a pharmaceutically acceptable salt, solvate, polymorph, prodrug, metabolite, N-oxide, stereoisomer, or isomer thereof is about 50 mg per day, about 100 mg per day, about 150 mg per day, about 200 mg per day, or about 400 mg per day. In some embodiments, the therapeutically effective amount of a compound of Formula (I), a pharmaceutically acceptable salt, solvate, polymorph, prodrug, metabolite, N-oxide, stereoisomer, or isomer thereof is up to 25 mg per day, up to 50 mg per day, up to 75 mg per day, up to 100 mg per day, up to 150 mg per day, up to 200 mg per day, or up to 400 mg per day. In some embodiments, the therapeutically effective amount of a compound of Formula (I), a pharmaceutically acceptable salt, solvate, polymorph, prodrug, metabolite, N-oxide, stereoisomer, or isomer thereof is up to 400 mg per day.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, the disease or disorder is obesity. In some embodiments, the disease or disorder is type II diabetes. In some embodiments, the disease or disorder is non-proliferative diabetic retinopathy (NPDR) or proliferative diabetic retinopathy (PDR). In some embodiments, the disease or disorder is a liver disease. In some embodiments, the disease or disorder is non-alcoholic fatty liver disease (NAFLD). In some embodiments, the disease or disorder is non-alcoholic steatohepatitis (NASH). In some embodiments, the disease or disorder is liver fibrosis. In some embodiments, the disease or disorder is liver cirrhosis. In some embodiments, the disease or disorder is liver cancer.

In some embodiments of a method of treating a metabolic disorder, the compound is administered to the subject orally or intravenously. In certain embodiments, the compound of Formula (I) is administered orally. In certain embodiments, the compound of Formula (I) is administered intravenously. In some embodiments, the administration is to treat an existing disease or disorder. In some embodiments, the administration is provided as prophylaxis.

EXAMPLES

Example 1: Compound 1 Single Dose Rat PK Study

A pharmacokinetic study of Compound 1 following a single intravenous or oral dose administration to male Sprague Dawley rats was conducted, the results of which are found in Table 2 and FIGS. 1-6.

TABLE 2

| Rat # | $T_{max}$ (hr)[a] | $C_{max}$ (ng/ml) | $t_{1/2}$ (hr) | $AUC_{LAST}$ (hr · ng/ml) | $AUC_{inf}$ (hr · ng/ml) | Cl (ml/hr/kg) | $V_{ss}$ (ml/kg) | $MRT_{last}$ (hr) | F (%) |
|---|---|---|---|---|---|---|---|---|---|
| iv, 2 mg/kg | | | | | | | | | |
| 1 | 0.083 | 2365 | 6.2 | 2768 | 2781 | 719 | 1932 | 2.5 | NA |
| 2 | 0.083 | 1595 | 8.6 | 2429 | 2465 | 812 | 2756 | 2.7 | NA |
| 3 | 0.083 | 2380 | 6.1 | 2711 | 2722 | 735 | 1922 | 2.4 | NA |
| Mean | 0.083 | 2113 | 7.0 | 2636 | 2656 | 755 | 2203 | 2.6 | NA |
| SD | 0.000 | 449 | 1.4 | 181 | 168 | 49 | 479 | 0.2 | |
| po, 5 mg/kg | | | | | | | | | |
| 4 | 1.00 | 227 | 6.4 | 1845 | 1858 | NC | NC | 7.9 | 28.0 |
| 5 | 1.00 | 548 | 5.4 | 2953 | 2961 | NC | NC | 5.1 | 44.6 |
| 6 | 1.00 | 455 | 6.1 | 3646 | 3663 | NC | NC | 8.0 | 55.2 |
| Mean | 1.00 | 410 | 6.0 | 2815 | 2827 | NC | NC | 7.0 | 42.6 |
| SD | 0.00 | 165 | 0.5 | 908 | 910 | | | 1.6 | 13.7 |

[a] For the iv group, the first plasma collection time is listed as the $T_{max}$;
NA = not applicable;
NC = not calculated.

Example 2: Compound 1 Single Dose Mouse PK Study

A pharmacokinetic study of Compound 1 following a single intravenous or oral dose administration to male CD-1 mice was conducted, the results of which are found in Table 3 and FIGS. 7-12.

TABLE 3

| Route | Dose (mg/kg) | $T_{max}$ (hr) | $C_{max}$ (ng/ml)[a] | $t_{1/2}$ (hr) | $AUC_{LAST}$ (hr · ng/ml) | $AUC_{inf}$ (hr · ng/ml) | Cl (ml/hr/kg) | $V_{ss}$ (ml/kg) | $MRT_{last}$ (hr) | $MRT_{inf}$ (hr) | F (%) |
|---|---|---|---|---|---|---|---|---|---|---|---|
| iv | 2 | 0.083[b] | 2973 | 5.7 | 12197 | 12232 | 163.5 | 1123 | 6.7 | 6.9 | NA[c] |
| po | 5 | 2 | 1590 | 4.7 | 16402 | 16418 | NA | NA | 7.2 | 7.3 | 53.7 |

[a] Maximum observed concentration at first time point;
[b] First plasma collection time;
[c] NA = not applicable.

Example 3: Compound 1 Single Dose Dog PK Study

A pharmacokinetic study of Compound 1 following a single intravenous or oral dose administration to male beagle dogs was conducted, the results of which are found in Table 4 and FIGS. 13-18.

TABLE 4

| Animal # | $T_{max}$ (hr)[a] | $C_{max}$ (ng/ml) | $t_{1/2}$ (hr)[b] | $AUC_{LAST}$ (hr · ng/ml) | $AUC_{inf}$ (hr · ng/ml) | Cl (ml/hr/kg) | $V_{ss}$ (ml/kg) | $MRT_{last}$ (hr) | $MRT_{inf}$ (hr) | F (%) |
|---|---|---|---|---|---|---|---|---|---|---|
| iv, 0.5 mg/kg | | | | | | | | | | |
| 1 | 0.083 | 326 | NC | 7233 | NC | NC | NC | NC | NC | NA |
| 2 | 0.083 | 380 | NC | 7530 | NC | NC | NC | NC | NC | NA |
| 3 | 0.250 | 308 | NC | 6556 | NC | NC | NC | NC | NC | NA |
| Mean | 0.139 | 338 | | 7106 | | | | | | NA |
| SD | 0.096 | 37 | | 500 | | | | | | |

TABLE 4-continued

| Animal # | $T_{max}$ (hr)[a] | $C_{max}$ (ng/ml) | $t_{1/2}$ (hr)[b] | $AUC_{LAST}$ (hr · ng/ml) | $AUC_{inf}$ (hr · ng/ml) | Cl (ml/hr/kg) | $V_{ss}$ (ml/kg) | $MRT_{last}$ (hr) | $MRT_{inf}$ (hr) | F (%) |
|---|---|---|---|---|---|---|---|---|---|---|
| po, 2 mg/kg | | | | | | | | | | |
| 4 | 0.25 | 279 | NC | 7892 | NC | NC | NC | NC | NC | 27.8 |
| 5 | 1.00 | 293 | NC | 8155 | NC | NC | NC | NC | NC | 28.7 |
| 6 | 1.00 | 243 | NC | 8380 | NC | NC | NC | NC | NC | 29.5 |
| Mean | 0.75 | 272 | | 8142 | | | | | | 28.6 |
| SD | 0.43 | 26 | | 244 | | | | | | 0.9 |

[a]For the iv group, the first plasma collection time is typically listed as the $T_{max}$;
[b]Terminal phase parameters could not be calculated because plasma levels did not decrease steadily from the $T_{max}$;
NA = not applicable;
NC = not calculated.

Example 4: Compound 2 Single Dose Rat PK Study

A pharmacokinetic study of Compound 2 following a single intravenous or oral dose administration to male Sprague Dawley rats was conducted, the results of which are found in Table 5 and FIGS. 19-24.

TABLE 5

| Rat #[a] | Dose (mg/kg) | $T_{max}$ (hr)[b] | $C_{max}$ (ng/ml) | $t_{1/2}$ (hr) | $AUC_{LAST}$ (hr · ng/ml) | $AUC_{inf}$ (hr · ng/ml) | Cl (ml/hr/kg) | $V_{ss}$ (ml/kg) | $MRT_{last}$ (hr) | $MRT_{inf}$ (hr) | F (%)[c] |
|---|---|---|---|---|---|---|---|---|---|---|---|
| iv route | | | | | | | | | | | |
| 1 | 1 | 0.083 | 528 | 12.8 | 769 | 798 | 1254 | 10170 | 5.92 | 8.11 | NA |
| 2 | 2 | 0.083 | 1494 | 9.99 | 1744 | 1763 | 1134 | 4218 | 3.06 | 3.72 | NA |
| po route | | | | | | | | | | | |
| 4 | 5 | 1.00 | 160 | 10.77 | 1504 | 1548 | NC | NC | 9.22 | 10.77 | 35 |
| 5 | 5 | 2.00 | 189 | 10.29 | 2038 | 2125 | NC | NC | 9.82 | 12.01 | 48 |
| Mean | | 1.50 | 175 | 10.53 | 1771 | 1837 | NC | NC | 9.52 | 11.39 | 42 |

[a]Rat #3 died immediately after dose of 2 mg/kg; Rat #1 was administered a lower dose, 1 mg/kg;
[b]For the iv group, the first plasma collection time is listed as the $T_{max}$;
[c]Bioavailability (F) was determined using $AUC_{inf}$ for determined using 2 mg/kg (Rat #2);
NA = not applicable.

Example 5: Compound 2 Single Dose Mouse PK Study

A pharmacokinetic study of Compound 2 following a single intravenous or oral dose administration to male CD-1 mice was conducted, the results of which are found in Table 6 and FIGS. 25-31.

TABLE 6

| Route | Dose (mg/kg) | $T_{max}$ (hr)[b] | $C_{max}$ (ng/ml) | $t_{1/2}$ (hr) | $AUC_{LAST}$ (hr · ng/ml) | $AUC_{inf}$ (hr · ng/ml) | Cl (ml/hr/kg) | $V_{ss}$ (ml/kg) | $MRT_{last}$ (hr) | $MRT_{inf}$ (hr) | F (%) |
|---|---|---|---|---|---|---|---|---|---|---|---|
| iv | 2 | 0.25 | 649 | 6.5 | 5667 | 5709 | 350 | 2954 | 8.1 | 8.4 | NA |
| po | 5 | 4 | 517 | 6.2 | 8721 | 8778 | NA | NA | 9.7 | 10.0 | 61.6 |

Example 6: Compound 2 Mouse Efficacy Study for NASH

Figure 36:
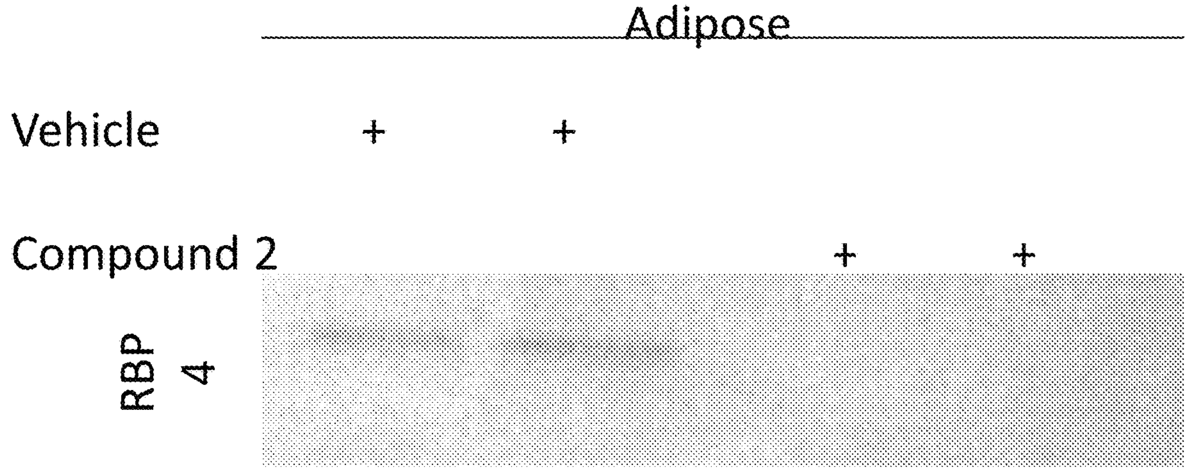
FIG. 36 illustrates a Western blot analysis of RBP4 levels in adipose tissue of ob/ob mice on a preventative dosing schedule wherein Compound 2 treatment is initiated at the same time as a western high fat diet (HFD), relative to an untreated control (vehicle).
Figure 37:
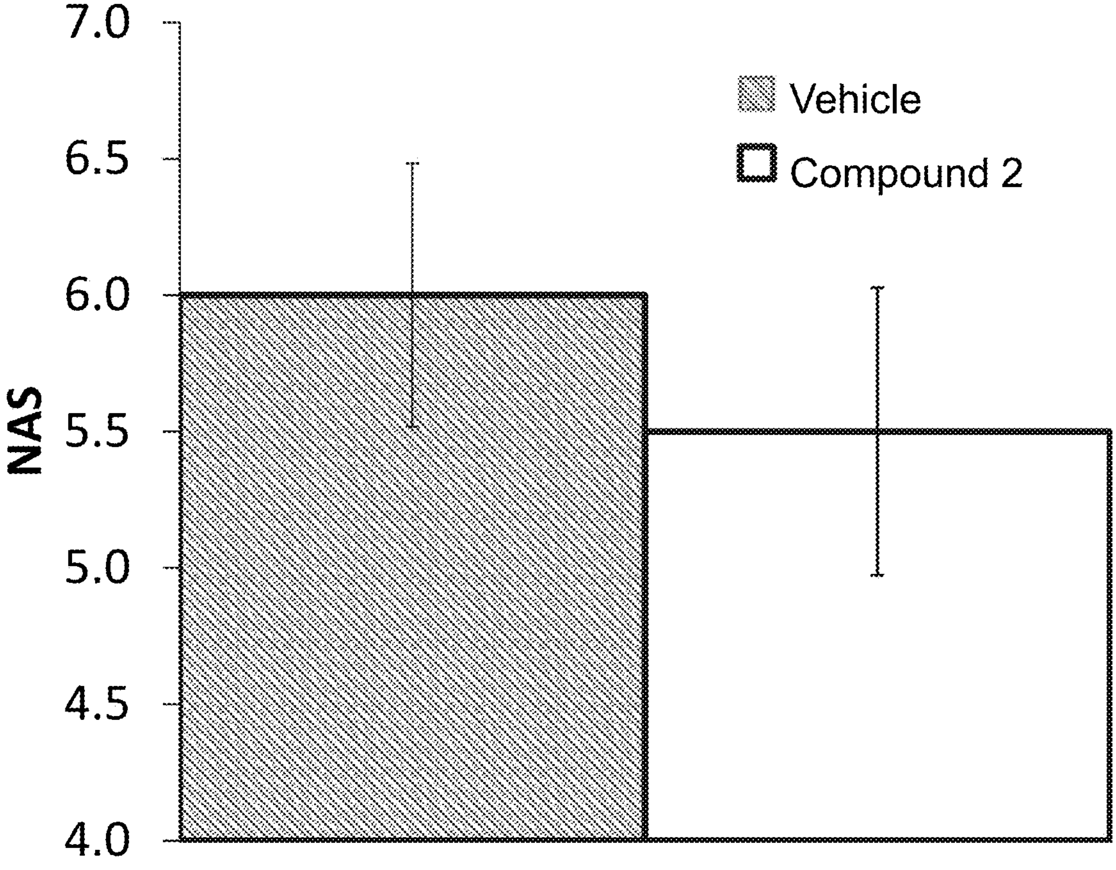
FIG. 37 illustrates NASH scores in ob/ob mice on a HFD after treatment with Compound 2.
Figure 38A:
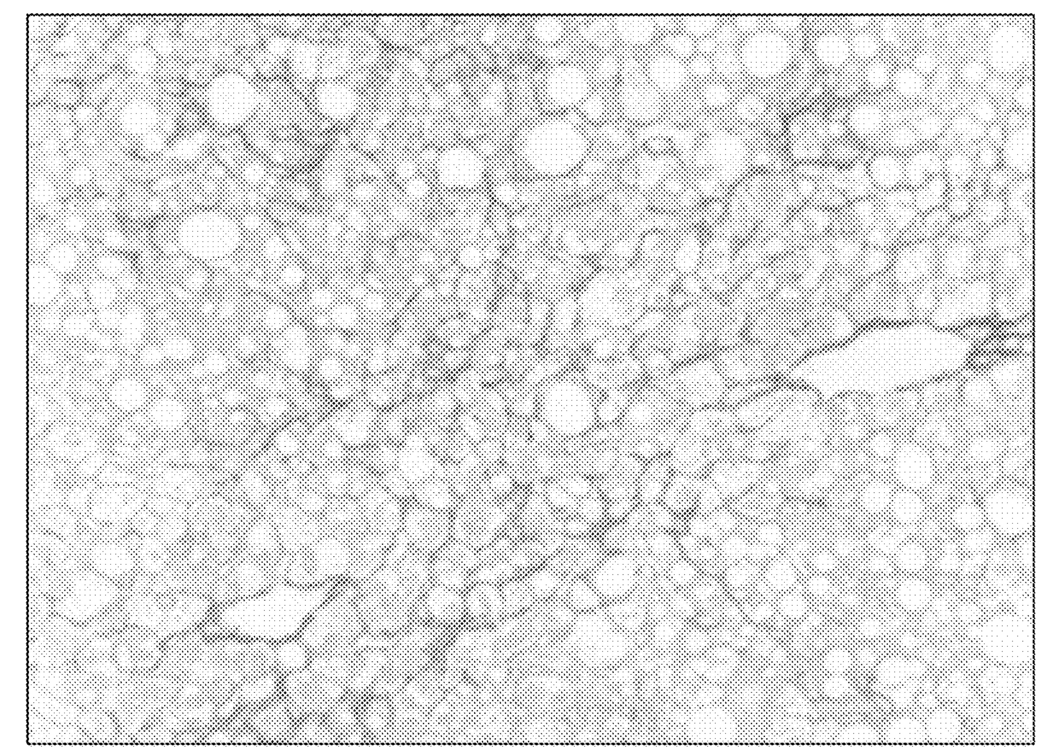
FIG. 38A illustrates a liver tissue section in ob/ob mice on a HFD after treatment with a control.
Figure 38B:
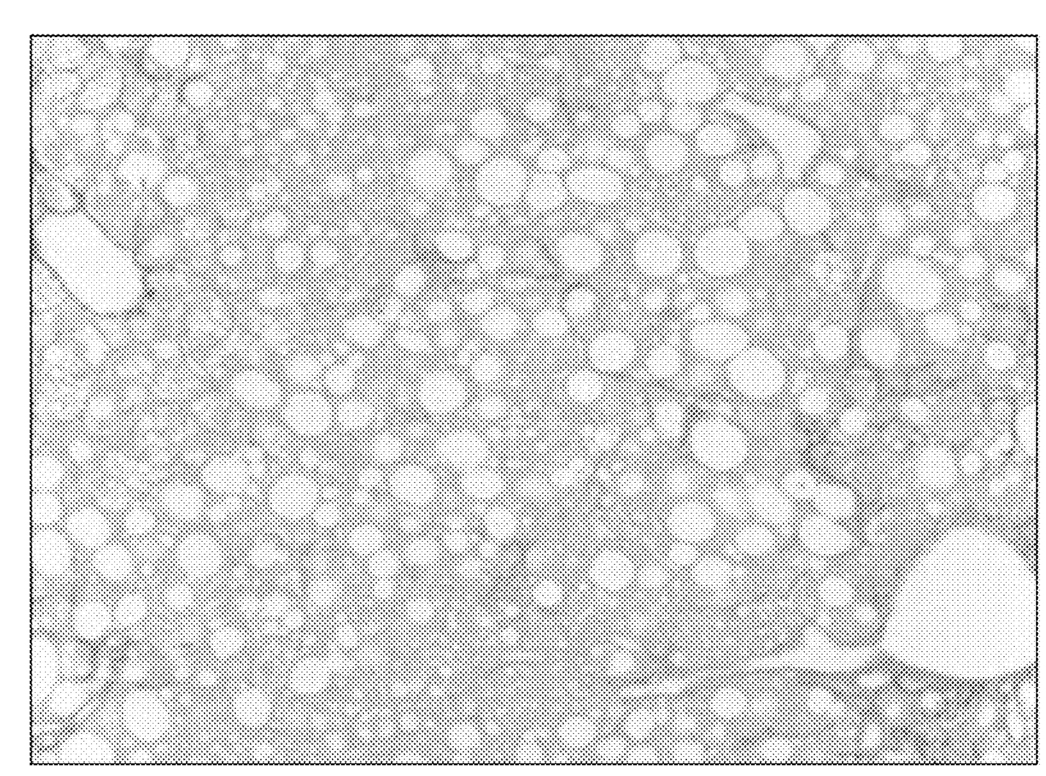
FIG. 38B illustrates a liver tissue section in ob/ob mice on a HFD after treatment with Compound 2.

An efficacy study was conducted with Compound 2 in ob/ob mice, using two different experimental designs, the results of which are found in FIGS. 32A-38B. Mice in cohort 1 were untreated or dosed orally with compound 2 (25 mg/kg) while being fed a high fat diet (HFD, FIG. 32A). Mice in cohort 2 were first conditioned with a high fat diet, and then treated with a control vehicle, Compound 2 (50 mg/kg) or obeticholic acid (OCA, 30 mg/kg). Mice treated with Compound 2 in both cohorts demonstrated decreased levels of RBP4 (FIGS. 33A and 33B), improved plasma insulin levels, and improved glucose tolerance relative to controls (FIGS. 34A-35B). Western blot analysis of fat tissue was obtained from four animals in cohort 1. Animals in cohort 1 treated with compound 2 showed lower RBP4 expression levels relative to the untreated control (FIG. 36). Animals in cohort 2 showed a reduction in NASH fibrosis scores relative to untreated controls, reflected as a decrease in the amount of bridging fibrosis (FIGS. 37, 38A, 38B).

Example 7: Phase 1 Protocol for Human Clinical Study for Compounds 1 and 2

Subjects. The subject population consists of healthy volunteers.

Objectives. Objects of the study are to characterize the systemic and hepatic safety of single and multiple doses of Compound 1 or 2, characterize the pharmacokinetics (PK) of single and multiple doses of Compound 1 or 2, and determine effects of single and multiple doses of Compound 1 or 2 on serum levels of retinol binding protein 4 (RBP4), a pharmacodynamics (PD) marker.

Study Design and Duration. The study is a randomized, double blind, placebo-controlled, sequential single and multiple ascending dose study. There are 5 dose levels in the single and 5 dose levels in the multiple ascending dose components. Each cohort consists of 8 subjects, 6 receiving compound 1 or 2 and 2 receiving placebo. Consistent with NINDS policies, 3-5 subjects in each cohort are female and efforts should be made to include diverse races and ethnicity. All subjects participate in a screening period lasting up to 28 days, during which they are assessed for eligibility.

Single Ascending Dose Treatment Group. Cohorts 1-3 reside in the research unit from Day −1 through Day 3; Cohorts 4 and 5 on Days −1 to 4. On Day −1 baseline safety and PD markers are obtained. Subjects receive a single oral dose on the morning of Day 1. Safety, PK and PD are obtained through Day 3 in early cohorts, though Day 4 in later. A phone call to ask about adverse events and concomitant medications takes place on Day 6. Subjects return for an outpatient visit on Day 8.

Multiple Ascending Dose Treatment Group. Cohorts 1-3 reside in the research unit from Day −1 to Day 3; Cohorts 4 and 5 from Day −1 to Day 4. Subjects receive the first oral dose on the morning of Day 1. Safety, PK and PD are obtained through Day 3 or 4, as appropriate, and subjects are discharged from the research unit with investigational product (IP) to take as an outpatient. Subjects return for outpatient visits on Days 6, 8, and 12. They are readmitted to the unit on the morning of Day and receive the final oral dose in the research unit. Safety, PK and PD are collected until discharge on Day 17 for Cohorts 1-3, day 18 for Cohorts 4 and 5. Subjects return for a last safety visit on Day 22. Specifics regarding safety, PK and PD collection for both SAD and MAD are described verbally in following sections, and presented in tabular form in Tables 5-10.

Number of Subjects. 40 subjects are in the single dose ascending group, 40 subjects are in the multiple dose ascending group, and there are 80 subjects total. Only subjects who discontinue prior to their first dose of IP are replaced.

Safety evaluation. Safety is evaluated by collecting adverse events, physical examination, Ocular examination (including slit lamp biomicroscopy, dilated ophthalmoscopy and intraocular pressure), Visual acuity, D-28 color vision text, Visual fields, Night vision questionnaire (multiple dose only), Vital signs (blood pressure, heart rate, temperature, respiratory rate), Weight, CBC with differential and platelets, serum chemistry, urinalysis, and ECG.

Twelve lead ECG are performed following recommendations in ICH E14 regarding evaluation of QTc prolongation in patients in early stage clinical trials. ECGs are performed in triplicate on Days 1, 2, 8, 15 and 16. Visual acuity is measured using Early Treatment of Diabetic Retinopathy Study (ETDRS) Visual Acuity charts 1 and 2. The chart is placed on an ETDRS light box which is hung at eye level on the wall or placed on a stand. Room lighting is at office levels and uniform between the subject and the light box. The distance from the patient's eyes to the Visual Acuity Chart is 4.0 meters. If vision tests are performed on the same day as an ERG, they are completed prior to pupil dilation.

Outcome Measures (PK). PK sampling of plasma is conducted in all subjects (for example predose, 0.5, 1, 1.5, 2, 3, 4, 8, 8, 10, 12, 16, 24, 36 and 48 hours post dose on Days 1-3 and 15-17; trough predose on other days; and times are finalized based on toxicokinetics). Compound 1 or 2 concentrations are determined using a high-pressure liquid chromatography coupled with a mass spectrometer (LC/MS/MS) method. The method is determined during toxicokinetic studies and then validated for human application. Validation includes determination of the limits of quantitation. If toxicokinetics show significant urinary excretion, then urine PK methods would be added. If toxicokinetics show significant metabolites, this method would be added.

Outcome Measures (PD). Serum RBP4 is measured using a validated commercial ELISA assay. Full-field ERG measurements are recorded after pupil dilation using 10% tropicamide and 30 minutes of dark adaptation at baseline and on Day 1 (approximately 6 hours), Day 2 (24-36 hours post-dose), and Day 4 (highest dose cohorts only). Responses are obtained from both eyes simultaneously and include the International Society for Clinical Electrocardiography of Vision (ISCEV) standard rod response (0.03 cd/$m^2$-seconds) and combined response (1.5 cd/$m^2$-seconds) in the dark, and the 31-Hz flicker response (2.25 cd/$m^2$-seconds) and 1-Hz cone response (2.25 cd/$m^2$-seconds) in the presence of a background illumination (34 cd/$m^2$).

Inhibition of the visual cycle as evidenced by the delay in restoration of the ERG b-wave amplitude following the photobleach is measured. After a 10-minute exposure to a full-field bleaching light (556 cd/$m^2$), recovery of the ERG is measured for 60 minutes at 10-minute intervals.

Investigational Product. Compound 1 or 2 is provided as 50 and 200 mg capsules. Matching placebo is provided as identical looking capsules. Instructions for shipping, storage and handling is provided in the protocol. The dose levels are 50, 100, 150, 200 and 400 mg. Compound 1 or 2 is taken in the morning in the fasting state, with 4-8 ounces of water, as needed.

Statistical Analysis. All subjects who receive IP are included in the safety population. All subjects who receive IP and have at least one post-treatment sample or determination are included in the PK analysis population. Analysis is by treatment assignment. Safety is evaluated by monitoring AEs, and by change from baseline on examinations and laboratory studies. The AEs are coded using the Medical Dictionary for Regulatory Activities (MedDRA) and summarized by system organ class (SOC) and preferred term, by severity, by relationship to study drug and study procedure, and by study drug dose. ECG parameters analyzed include heart rate, PR, QRS, QT, QTcB and QTcF intervals. Analysis of other examinations are specified in the protocol.

PK parameters are summarized using descriptive statistics (mean, standard deviation, coefficient of variation [CV], median, minimum, and maximum) by treatment. Geometric means are determined for $AUC_{0\text{-}inf}$, $AUC_{0\text{-}t}$, and $C_{max}$. The following PK parameters are determined: maximum observed plasma concentration ($C_{max}$) and time of the maximum observed plasma concentration ($T_{max}$), obtained directly from the data without interpolation; the apparent terminal elimination rate constant ($\lambda_Z$), determined by log-linear regression of the terminal plasma concentrations; area under the plasma concentration-time curve from time 0 to the time of the last measureable concentration ($AUC_{0\text{-}t}$), calculated by the linear trapezoidal method; apparent plasma terminal elimination half-life ($t_{1/2}$), calculated as $0.693/\lambda_Z$; area under the plasma concentration-time curve from time 0 to infinity ($AUC_{0\text{-}inf}$) where $AUC_{0\text{-}inf}=AUC_{0\text{-}4}+C_t/\lambda_Z$ and $C_t$ is the last measureable concentration; and apparent total plasma clearance (CL/F); and apparent volume of distribution during the terminal phase ($V_Z$/F).

The following outcome measures are calculated for ERGs: Absolute dark adapted prebleach rod amplitude at each time point; dark adapted prebleach rod amplitude at each time point as % baseline; recovery from photobleaching—% rod amplitude at 60 minutes recovery versus rod amplitude immediately prior to bleaching; and time to >90% recovery of rod amplitude from photobleaching.

Example 8: Treatment of NASH in Humans 250 adults with symptoms associated with nonalcoholic steatohepatitis (NASH) are randomly assigned to receive compound 1 or 2, each at a daily dose of 50 mg, 100 mg, 150 mg, 200 mg, 400 mg, or placebo, for up to 6 months. The primary outcome is an improvement in histologic features of nonalcoholic steatohepatitis, as assessed with the use of a composite of standardized scores for one or more of steatosis, lobular inflammation, hepatocellular ballooning, cirrhosis, and fibrosis. The results are analyzed following methods well known to the skilled artisan.

Example 9: Treatment of NAFLD and NASH in Humans

Subjects with NAFLD or NASH are treated with doses of either 50 or 100 mg/day of compound 1 or 2 for 6 months. Subjects are permitted their usual other medications (e.g. antidiabetic medications such as metformin or sulfonamides) but not glitazones, PPAR agonists, OCA, or similar medications. The subjects are assessed before the study, and at intervals during the study, such as every weeks during the study and ϕ weeks after the last dose of compound 1 or 2, for safety and pharmacodynamic evaluations.

MRIs of the subjects' livers are taken every 4 weeks during the study and ϕ weeks after completion of compound 1 or 2 dosing, to determine hepatic fat; and liver biopsies are taken before the study (to establish the diagnosis) and ϕ weeks after completion of compound 1 or 2 dosing. At each visit, after a 12-hour fast, blood is drawn and urine collected; and a standard metabolic panel, complete blood count, and standard urinalysis are performed. Blood is analyzed for total cholesterol, HDL-C, LDL-C, VLDL-C, TGs, apoB, and liver transaminases. The subjects also maintain health diaries, which are reviewed at each visit. The subjects show a dose-related improvement in their disease, as manifested by, for example, MRI and liver biopsy.

Example 10: Treatment of Obesity in Humans

Overweight subjects are treated with doses of either 50 or 100 mg/day of compound 1 or 2 for months. The subjects are not coffee drinkers or consumers of any other form of caffeine. The subjects are not to alter any other behavioral parameter such as diet or exercise. The subjects are assessed before the study, and at intervals during the study, such as every 2 weeks during the study and ϕ weeks after the last dose of compound 1 or 2, for safety and pharmacodynamic evaluations, and weight loss.

Example 11: Treatment of Type II Diabetes in Humans

Subjects diagnosed with type 2 diabetes mellitus are treated with doses of either 50 or 100 mg/day of compound 1 or 2 for 4 months. The subjects are not to alter any other behavioral parameter such as diet or exercise. The subjects are assessed before the study, and at intervals during the study, such as every 2 weeks during the study and ϕ weeks after the last dose of compound 1 or 2, for safety and pharmacodynamic evaluations, including markers of blood glucose, interstitial glucose, and insulin.

Example 12: Treatment of Diabetic Retinopathy in Humans

Adult patients aged between 35 and 65 years suffering from diabetes mellitus (insulin dependent or not insulin-dependent) and diabetic retinopathy (non-proliferative and proliferative diabetic retinopathy) are treated with either 100 or 200 mg/day of compound 1 or 2 for 4 months. The subjects are not to alter any other behavioral parameter such as diet or exercise. Patients submitted to previous treatment of the retinopathy with laser are excluded from the test. The subjects are assessed before the study, at intervals during the study, such as every 2 weeks during the study, at the end of the treatment period, and ϕ weeks after the last dose of compound 1 or 2, for safety and pharmacodynamic evaluations. The evaluations include markers of blood glucose, interstitial glucose, and insulin, as well as imaging including fundus photography, optical coherence tomography, fluoroangiographic examination, and retinography. The fluoroangiography and retinography are carried out according to the standard methods and the photograms are graduated by giving a score to the plasmatic exudation and to the hard exudates on the basis of the ERDRS Classification.

We claim:

1. A method of treating a metabolic disease or disorder in a subject in need thereof, the method comprising administering to the subject a composition comprising a therapeutically effective amount of a compound of Formula (I), or a pharmaceutically acceptable salt thereof Formula (I)

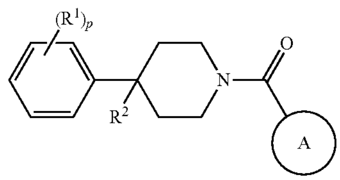

wherein:

each $R^1$ is independently halogen, haloalkyl, or alkyl;

$R^2$ is H, OH, or halogen;

p is 0, 1, 2, 3, 4, or 5; and

A has the structure:

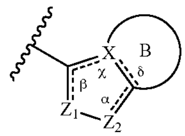

wherein:

α, β, χ, and δ are each independently absent or present, and when present each is a bond;

X is N;

$Z_1$ is S, O, or N;

$Z_2$ is S, O, N, or $NR^3$;

$R^3$ is H, $C_1$-$C_4$ alkyl, or oxetane; and

B is a substituted or unsubstituted fused 5-, 6-, or 7-membered ring structure, wherein the metabolic disease or disorder is liver fibrosis, liver cancer, or liver cirrhosis.

2. The method of claim 1, wherein: when $\alpha$ is present, then $Z_1$ and $Z_2$ are N, X is N, $\beta$ is present, and $\chi$ and $\delta$ are absent.

3. The method of claim 1, wherein A has the structure

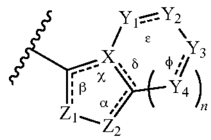

wherein:

n is 0, 1, or 2;

$\alpha$, $\beta$, $\chi$, $\delta$, $\varepsilon$, and $\phi$ are each independently absent or present, and when present each is a bond;

$Z_1$ is S, O, or N;

$Z_2$ is S, O, N or $NR^3$, wherein $R^3$ is H, $C_1$-$C_4$ alkyl, or oxetane;

X is N;

$Y_1$, $Y_2$, $Y_3$ and each occurrence of $Y_4$ are each independently $CR^4$, $C(R^5)_2$, $NR^6$, O, N, $SO_2$, or —(C═O)—, wherein:

each $R^4$ is independently H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$;

each $R^5$ is independently H or $C_1$-$C_{10}$ alkyl; and each $R^6$ is independently H, $C_1$-$C_{10}$ alkyl, $C_3$-$C_6$ cycloalkyl, —($C_1$-$C_{10}$ alkyl)$CF_3$, —($C_1$-$C_{10}$ alkyl)$OCH_3$, —($C_1$-$C_{10}$ alkyl)-halogen, —$SO_2$($C_1$-$C_{10}$ alkyl), —$SO_2$($C_1$-$C_{10}$ alkyl)-$CF_3$, —$SO_2$ ($C_1$-$C_{10}$ alkyl)$OCH_3$, —$SO_2$($C_1$-$C_{10}$ alkyl)-halogen, —C(O)($C_1$-$C_{10}$ alkyl), —C(O)($C_1$-$C_{10}$ alkyl)$CF_3$, —C(O)($C_1$-$C_{10}$ alkyl)$OCH_3$, —C(O)($C_1$-$C_{10}$ alkyl)-halogen, —C(O)NH($C_1$-$C_{10}$ alkyl), —C(O)N($C_1$-$C_{10}$ alkyl)$_2$, —($C_1$-$C_{10}$ alkyl)C(O)OH, —C(O)$NH_2$, or oxetane.

4. The method of claim 1, wherein:

when $\alpha$ is present, then $Z_1$ and $Z_2$ are N, X is N, $\beta$ is present, and $\chi$ and $\delta$ are absent;

when $\varepsilon$ and $\phi$ are each present, then n=1, and each of $Y_1$, $Y_2$, $Y_3$, and $Y_4$, are independently —$CR^4$— or N; or when $\varepsilon$ and $\phi$ are each absent, then n=0, 1 or 2, each of $Y_1$, $Y_2$, $Y_3$, and each occurrence of $Y_4$ are independently $C(R^5)_2$, $NR^6$, O, or $SO_2$.

5. The method of claim 1, wherein:

$\alpha$, $\beta$, $\varepsilon$, and $\phi$ are present;

$\chi$ and $\delta$ are absent;

$Z_1$ is N;

$Z_2$ is N; and

X is N.

6. The method of claim 1, wherein A has the structure:

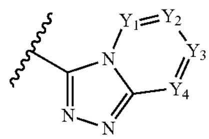

wherein:

$Y_1$, $Y_2$, $Y_3$ and $Y_4$ are each independently $CR^4$ or N; and each $R^4$ is independently H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$.

7. The method of claim 1, wherein A has the structure

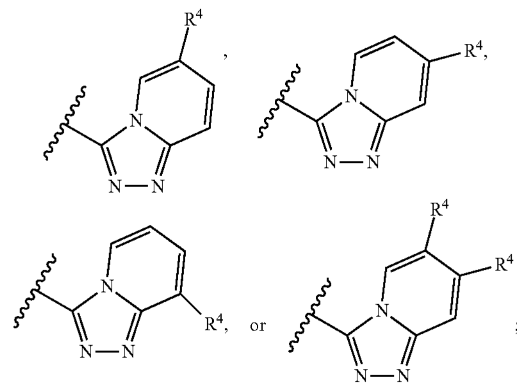

wherein:

each $R^4$ is independently H, halogen, $C_1$-$C_4$ alkyl, $C_3$-$C_6$ cycloalkyl, —O($C_1$-$C_4$ alkyl), —CN, —$CF_3$, —C(O)OH, —C(O)$NH_2$, —C(O)N$(CH_3)_2$, —C(O)NH$CH_3$, or —NHC(O)N$(CH_3)_2$.

8. The method of claim 1, wherein each $R^1$ is independently F, Br, Cl, $C_{1-6}$ haloalkyl, or $C_{1-6}$ alkyl.

9. The method of claim 1, wherein each $R^1$ is independently F or $CF_3$.

10. A method of treating a metabolic disease or disorder in a subject in need thereof, the method comprising administering to the subject a composition comprising a therapeutically effective amount of a compound having the structure:

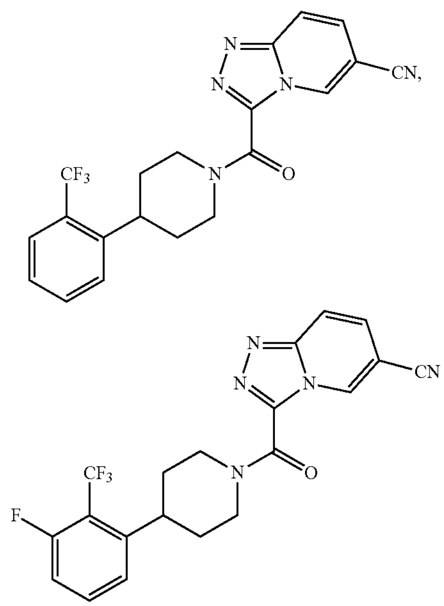

or a pharmaceutically acceptable salt thereof, wherein the metabolic disease or disorder is liver fibrosis, liver cancer, or liver cirrhosis.

11. A method of treating a metabolic disease or disorder in a subject in need thereof, the method comprising administering to the subject a composition comprising a therapeutically effective amount of a compound having the structure:

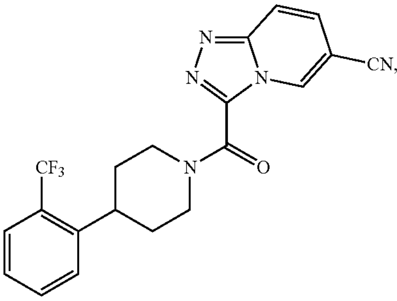

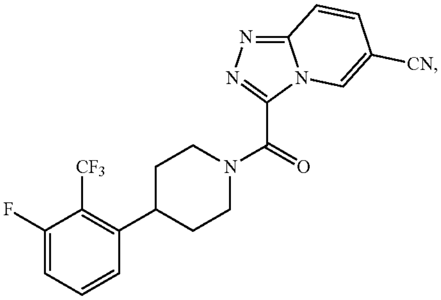

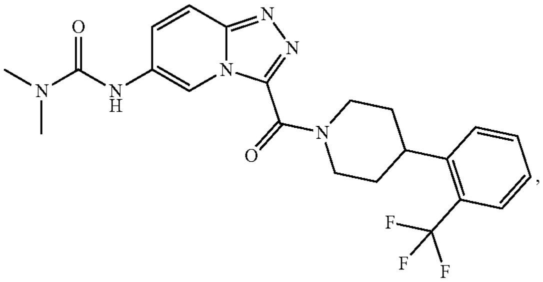

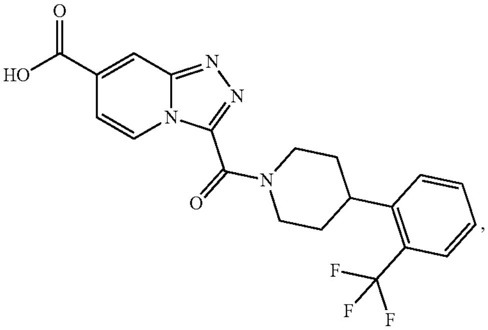

-continued

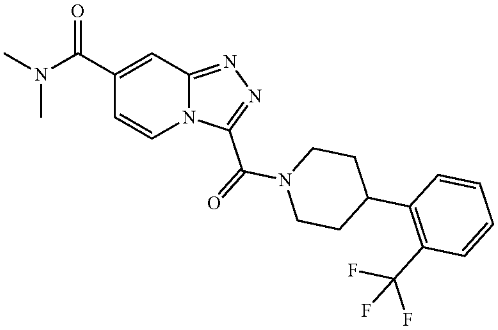

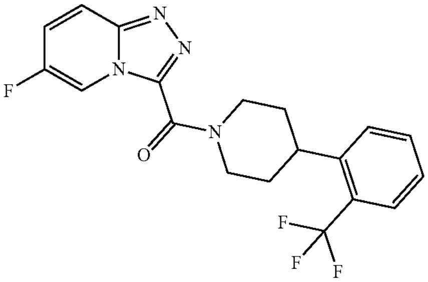

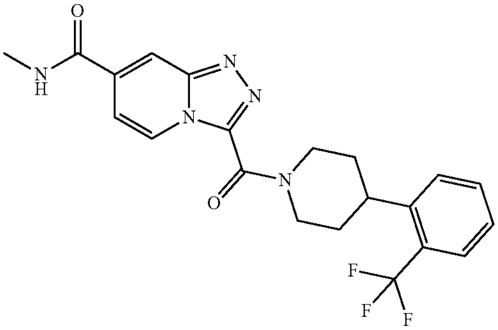

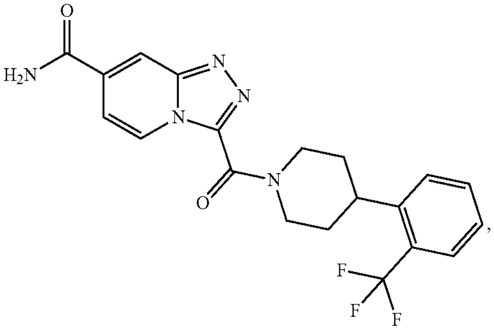

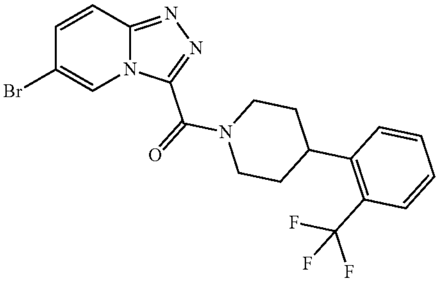

-continued
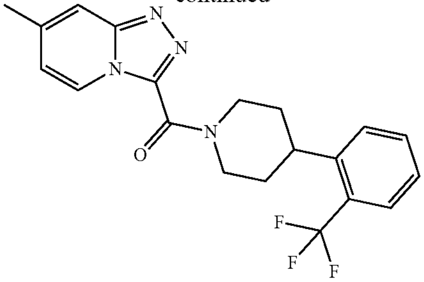,
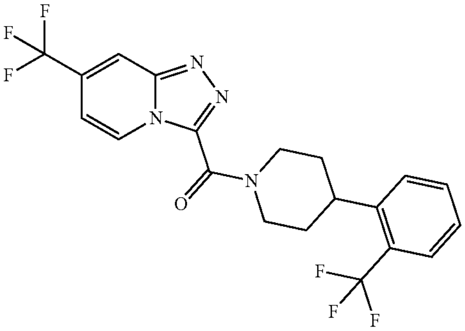,
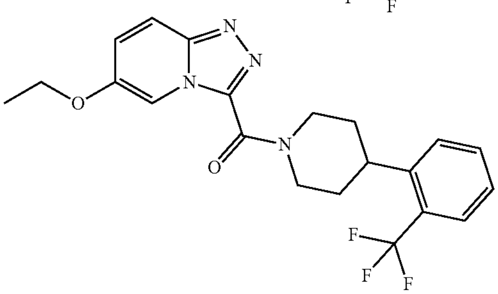,
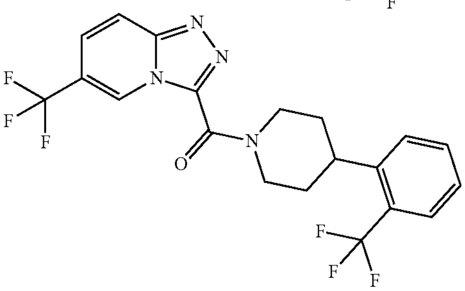,
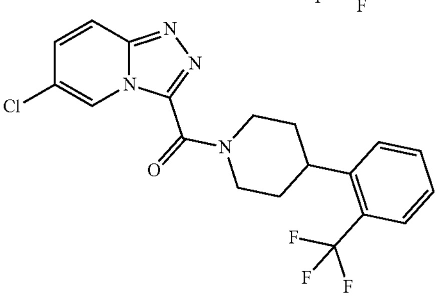,
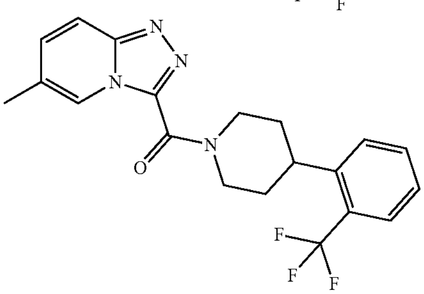,
-continued
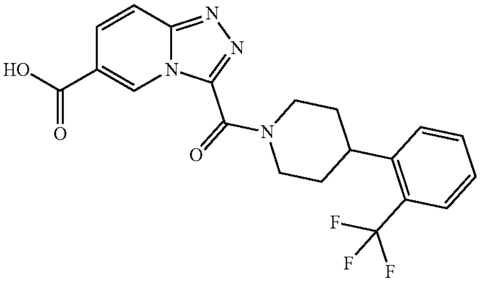,
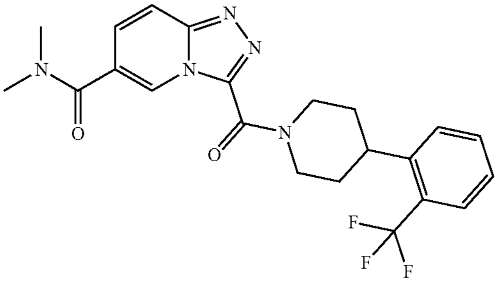,
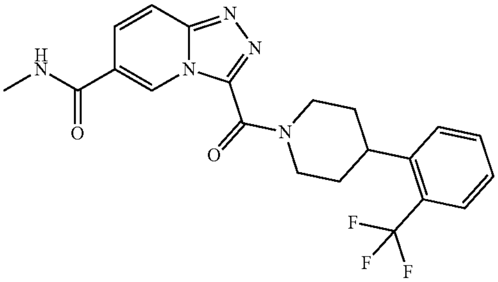,
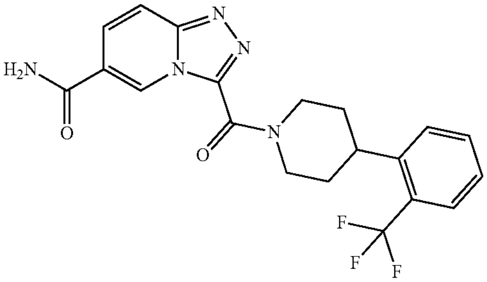,
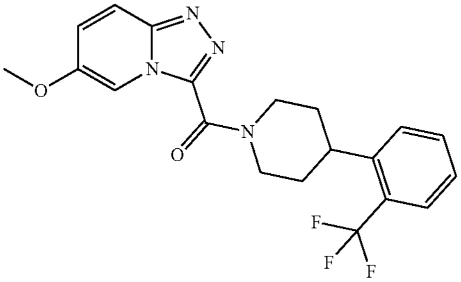, -continued
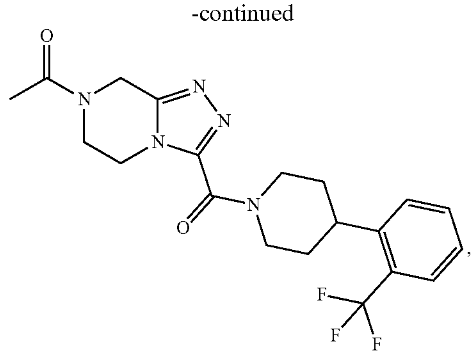
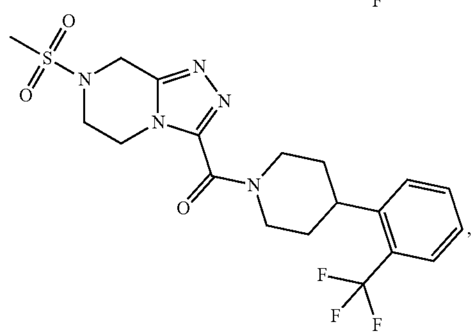
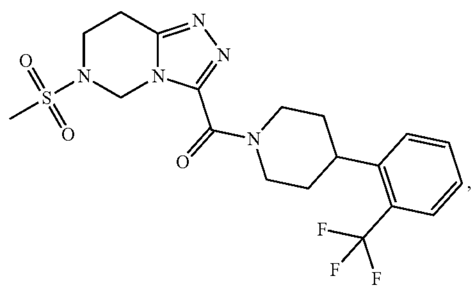
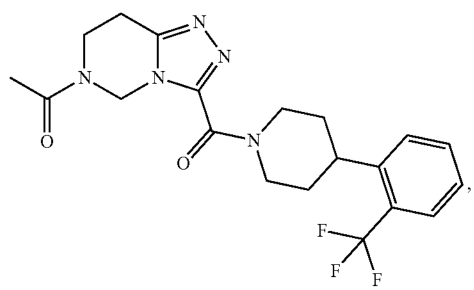
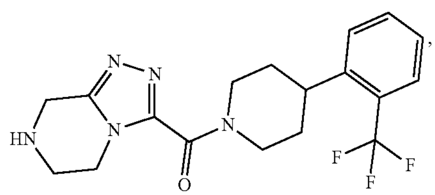
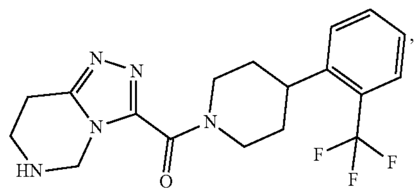
-continued
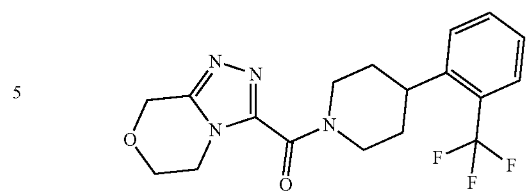
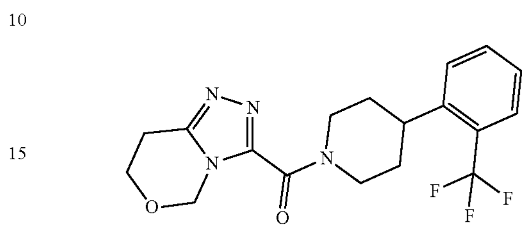
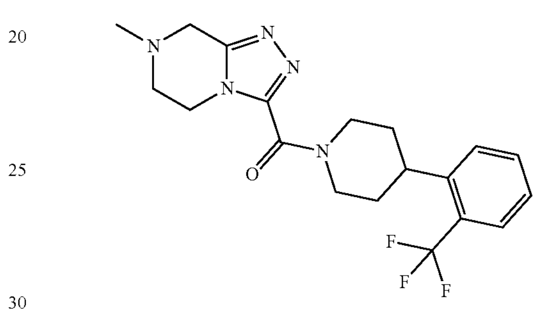
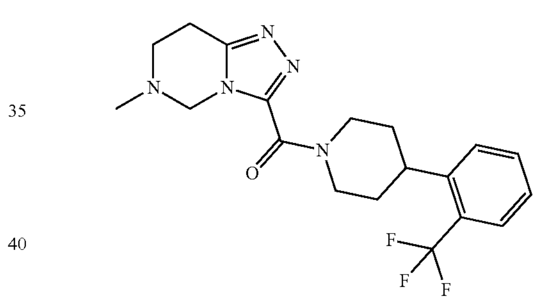
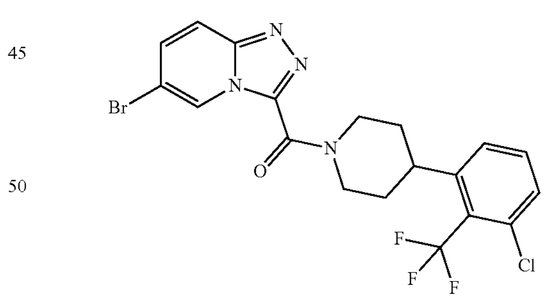
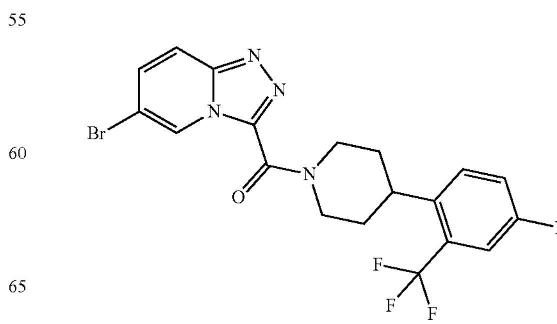

-continued
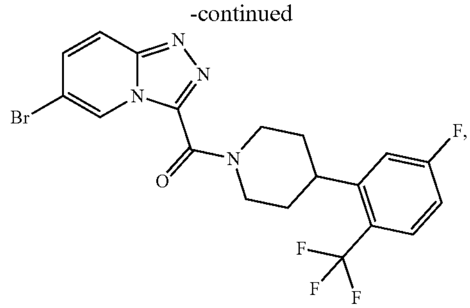
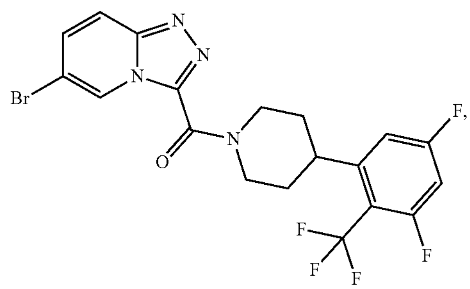
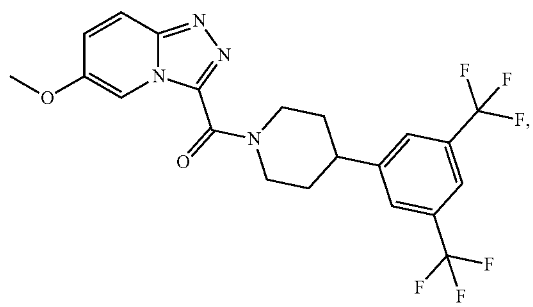
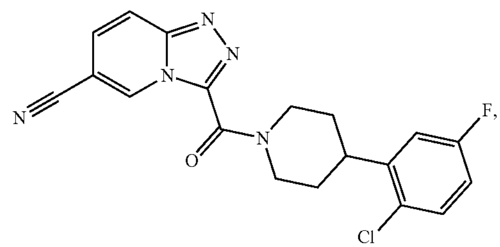
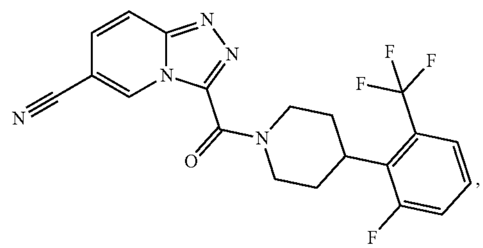
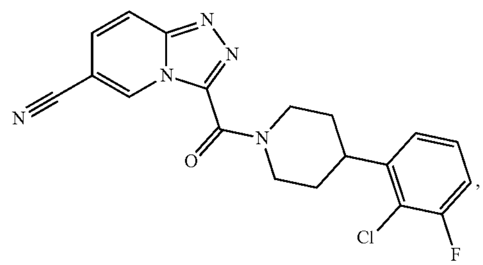
-continued
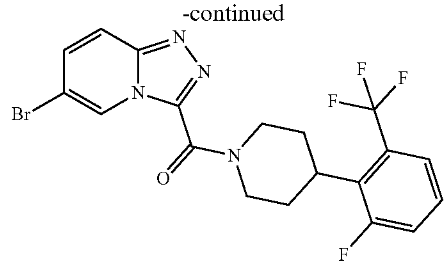
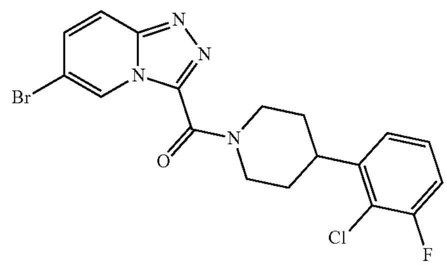
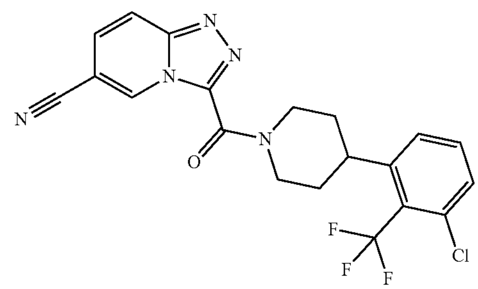
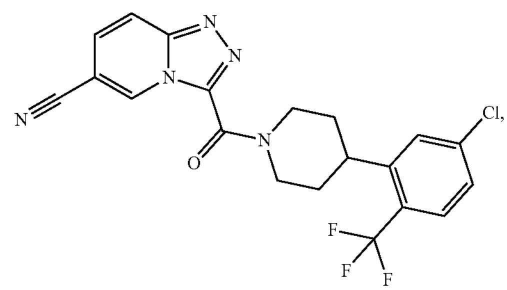
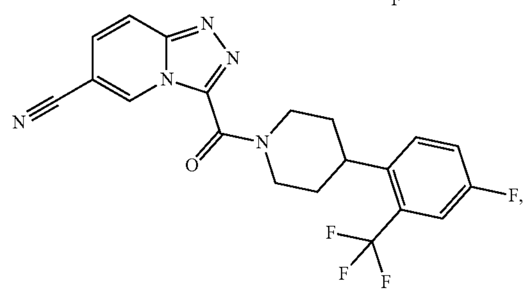
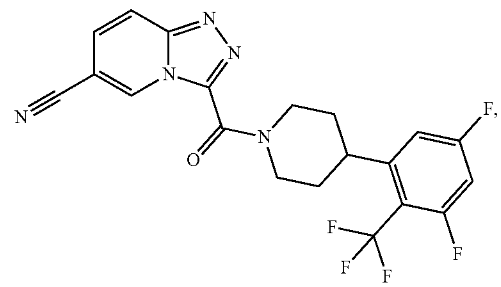

-continued

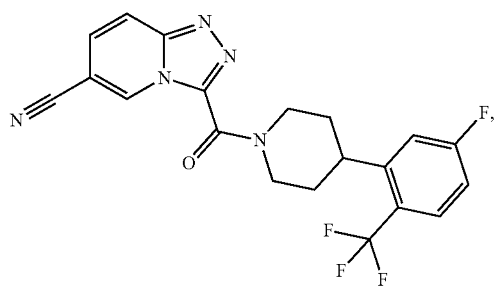

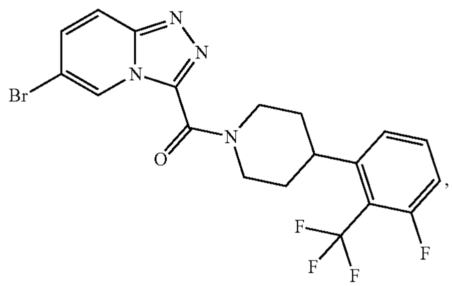

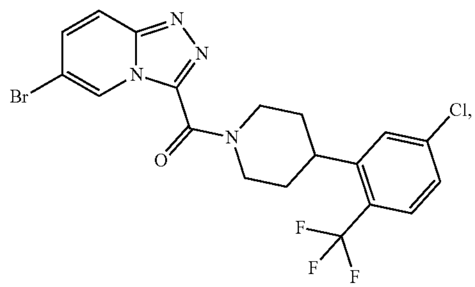

-continued

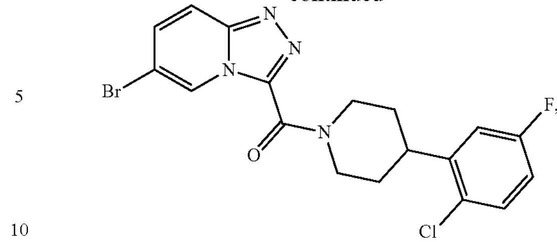

or a pharmaceutically acceptable salt thereof, wherein the metabolic disease or disorder is liver fibrosis, liver cancer, or liver cirrhosis.

12. The method of claim 1, wherein the metabolic disease or disorder is liver cancer.

13. The method of claim 1, wherein the therapeutically effective amount of a compound of Formula (I), or a pharmaceutically acceptable salt thereof is up to 25 mg per day, up to 50 mg per day, up to 75 mg per day, up to 100 mg per day, up to 150 mg per day, up to 200 mg per day, up to 400 mg per day, up to 600 mg per day, up to 800 mg per day, or up to 1000 mg per day.

14. The method of claim 1, wherein 24 hours after administration of a compound of Formula (I), or a pharmaceutically acceptable salt thereof, the serum or plasma levels of RBP4 are reduced by at least 50% from baseline.

15. The method of claim 1, wherein 24 hours after administration of a compound of Formula (I), or a pharmaceutically acceptable salt thereof, the serum or plasma levels of RBP4 are reduced by at least 1 mg/dL.

16. The method of claim 1, wherein the disease or disorder is liver fibrosis.

17. The method of claim 1, wherein the disease or disorder is liver cirrhosis.

18. The method of claim 1, wherein the compound is administered to the subject orally or intravenously.

19. The method of claim 1, wherein the administration is to treat an existing disease or disorder.

20. The method of claim 1, wherein the administration is provided as prophylaxis.

* * * * *